United States Patent
Chun et al.

(10) Patent No.: US 9,732,182 B2
(45) Date of Patent: Aug. 15, 2017

(54) EPOXY COMPOUND HAVING ALKOXYSILYL GROUP, METHOD OF PREPARING THE SAME, COMPOSITION AND CURED PRODUCT COMPRISING THE SAME, AND USE THEREOF

(71) Applicant: KOREA INSTITUTE OF INDUSTRIAL TECHNOLOGY, Cheonan (KR)

(72) Inventors: Hyun-Aee Chun, Seongnam (KR); Sung-Hwan Park, Gunpo (KR); Yun-Ju Kim, Seoul (KR); Su-Jin Park, Ansan (KR); Sook-Yeon Park, Gunpo (KR); Sang-Yong Tak, Busan (KR)

(73) Assignee: KOREA INSTITUTE OF INDUSTRIAL TECHNOLOGY, Cheonan (KR)

( * ) Notice: Subject to any disclaimer, the term of this patent is extended or adjusted under 35 U.S.C. 154(b) by 0 days.

(21) Appl. No.: 14/834,387

(22) Filed: Aug. 24, 2015

(65) Prior Publication Data

US 2015/0361211 A1 Dec. 17, 2015

Related U.S. Application Data

(63) Continuation of application No. PCT/KR2014/001528, filed on Feb. 25, 2014.

(30) Foreign Application Priority Data

Feb. 25, 2013 (KR) .................. 10-2013-0020134
Feb. 25, 2014 (KR) .................. 10-2014-0021884

(51) Int. Cl.
| | |
|---|---|
| C08G 59/06 | (2006.01) |
| C08G 59/02 | (2006.01) |
| C07F 7/18 | (2006.01) |
| C09J 163/00 | (2006.01) |
| C07D 303/12 | (2006.01) |
| C07D 303/36 | (2006.01) |
| C07D 405/06 | (2006.01) |
| C08L 63/00 | (2006.01) |
| C09D 163/00 | (2006.01) |
| C08G 59/30 | (2006.01) |

(52) U.S. Cl.
CPC ........... *C08G 59/02* (2013.01); *C07D 303/12* (2013.01); *C07D 303/36* (2013.01); *C07D 405/06* (2013.01); *C07F 7/1836* (2013.01); *C08L 63/00* (2013.01); *C09D 163/00* (2013.01); *C09J 163/00* (2013.01); *C08G 59/06* (2013.01); *C08G 59/306* (2013.01); *Y10T 428/239* (2015.01)

(58) Field of Classification Search
CPC ....... C08G 59/02; C08G 59/306; C08G 59/06
See application file for complete search history.

(56) References Cited

U.S. PATENT DOCUMENTS

| | | | | |
|---|---|---|---|---|
| 5,019,607 | A * | 5/1991 | Coltrain ................ | C08G 18/58 523/435 |
| 6,525,160 | B1 | 2/2003 | Goda et al. | |
| 7,501,480 | B2 * | 3/2009 | Westhoff ............... | C09D 4/00 528/27 |
| 2008/0214734 | A1* | 9/2008 | Yang ..................... | B82Y 30/00 525/102 |
| 2008/0221238 | A1* | 9/2008 | Su ........................ | C07F 7/1836 523/435 |
| 2008/0319142 | A1 | 12/2008 | Kikkawa et al. | |
| 2009/0286924 | A1* | 11/2009 | Tsuchida .............. | C07F 7/1836 524/588 |
| 2015/0247033 | A1 | 9/2015 | Chun et al. | |

FOREIGN PATENT DOCUMENTS

| | | |
|---|---|---|
| EP | 2 835 373 A1 | 2/2015 |
| EP | 2 933 257 A1 | 10/2015 |
| JP | 57-016446 A | 1/1982 |
| JP | S57-141447 A | 9/1982 |
| JP | S63-280778 A | 11/1988 |
| JP | 10-045871 A | 2/1998 |
| JP | 2005-281528 A | 10/2005 |
| JP | 2009-275015 A | 11/2009 |
| JP | 2012-129010 A | 7/2012 |
| JP | 5009535 B2 | 8/2012 |
| KR | 10-2006-0076417 A | 7/2006 |
| KR | 10-2008-0106051 A | 12/2008 |

(Continued)

OTHER PUBLICATIONS

Ogura Ichiro, "Relation between Chemical Structures and Characteristics on Epoxy Resins", DIC Technical Review, 2001, pp. 1-12, No. 7.

(Continued)

*Primary Examiner* — Margaret Moore

(57) ABSTRACT

Provided are alkoxysilylated epoxy compounds, a composite of which exhibits good heat resistance properties, low CTE and increased glass transition temperature, and a cured product thereof exhibits good flame retardancy without requiring separate coupling agent, a method for preparing the same and a composition and a cured product including the same. An alkoxysilylated epoxy compound including an epoxy group and at least one alkoxysilyl group of an S1 substituent selected from Formulae S11 to S15 or an S2 substituent selected from Formulae S21 to S25; a method for preparing the same by epoxy ring-opening reaction of starting material and alkoxysilylation, an epoxy composition including the epoxy compound, and a cured product and a use of the composition, are provided. Since chemical bonds may be formed between alkoxysilyl group and filler and between alkoxysilyl groups, chemical bonding efficiency of the composite may be improved.

12 Claims, No Drawings

(56) References Cited

FOREIGN PATENT DOCUMENTS

| KR | 10-1596880 B1 | 2/2016 |
|---|---|---|
| WO | WO 95/31512 A1 | 11/1995 |
| WO | WO 2006/025278 A1 | 3/2006 |
| WO | WO 2008/112150 A1 | 9/2008 |

OTHER PUBLICATIONS

Ogura Ichiro, "State-of the-arts Technologies of Hyper Epoxy Resins beyond History", DIC Technical Review, 2005, pp. 21-28, No. 11.

"Polymer Synthesis", Experimental Chemistry Course (4$^{th}$ edition), May 6, 1992, pp. 431-438, Japanese Chemical Society Corporation, Maruzen Inc., Tokyo.

Extended European Search Report for European Application No. 14754737.6, dated Sep. 6, 2016.

Gulayy Bayramoglu, et al., "Synthesis and characterization of UV-curable dual hybrid oligomers based on epoxy acrylate containing pendant alkoxysilane groups", Progress in Organic Coatings, Jun. 2, 2006, pp. 50-55, vol. 57, Marmara University, Faculty of Art & Science, Department of Chemistry, Istanbul, Turkey.

Chunguang Li, et al., "Preparation and Characterization of UV-Cured Hybrid Coatings by Triethoxysilane-Modified Dimethacrylate Based on Bisphenol-S Epoxy", Journal of Applied Polymer Science, Jan. 15, 2013, pp. 2189-2195, vol. 129, Issue 4, State Key Laboratory of Chemical Resource Engineering, Beijing, China.

Safak Oturakli, "Characterization and Corrosion Performance of γ-Glycidox Ypropyltrimethoxysilane Modified Epoxy Polymer", 73 pages, Jul. 13, 2010, A Thesis, Graduate School of Engineering and Sciences of İzmir Institute of Technology, İzmir, Turkey.

* cited by examiner

EPOXY COMPOUND HAVING ALKOXYSILYL GROUP, METHOD OF PREPARING THE SAME, COMPOSITION AND CURED PRODUCT COMPRISING THE SAME, AND USE THEREOF

BACKGROUND

Technical Field

The present invention relates to an epoxy compound having an alkoxysilyl group (hereinafter 'alkoxysilylated epoxy compound'), a composite thereof exhibiting good heat resistance properties and/or a cured product thereof exhibiting good flame retardancy, a method for preparing the same, a composition comprising the same, a cured product thereof, and a use thereof. More particularly, the present invention relates to an alkoxysilylated epoxy compound, composites thereof exhibiting good heat resistance properties, in particular, low coefficients of thermal expansion (CTE) and high glass transition temperatures (including transition temperature-less (Tg-less) states, which means that the composites do not have a glass transition temperature) and not requiring a separate coupling agent, a method for preparing the same, a composition comprising the same, a cured product thereof, and a use thereof.

Background Art

The coefficient of thermal expansion of a cured epoxy product is significantly high, on the level of several to several tens of times than the CTE of a ceramic material or a metal material. Thus, in the case that an epoxy material is used in conjunction with an inorganic material or a metal material, the properties and processability of a part may be significantly degraded due to the different CTEs of the polymer material and the inorganic material or the metal material. For example, during semiconductor packaging in which a silicon wafer and an epoxy substrate are used in parallel, product defects such as the generation of cracks, the warpage in a substrate, the peeling of a coating layer, the cracking of a substrate, and the like, may be generated due to a high CTE-mismatch between constituent elements due to changes in processing and/or applied temperature conditions.

Because of the high CTE of the epoxy material and the resultant dimensional change of the material, the development of technologies such as next generation semiconductor substrates, printed circuit boards (PCBs), packaging, organic thin film transistors (OTFTs), and flexible display substrates may be limited. Particularly, at the current time, in the semiconductor and PCB fields, designers are facing challenges in the design of next generation parts requiring high degrees of integration, miniaturization, flexibility, performance, and the like, in securing processability and reliability in parts due to polymer materials having significantly high CTEs as compared to metal/ceramic materials. In other words, due to the high thermal expansion properties of polymer materials at part processing temperatures, defects may be generated therein, processability may be limited, and the design of parts and the securing of processability and reliability therein may be objects of concern. Accordingly, improved thermal expansion properties, namely dimensional stability of the epoxy material are necessary in order to secure processability and reliability in electronic parts.

To date, in order to obtain a low CTE in a cured epoxy product, (1) a method of producing a composite of an epoxy compound with inorganic particles (an inorganic filler) and/or fabrics or (2) a method of designing a novel epoxy compound having a decreased CTE have been used.

In the case that the composite of the epoxy compound and the inorganic particles as the filler is formed in order to improve thermal expansion properties, a large amount of inorganic silica particles, having a diameter of about 2 to 30 μm, is required to be used to obtain a CTE decrease effect. However, due to the presence of the large amount of inorganic particles, the processability and physical properties of the parts may be deteriorated. That is, the presence of the large amount of inorganic particles may decrease fluidity, and voids may be generated during the filling of narrow spaces. In addition, the viscosity of the material may increase exponentially due to the addition of the inorganic particles. Further, the size of the inorganic particles tends to decrease due to semiconductor structure miniaturization. In the case that a filler having a particle size of 1 μm or less is used, an increase in viscosity may be intensified. In the case that inorganic particles having a large average particle diameter are used, the frequency of insufficient filling in the case of a composition comprising a resin and the inorganic particles may increase. While the CTE may largely decrease in the case that a composition comprising an organic resin and a fiber as the filler is used, the CTE may remain high, as compared to that of a silicon chip or the like.

As described above, the manufacturing of highly integrated and high performance electronic parts for next generation semiconductor substrates, PCBs, and the like, may be limited due to limitations in the technology of forming composites of epoxy resins. Thus, the development of an epoxy composite having improved brittleness and adhesiveness as well as improved heat resistance properties—namely, a low CTE and a high glass transition temperature—is required to overcome poor thermal properties due to a high CTE and processability of a common epoxy composite.

SUMMARY

Technical Problem

An aspect of the present invention provides an epoxy compound having an alkoxysilyl group, a composite thereof exhibiting improved heat resistance properties, particularly a low CTE and a high glass transition temperature and/or a cured product thereof exhibiting good flame retardancy.

Another aspect of the present invention provides a method for preparing an epoxy compound having an alkoxysilyl group, a composite thereof exhibiting improved heat resistance properties, particularly a low CTE and a high glass transition temperature and/or a cured product thereof exhibiting good flame retardancy.

Another aspect of the present invention provides an epoxy composition comprising an epoxy compound having an alkoxysilyl group, a composite thereof exhibiting improved heat resistance properties, particularly a low CTE and a high glass transition temperature and/or a cured product thereof exhibiting good flame retardancy.

Another aspect of the present invention provides a cured product comprising an epoxy composition according to an embodiment of the present invention, a composite thereof exhibiting improved heat resistance properties, particularly a low CTE and a high glass transition temperature and/or a cured product thereof exhibiting good flame retardancy.

In addition, another aspect of the present invention provides a use of an epoxy composition according to an embodiment of the present invention.

DETAILED DESCRIPTION

Technical Solution

According to the first embodiment of the present invention, there is provided an epoxy compound having an alkoxysilyl group, having an epoxy group and at least one alkoxysilyl group of an S1 substituent independently selected from the group consisting of Formulae S11 to S15 or an S2 substituent independently selected from the group consisting of Formulae S21 to S25 in a core.

[Formula S1]

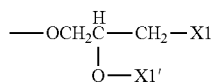
(S11)

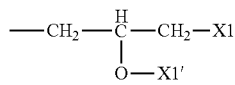
(S12)

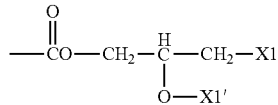
(S13)

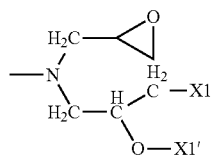
(S14)

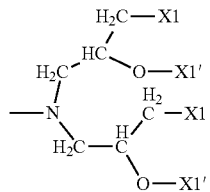
(S15)

In Formulae S11 to S15, X1 is $OR_4$, OH, $NR_4R_5$, $SR_4$ or $OCONH(CH_2)_3SiR_1R_2R_3$, X1' is H or $CONH(CH_2)_3SiR_1R_2R_3$, at least one of $R_1$ to $R_3$ is an alkoxy group having 1 to 5 carbon atoms, and the remainder are alkyl groups having 1 to 10 carbon atoms, and $R_4$ or $R_5$ may be an alkyl group, an alkenyl group, an aryl group or an aralkyl group having 1 to 20 carbon atoms and may include a hetero atom including N, O, P or S.

[Formula S2]

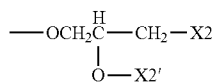
(S21)

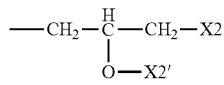
(S22)

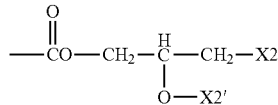
(S23)

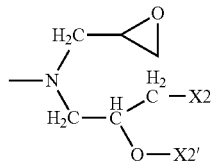
(S24)

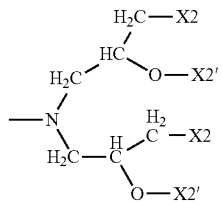
(S25)

In Formulae S21 to S25, X2 is $OR_4$, OH, $NR_4R_5$, $SR_4$ or $O(CH_2)_nCH_2CH_2SiR_1R_2R_3$, X2' is H or $(CH_2)_nCH_2CH_2SiR_1R_2R_3$, at least one of $R_1$ to $R_3$ is an alkoxy group having 1 to 5 carbon atoms, and the remainder are alkyl groups having 1 to 10 carbon atoms, and $R_4$ or $R_5$ may be an alkyl group, an alkenyl group, an aryl group or an aralkyl group having 1 to 20 carbon atoms and may include a hetero atom including N, O, P or S.

According to a second embodiment of the present invention, the epoxy compound having an alkoxysilyl group of the first embodiment, in which the epoxy group is selected from the group consisting of Formulae S41 to S45, may be provided.

[Formula S4 (3)]

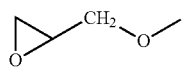
(S41)

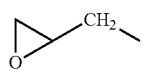
(S42)

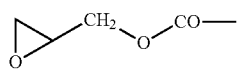
(S43)

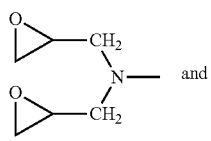
(S44)

and

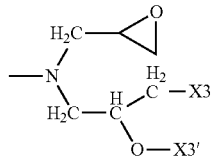
(S45)

in the formula S45, X3 is $OR_4$, OH, $NR_4R_5$, $SR_4$, $OCONH(CH_2)_3SiR_1R_2R_3$ or $O(CH_2)_nCH_2CH_2SiR_1R_2R_3$, X3' is H, $CONH(CH_2)_3SiR_1R_2R_3$ or $(CH_2)_nCH_2CH_2SiR_1R_2R_3$, at least one of $R_1$ to $R_3$ is an alkoxy group having 1 to 5 carbon atoms, and the remainder are alkyl groups having 1 to 10 carbon atoms, and $R_4$ or $R_5$ may be an alkyl group, an alkenyl group, an aryl group or an aralkyl group having 1 to 20 carbon atoms and may include a hetero atom including N, O, P or S.

According to a third embodiment of the present invention, the epoxy compound having an alkoxysilyl group of the first or second embodiment, in which the core of the epoxy compound is a bisphenol, a biphenyl, a naphthalene, a benzene, a thiodiphenol, a fluorene, an anthracene, an isocyanurate, a triphenylmethane, a 1,1,2,2-tetraphenylethane, a tetraphenylmethane, a 4,4'-diaminodiphenylmethane, an aminophenol, an alicyclic, an aliphatic, or a novolac unit, may be provided.

According to a fourth embodiment of the present invention, the epoxy compound having an alkoxysilyl group of the fourth embodiment, in which the core is one selected from the group consisting of Formulae A' to N', may be provided.

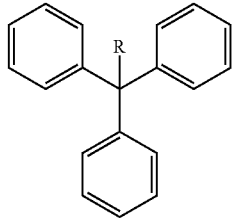
(A')

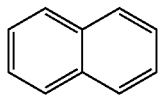
(B')

(C')

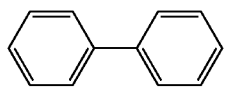
(D')

(E')

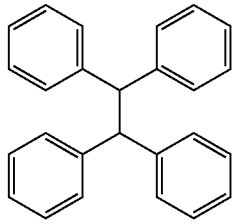
(F')

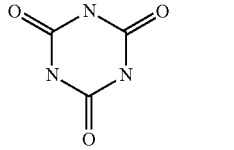
(G')

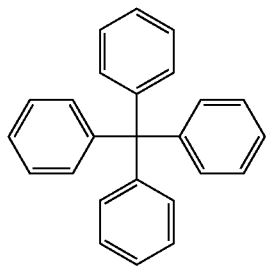

(H')

(I')

(J')

(K')

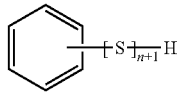

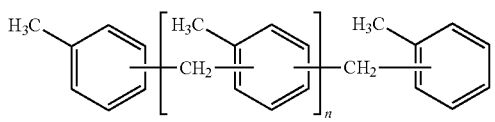
(L')

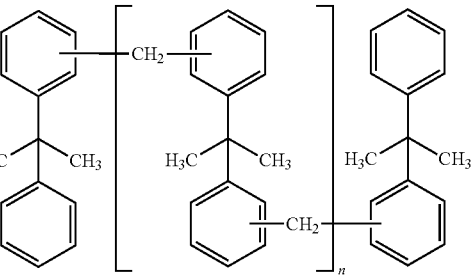
(M')

and

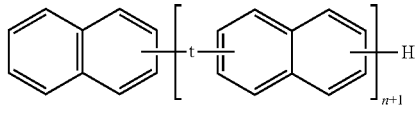
(N')

In Formula D', -p- is —C(CH$_3$)$_2$—, —CH$_2$—, —C(CF$_3$)$_2$—, —S—, —SO$_2$—,

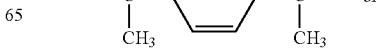 or

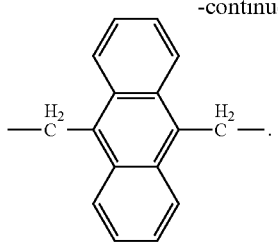

In Formula E', -q- is —CH$_2$— or a direct linkage.

In Formula H', R is hydrogen, a hydroxyl group, a C1-C10 alkyl group or aromatic group.

In Formula K', S is

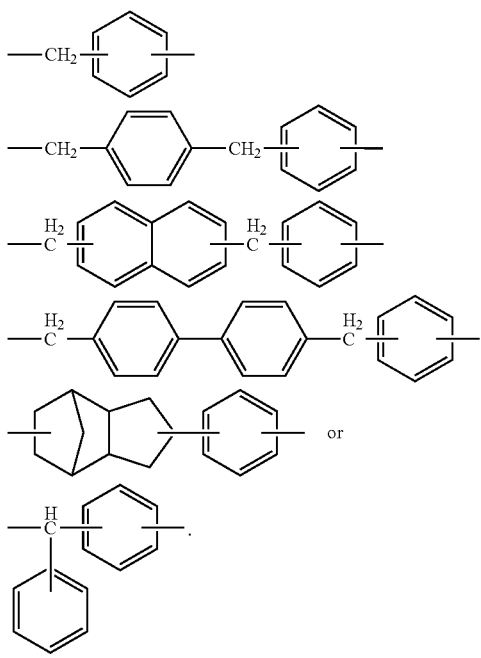

In Formula N', t is

—CH$_2$—, 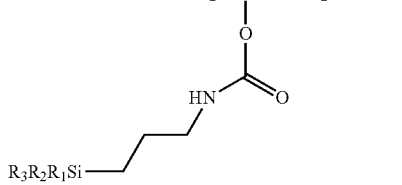

In Formulae K' to N', n is an integer equal to or greater than 1.

According to a fifth embodiment of the present invention, the epoxy compound having an alkoxysilyl group of the fourth embodiment, in which the cores selected from the group consisting of Formulae A' to I' are connected via a linking moiety of [Formula 5(2)] selected from the group consisting of Formulae LG1 to LG21, and the cores of Formula J' are connected via Formulae LG2, LG9 or LG16, may be provided.

[Formulae 5(2)]

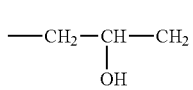 (LG1)

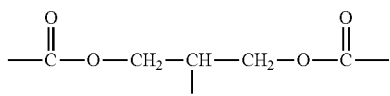 (LG2)

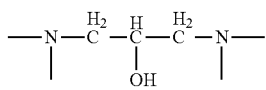 (LG3)

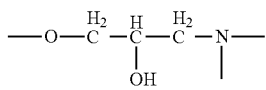 (LG4)

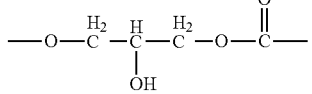 (LG5)

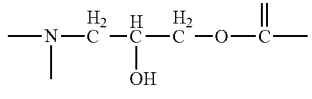 (LG6)

(LG7)

(LG8)

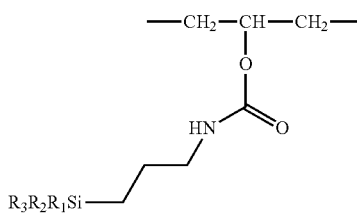 (LG9)

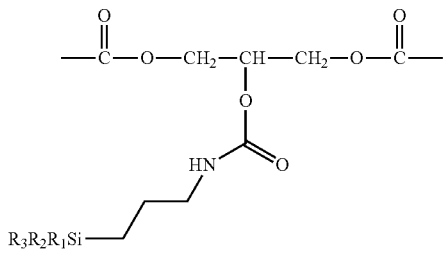 (LG10)

In Formulae LG8 to LG21, at least one of $R_1$ to $R_3$ is an alkoxy group having 1 to 5 carbon atoms, and the remainder is alkyl groups having 1 to 10 carbon atoms.

According to a sixth embodiment of the present invention, the epoxy compound having an alkoxysilyl group of the fifth embodiment, in which the epoxy compound having an alkoxysilyl group further includes an S3 substituent selected from the group consisting of Formulae S31 to S35, may be provided.

-continued

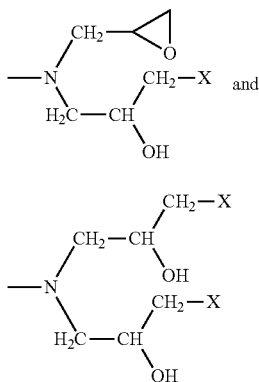
(S34)

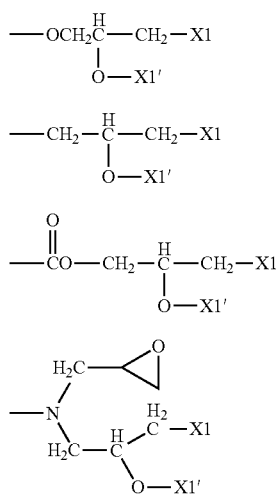
(S35)

In Formulae S31 to S35, X is $OR_4$, OH, $NR_4R_5$ or $SR_4$, and $R_4$ or $R_5$ may be an alkyl group, an alkenyl group, an aryl group or an aralkyl group having 1 to 20 carbon atoms and may include a hetero atom including N, O, P or S.

According to a seventh embodiment of the present invention, there is provided a method of preparing an epoxy compound having an alkoxysilyl group having an epoxy group and at least one alkoxysilyl group of a substituent S1 independently selected from the group consisting of Formulae S11 to S15 in a core, comprising a $1^{st}$ step of preparing an Intermediate 1 by reacting an epoxy compound having at least three epoxy groups as a starting material with one of an alcohol ($R_4$OH), an amine ($R_4R_5$NH) an a thiol ($R_4$SH) in the presence of a base and an optional solvent, or the epoxy compound with water in the presence of an acid or a base, and an optional solvent; and a 2-$1^{st}$ step of reacting the Intermediate 1 with Formula B1 in the presence of a base catalyst and an optional solvent.

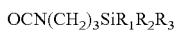 [Formula B1]

In Formula B1, at least one of $R_1$ to $R_3$ is an alkoxy group having 1 to 5 carbon atoms, and the remainder are alkyl groups having 1 to 10 carbon atoms.

[Formula S1]

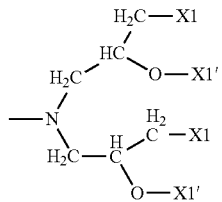
(S11)
(S12)
(S13)
(S14)

(S15)

In Formulae S11 to S15, X1 is $OR_4$, OH, $NR_4R_5$, $SR_4$ or $OCONH(CH_2)_3SiR_1R_2R_3$, X1' is H or $CONH(CH_2)_3SiR_1R_2R_3$, at least one of $R_1$ to $R_3$ is an alkoxy group having 1 to 5 carbon atoms, and the remainder are alkyl groups having 1 to 10 carbon atoms, and $R_4$ or $R_5$ may be an alkyl group, an alkenyl group, an aryl group or an aralkyl group having 1 to 20 carbon atoms and may include a hetero atom including N, O, P or S.

According to an eighth embodiment of the present invention, there is provided a method of preparing an epoxy compound having an alkoxysilyl group having an epoxy group and at least one alkoxysilyl group of a substituent S2 independently selected from the group consisting of Formulae S21 to S25 in a core, comprising a $1^{st}$ step of preparing the Intermediate 1 by reacting an epoxy compound having at least three epoxy groups as a starting material with one of an alcohol ($R_4$OH), an amine ($R_4R_5$NH) an a thiol ($R_4$SH) in the presence of a base and an optional solvent, or the epoxy compound with water in the presence of an acid or a base, and an optional solvent; a 2-$2^{nd}$ step of preparing an Intermediate 2 by reacting the Intermediate 1 with an alkenyl compound of Formula B3 in the presence of a base and an optional solvent; and a 2-$3^{rd}$ step of reacting the Intermediate 2 with Formula B2 in the presence of a metal catalyst and an optional solvent.

$HSiR_1R_2R_3$ [Formula B2]

In Formula B2, at least one of $R_1$ to $R_3$ is an alkoxy group having 1 to 5 carbon atoms, and the remainder are alkyl groups having 1 to 10 carbon atoms.

$CH_2=CH-(CH_2)_n-M$ [Formula B3]

In Formula B3, M is Cl, Br, I, $-O-SO_2-CH_3$, $-O-SO_2-CF_3$, $-O-SO_2-C_6H_4-CH$ or $-O-SO_2-C_6H_4-NO_2$, and n is 1 to 10.

[Formula S2]

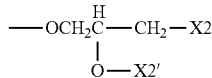
(S21)

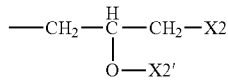
(S22)

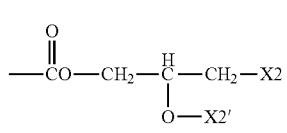
(S23)

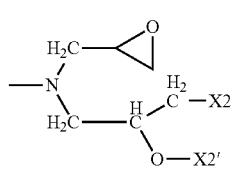
(S24)

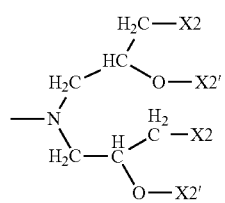
(S25)

In Formulae S21 to S25, X2 is $OR_4$, OH, $NR_4R_5$, $SR_4$ or $O(CH_2)_nCH_2CH_2SiR_1R_2R_3$, X2' is H or $(CH_2)_n CH_2CH_2SiR_1R_2R_3$, at least one of $R_1$ to $R_3$ is an alkoxy group having 1 to 5 carbon atoms, and the remainder are alkyl groups having 1 to 10 carbon atoms, and $R_4$ or $R_5$ may be an alkyl group, an alkenyl group, an aryl group or an aralkyl group having 1 to 20 carbon atoms and may include a hetero atom including N, O, P or S.

According to the ninth embodiment, the method of preparing an epoxy compound having an alkoxysilyl group of the seventh or eighth embodiment, in which the epoxy compound having at least three epoxy groups as the starting material includes one core selected from the group consisting of Formulae A' to N' and at least three epoxy groups of S4(1) selected from the group consisting of Formulae S41 to S44, wherein the cores of Formulae A' to I' are additionally connected via a linking moiety of Formula 5(1) selected from the group consisting of Formulae LG1 to LG7, and the cores of Formula J' are additionally connected via a linking moiety of Formula LG2, may be provided.

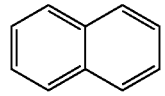
(A')

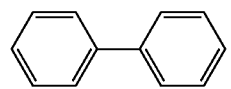
(B')

(C')

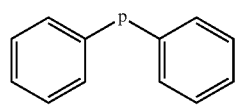
(D')

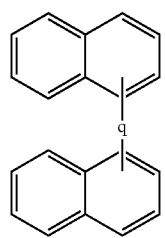
(E')

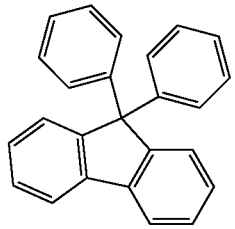
(F')

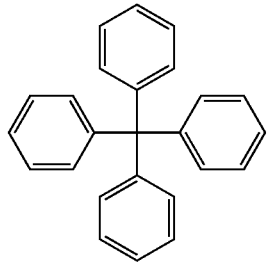
(G')

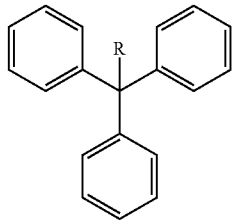
(H')

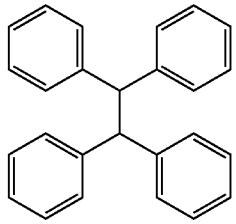
(I')

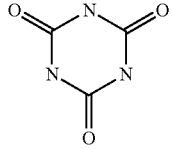
(J')

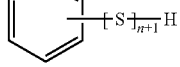
(K')

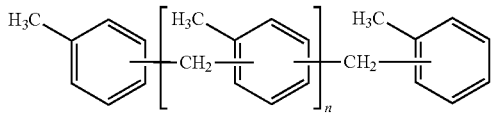
(L')

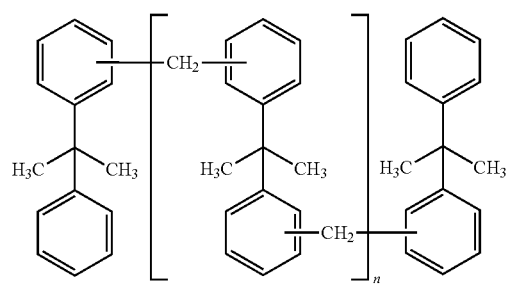 (M')
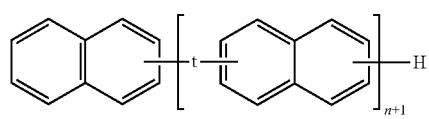 (N')
In Formula D', -p- is —C(CH$_3$)$_2$—, —CH$_2$—, —C(CF$_3$)$_2$—, —S—, —SO$_2$—,
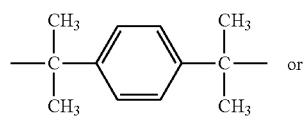 or
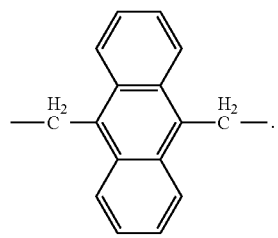
In Formula E', -q- is —CH$_2$— or a direct linkage.
In Formula H', R is hydrogen, a hydroxyl group, a C1-C10 alkyl group or aromatic group.
In Formula K', S is
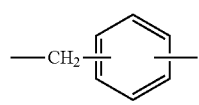
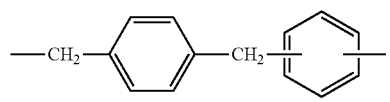
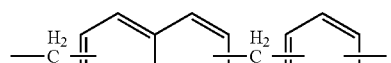
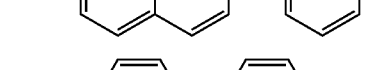
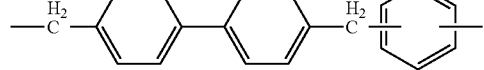 or
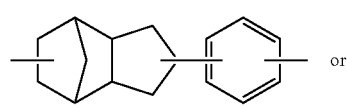
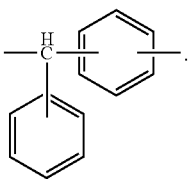
In Formula N', t is
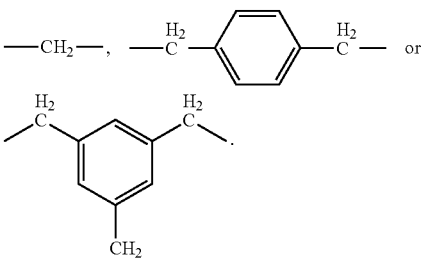
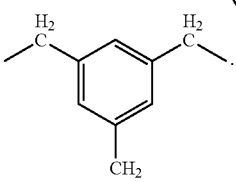
In Formulae K' to N', n is an integer equal to or greater than 1,
[Formula S4(1)]
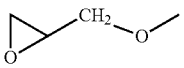 (S41)
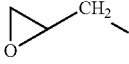 (S42)
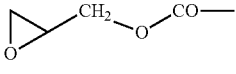 (S43)
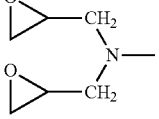 (S44)
[Formula 5(1)]
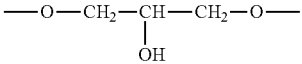 (LG1)
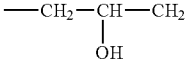 (LG2)
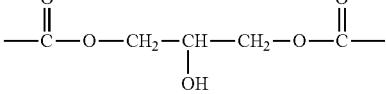 (LG3)
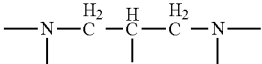 (LG4)
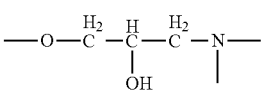 (LG5)

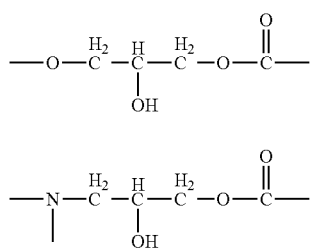

According to the tenth embodiment, the method of preparing an epoxy compound having an alkoxysilyl group of the seventh or eighth embodiment, in which the Intermediate 1 obtained in the $1^{st}$ step includes a core selected from the group consisting of Formulae A' to N', at least one epoxy group of S4(2) selected from the group consisting of Formulae S41 to S46 and at least one S3 substituent selected from the group consisting of Formulae S31 to S35, wherein the cores of Formulae A' to I' are additionally connected via a linking moiety of Formula 5(1) selected from the group consisting of Formulae LG1 to LG7, and the cores of Formula J' are additionally connected via a linking moiety of Formula LG2, may be provided.

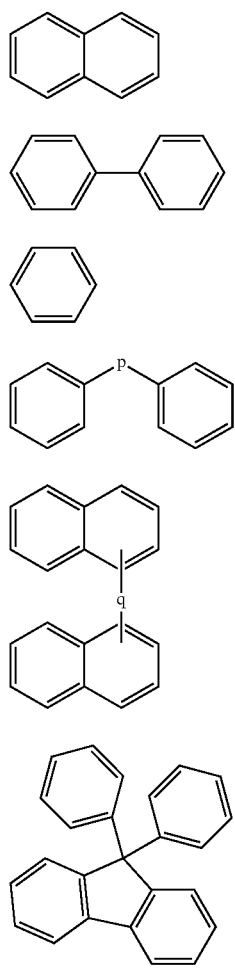

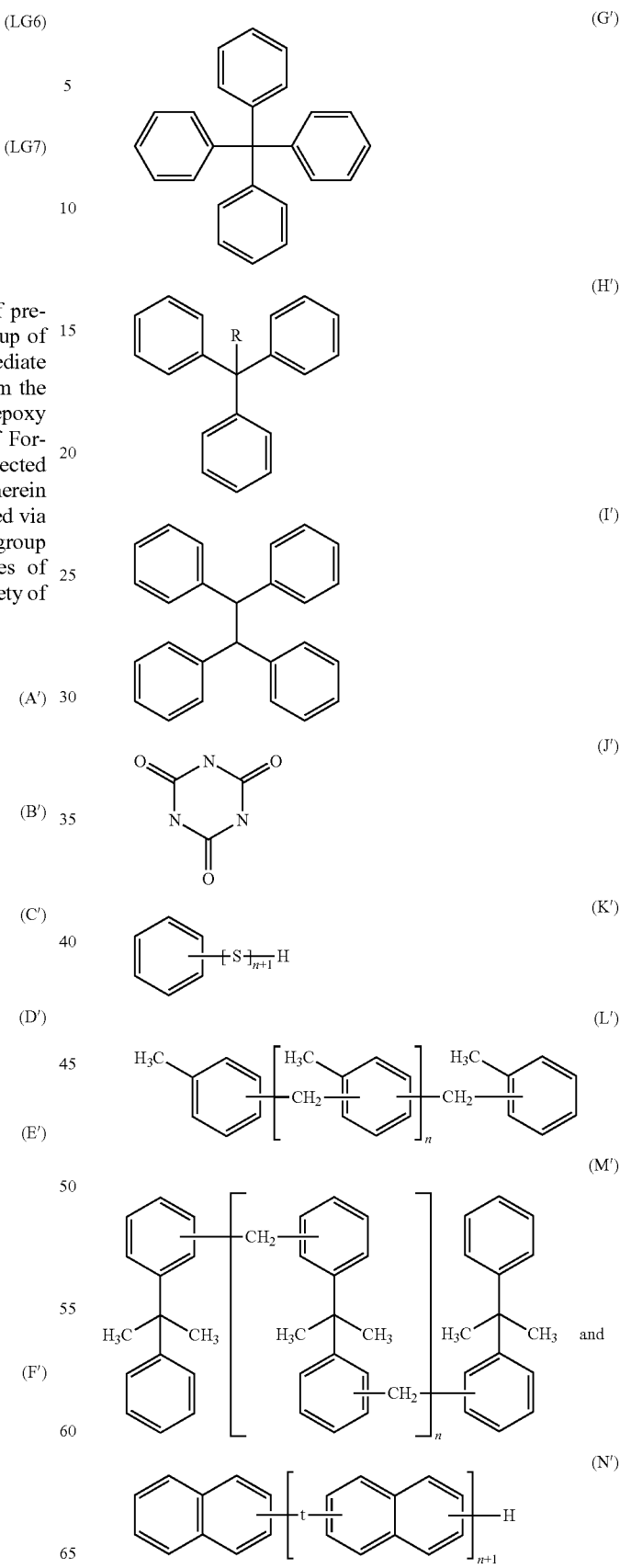

In Formula D', -p- is —C(CH$_3$)$_2$—, —CH$_2$—, —C(CF$_3$)$_2$—, —S—, —SO$_2$—,

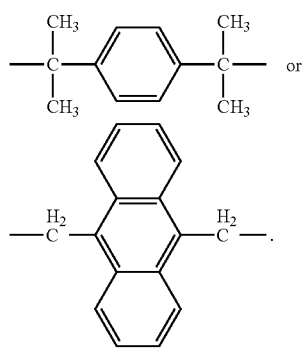

In Formula E', -q- is —CH$_2$— or a direct linkage.

In Formula H', R is hydrogen, a hydroxyl group, a C1-C10 alkyl group or aromatic group.

In Formula K', S is

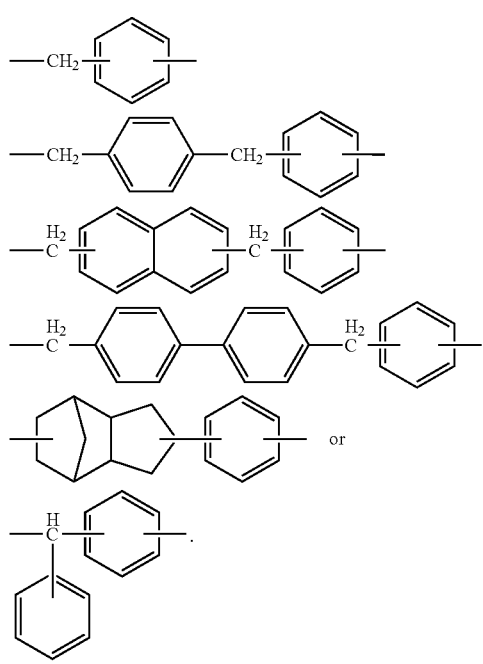

In Formula N', t is

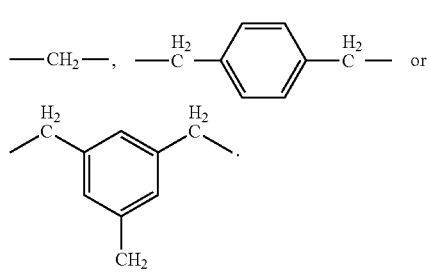

In Formulae K' to N', n is an integer equal to or greater than 1.

[Formula S3]

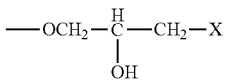 (S31)

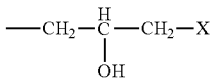 (S32)

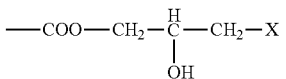 (S33)

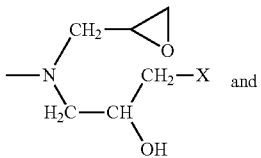 (S34)

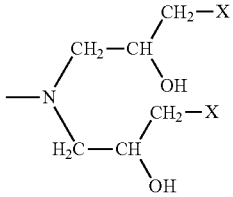 (S35)

In Formulae S31 to S35, X is OR$_4$, OH, NR$_4$R$_5$ or SR$_4$, and R$_4$ or R$_5$ may be an alkyl group, an alkenyl group, an aryl group or an aralkyl group having 1 to 20 carbon atoms and may include a hetero atom including N, O, P or S.

[Formula S4(2)]

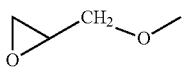 (S41)

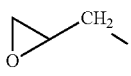 (S42)

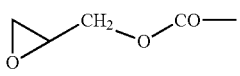 (S43)

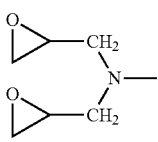 (S44)

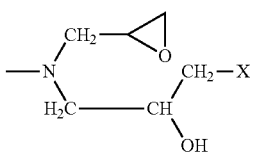 (S45)

In Formulae S41 to S45, X is OR$_4$, OH, NR$_4$R$_5$ or SR$_4$, and R$_4$ or R$_5$ may be an alkyl group, an alkenyl group, an aryl group or an aralkyl group having 1 to 20 carbon atoms and may include a hetero atom including N, O, P or S.

[Formula 5 (1)]

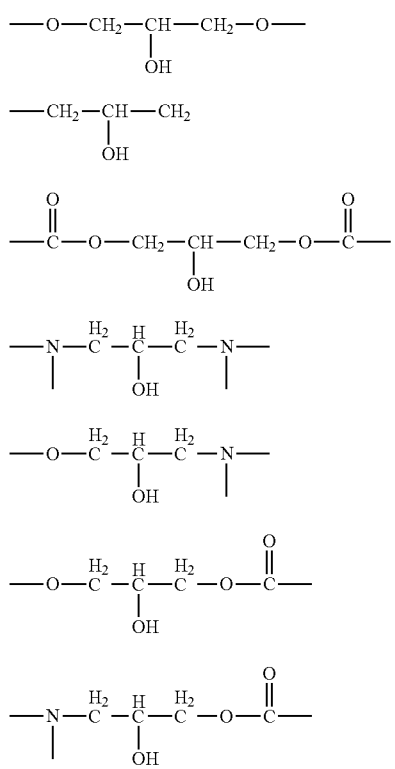

(LG1)
(LG2)
(LG3)
(LG4)
(LG5)
(LG6)
(LG7)

According to the eleventh embodiment, the method of preparing an epoxy compound having an alkoxysilyl group of the seventh or eighth embodiment, in which the epoxy compound having an alkoxysilyl group obtained in the 2-1$^{st}$ step or 2-3$^{rd}$ step includes a core selected from the group consisting of Formulae A' to N', at least one alkoxysilyl group of an S1 substituent independently selected from the group consisting of S11 to S15 or an S2 substituent independently selected from the group consisting of S21 to S25, at least one epoxy group of S4(3) selected from the group consisting of S41 to S45 and an optional substituent selected from the group consisting of S31 to S35, wherein the cores of Formulae A' to I' are additionally connected via a linking moiety selected from the group consisting of Formulae LG1 to LG21, and the cores of Formula J' are additionally connected via a linking moiety of LG2, LG9 or LG16, may be provided.

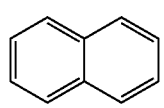
(A')

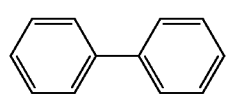
(B')

(C')

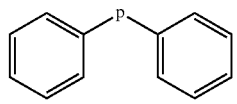
(D')

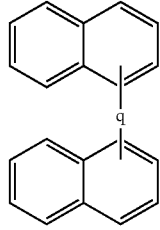
(E')

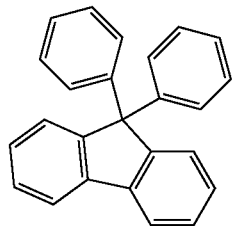
(F')

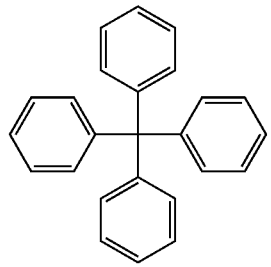
(G')

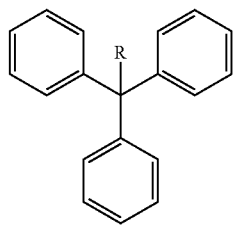
(H')

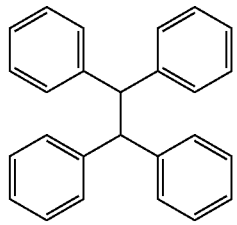
(I')

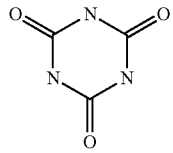
(J')

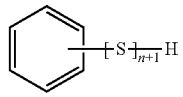
(K')

-continued

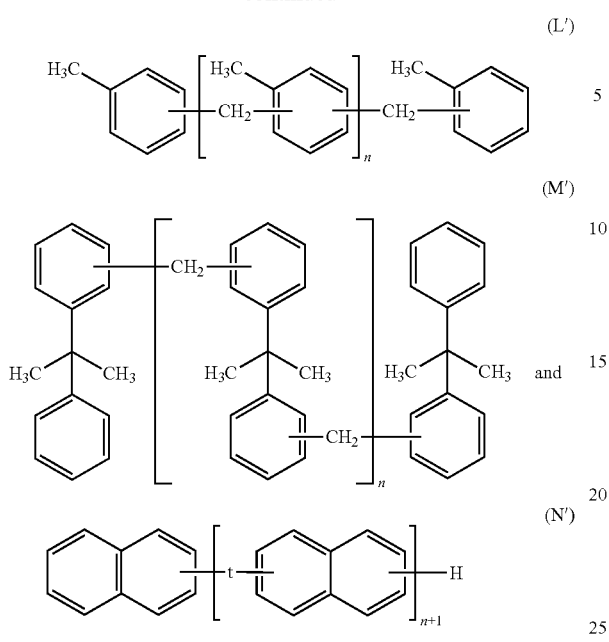

(L')

(M')

(N')

In Formula D', -p- is —C(CH$_3$)$_2$—, —CH$_2$—, —C(CF$_3$)$_2$—, —S—, —SO$_2$—,

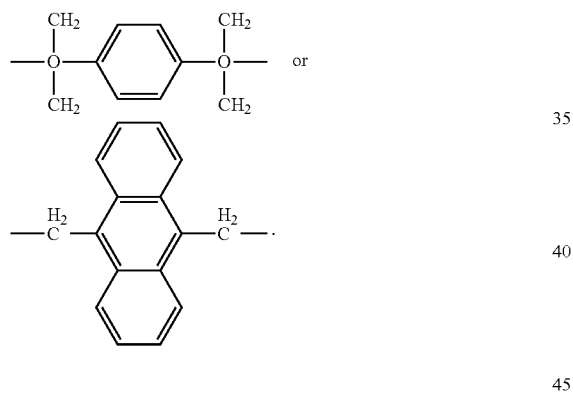

or

In Formula E', -q- is —CH$_2$— or a direct linkage.

In Formula H', R is hydrogen, a hydroxyl group, a C1-C10 alkyl group or aromatic group.

In Formula K', S is

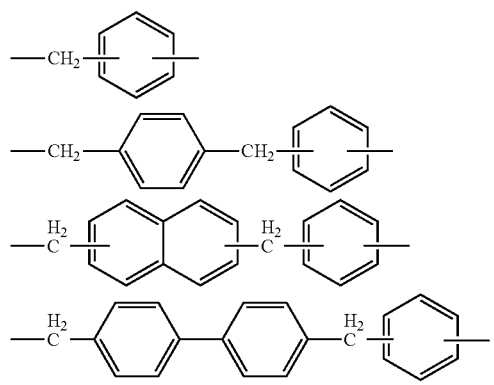

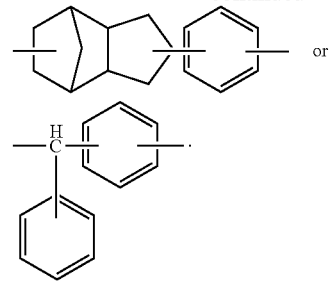

or

In Formula N', t is

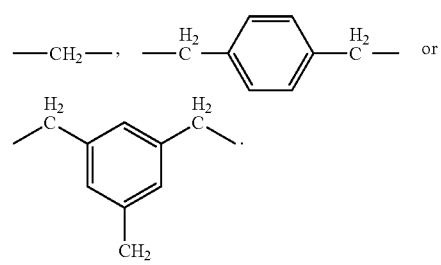

In Formulae K' to N', n is an integer equal to or greater than 1.

[Formula S1]

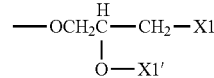 (S11)

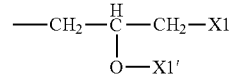 (S12)

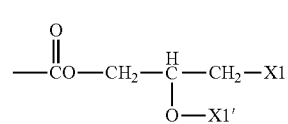 (S13)

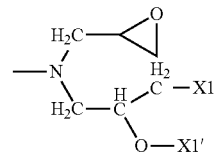 (S14)

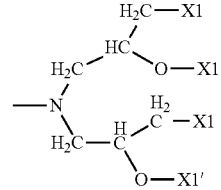 (S15)

In Formulae S11 to S15, X1 is OR$_4$, OH, NR$_4$R$_5$, SR$_4$ or OCONH(CH$_2$)$_3$SiR$_1$R$_2$R$_3$, X1' is H or CONH(CH$_2$)$_3$SiR$_1$R$_2$R$_3$, at least one of R$_1$ to R$_3$ is an alkoxy group having 1 to 5 carbon atoms, and the remainder are alkyl groups having 1 to 10 carbon atoms, and R$_4$ or R$_5$, may be an alkyl group, an alkenyl group, an aryl group or an aralkyl group having 1 to 20 carbon atoms and may include a hetero atom including N, O, P or S.

[Formula S2]

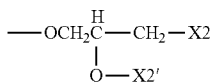 (S21)

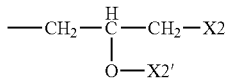 (S22)

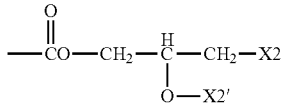 (S23)

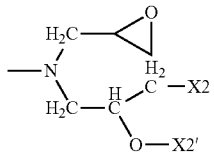 (S24)

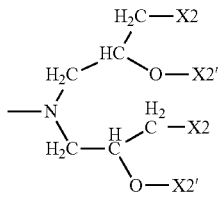 (S25)

In Formulae S21 to S25, X2 is $OR_4$, OH, $NR_4R_5$, $SR_4$ or $O(CH_2)_nCH_2CH_2SiR_1R_2R_3$, X2' is H or $(CH_2)_nCH_2CH_2SiR_1R_2R_3$, at least one of $R_1$ to $R_3$ is an alkoxy group having 1 to 5 carbon atoms, and the remainder are an alkyl group having 1 to 10 carbon atoms, and $R_4$ or $R_5$ may be an alkyl group, an alkenyl group, an aryl group or an aralkyl group having 1 to 20 carbon atoms and may include a hetero atom including N, O, P or S.

[Formula S3]

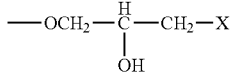 (S31)

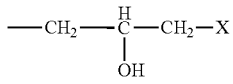 (S32)

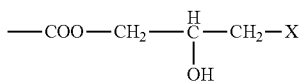 (S33)

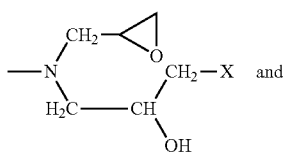 (S34)

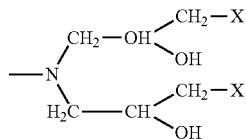 (S35)

In Formulae S31 to S35, X is $OR_4$, OH, $NR_4R_5$ or $SR_4$, and $R_4$ or $R_5$ may be an alkyl group, an alkenyl group, an aryl group or an aralkyl group having 1 to 20 carbon atoms and may include a hetero atom including N, O, P or S.

[Formula S4(3)]

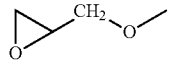 (S41)

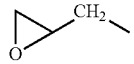 (S42)

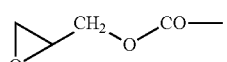 (S43)

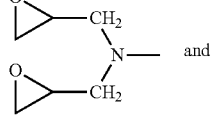 (S44)

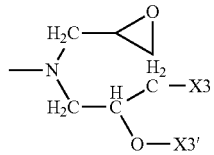 (S45)

In the formula (S45), X3 is $OR_4$, OH, $NR_4R_5$, $SR_4$, $OCONH(CH_2)_3SiR_1R_2R_3$ or $O(CH_2)_nCH_2CH_2SiR_1R_2R_3$, X3' is H, $CONH(CH_2)_3SiR_1R_2R_3$ or $(CH_2)_nCH_2CH_2SiR_1R_2R_3$, at least one of $R_1$ to $R_3$ is an alkoxy group having 1 to 5 carbon atoms, and the remainder are alkyl groups having 1 to 10 carbon atoms, and $R_4$ or $R_5$ may be an alkyl group, an alkenyl group, an aryl group or an aralkyl group having 1 to 20 carbon atoms and may include a hetero atom including N, O, P or S.

[Formula 5(2)]

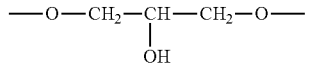 (LG1)

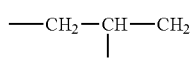 (LG2)

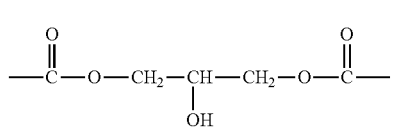 (LG3)

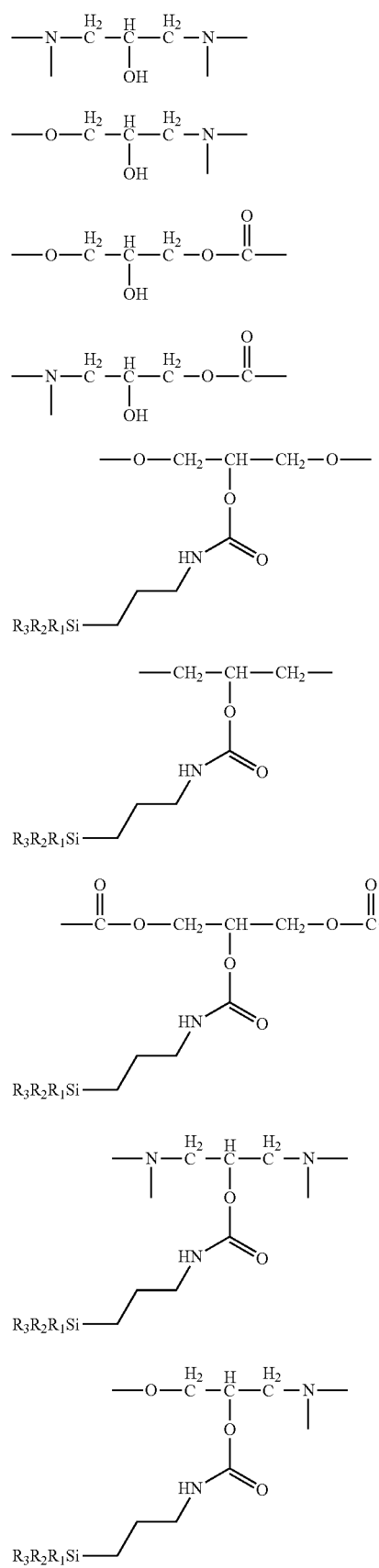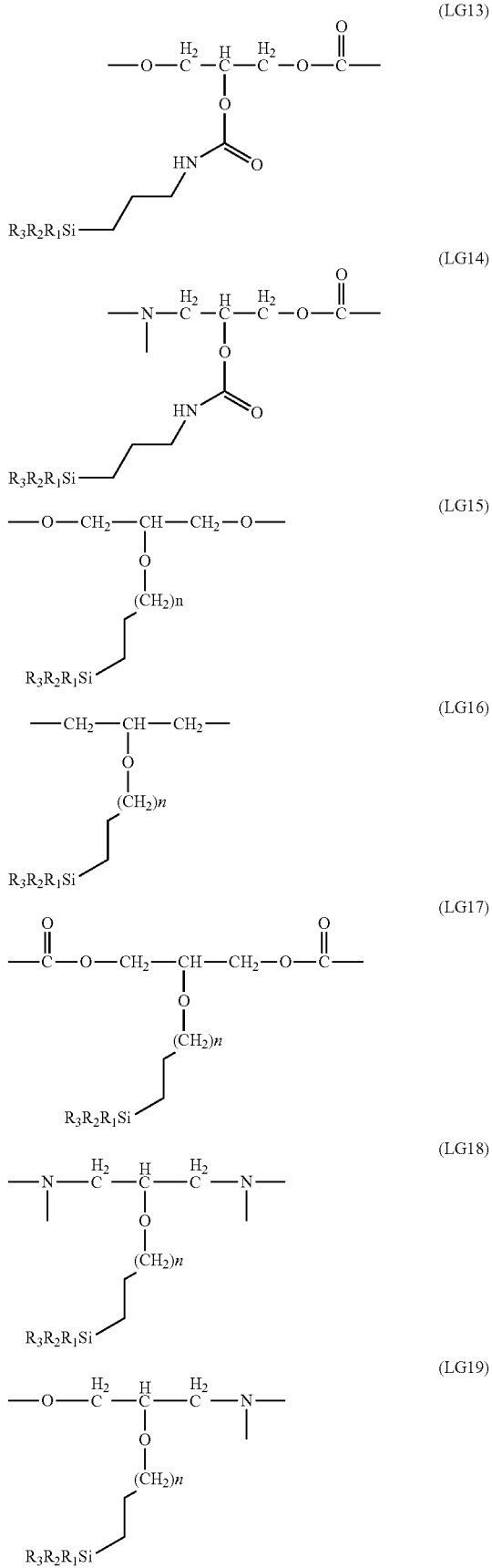

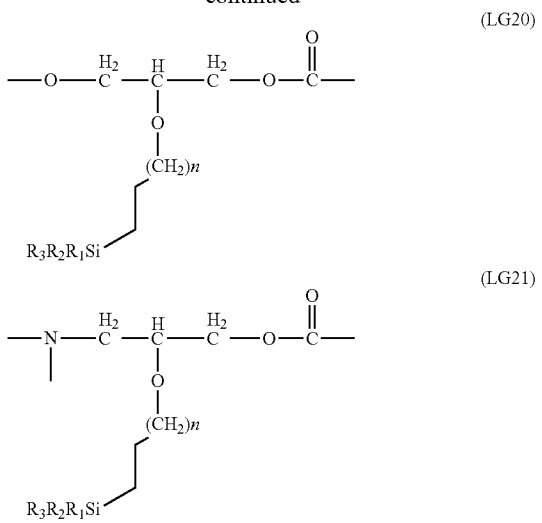

In Formulae LG8 to LG21, at least one of $R_1$ to $R_3$ is an alkoxy group having 1 to 5 carbon atoms, and the remainder are alkyl groups having 1 to 10 carbon atoms.

According to the twelfth embodiment, the method of preparing an epoxy compound having an alkoxysilyl group of the seventh or eighth embodiment, in which 0.1 to 20 equivalents of the alcohol ($R_4OH$) and the water and 0.1 to 10 equivalents of the amine and the thiol react on the basis of 1 equivalent of the epoxy group of the starting material in the $1^{st}$ step, may be provided.

According to the thirteenth embodiment, the method of preparing an epoxy compound having an alkoxysilyl group of the seventh or eighth embodiment, in which the $1^{st}$ step is conducted at a temperature within a range of room temperature to 200° C. for 10 minutes to 120 hours, may be provided.

According to the fourteenth embodiment, the method of preparing an epoxy compound having an alkoxysilyl group of the seventh embodiment, in which 0.1 to 12 equivalents of an alkoxysilane of Formula B1 react on the basis of 1 equivalent of a hydroxyl group of the Intermediate 1 in the $2\text{-}1^{st}$ step, may be provided.

According to the fifteenth embodiment, the method of preparing an epoxy compound having an alkoxysilyl group of the eighth embodiment, in which 0.1 to 10 equivalents of an alkenyl group of an alkenyl compound of Formula B3 react on the basis of 1 equivalent of a hydroxyl group of the Intermediate 1 in the $2\text{-}2^{nd}$ step, may be provided.

According to the sixteenth embodiment, the method of preparing an epoxy compound having an alkoxysilyl group of the eighth embodiment, in which 0.1 to 12 equivalents of an alkoxysilane of Formula B2 react on the basis of 1 equivalent of an alkenyl group of the Intermediate 2 in the $2\text{-}3^{rd}$ step, may be provided.

According to the seventeenth embodiment, the method of preparing an epoxy compound having an alkoxysilyl group of the seventh embodiment, in which the $2\text{-}1^{st}$ step is conducted at a temperature within a range of room temperature to 150° C. for 10 minutes to 120 hours, may be provided.

According to the eighteenth embodiment, the method of preparing an epoxy compound having an alkoxysilyl group of the eighth embodiment, in which the $2\text{-}2^{nd}$ step is conducted at a temperature within a range of room temperature to 100° C. for 10 minutes to 120 hours, may be provided.

According to the nineteenth embodiment, the method of preparing an epoxy compound having an alkoxysilyl group of the eighth embodiment, in which the $2\text{-}3^{rd}$ step is conducted at a temperature within a range of room temperature to 120° C. for 10 minutes to 120 hours, may be provided.

According to the twentieth embodiment, in the present invention there is provided an epoxy composition comprising the epoxy compound having an alkoxysilyl group according to any one of the first to sixth embodiments and a curing agent.

According to the twenty-first embodiment, the epoxy composition of the twentieth embodiment, in which at least one epoxy compound selected from the group consisting of a glycidyl ether-based, a glycidyl-based, a glycidylamine-based and a glycidyl ester-based epoxy compound is further comprised, may be provided.

According to the twenty-second embodiment, the epoxy composition of the twenty-first embodiment, in which the epoxy compound further comprised is at least one selected from the group consisting of a bisphenol-based, a biphenyl-based, a naphthalene-based, a benzene-based, a thiodiphenol-based, a fluorene-based, an anthracene-based, an isocyanurate-based, a triphenylmethane-based, a 1,1,2,2-tetraphenylethane-based, a tetraphenylmethane-based, a 4,4'-diaminodiphenylmethane-based, an aminophenol-based, an alicyclic, an aliphatic and a novolac epoxy compound, may be provided.

According to the twenty-third embodiment, the epoxy composition of the twentieth embodiment, in which a curing accelerator is further comprised, may be provided.

According to the twenty-fourth embodiment, the epoxy composition of the twentieth embodiment, in which at least one filler selected from the group consisting of a fiber and inorganic particles is further comprised, may be provided.

According to the twenty-fifth embodiment, the epoxy composition of the twenty-fourth embodiment, in which the inorganic particle is at least one selected from the group consisting of at least one metal oxide selected from the group consisting of silica, zirconia, titania and alumina, silicon nitride, aluminum nitride and silsesquioxane, may be provided.

According to the twenty-sixth embodiment, the epoxy composition of the twenty-fourth embodiment, in which the inorganic particle is comprised in a range of 5 wt % to 95 wt % on the basis of the total amount of the solid content of the epoxy composition, may be provided.

According to the twenty-seventh embodiment, the epoxy composition of the twenty-fourth embodiment, in which the fiber is at least one selected from the group consisting of glass fiber selected from the group consisting of an E-glass fiber, a T-glass fiber, an S-glass fiber, an NE-glass fiber, an H-glass fiber and quartz, and at least one organic fiber selected from the group consisting of a liquid crystal polyester fiber, a polyethyleneterephthalate fiber, a wholly aromatic fiber, a polybenzoxasol fiber, a nylon fiber, a polyethylene naphthalate fiber, a polypropylene fiber, a polyether sulfone fiber, a polyvinylidene fluoride fiber, a polyethylene sulfide fiber and a polyether ether ether ketone fiber, may be provided.

According to the twenty-eighth embodiment, the epoxy composition of the twenty-fourth embodiment, in which the fiber is comprised in a range of 10 wt % to 90 wt % on the basis of the total weight of the solid content of the epoxy composition, may be provided.

According to the twenty-ninth embodiment, the epoxy composition of the twenty-fourth embodiment, in which when the fiber is comprised, the inorganic particles are further comprised, may be provided.

According to the thirtieth embodiment, the epoxy composition of the twentieth embodiment, in which at least one reaction catalyst of an alkoxysilyl group selected from the group consisting of an inorganic acid selected from the group consisting of nitric acid, sulfuric acid, hydrochloric acid, acetic acid and phosphoric acid, ammonia, KOH, $NH_4OH$, an amine, a transition metal alkoxide and a tin compound is further comprised, may be provided.

According to the thirty-first embodiment, the epoxy composition of the thirtieth embodiment, in which the reaction catalyst is used in an amount range of 0.01 phr to 10 phr on the basis of the epoxy resin having an alkoxysilyl group, may be provided.

According to the thirty-second embodiment, the epoxy composition of the thirtieth embodiment, in which water is further comprised, may be provided.

According to the thirty-third embodiment, the epoxy composition of the thirty-second embodiment, in which 0.01 to 20 equivalents of water are comprised on the basis of 1 equivalent of the alkoxysilyl group, may be provided.

According to the thirty-fourth embodiment, in the present invention there is provided an electronic material comprising the epoxy composition of the twentieth embodiment.

According to the thirty-fifth embodiment, in the present invention there is provided a substrate comprising the epoxy composition of the twentieth embodiment.

According to the thirty-sixth embodiment, in the present invention there is provided a film comprising the epoxy composition of the twentieth embodiment.

According to the thirty-seventh embodiment, in the present invention there is provided a prepreg comprising the epoxy composition of the twentieth embodiment.

According to the thirty-eighth embodiment, in the present invention there is provided a laminate including a metal layer formed on the prepreg of the thirty-seventh embodiment.

According to the thirty-ninth embodiment, in the present invention there is provided a printed circuit board including the prepreg of the thirty-seventh embodiment.

According to the fortieth embodiment, in the present invention there is provided a semiconductor apparatus including a semiconductor device installed on the printed circuit board of the thirty-ninth embodiment.

According to the forty-first embodiment, in the present invention there is provided a semiconductor packaging material comprising the epoxy composition of the twentieth embodiment.

According to the forty-second embodiment, in the present invention there is provided a semiconductor device including the semiconductor packaging material of the forty-first embodiment.

According to the forty-third embodiment, in the present invention there is provided an adhesive comprising the epoxy composition of the twentieth embodiment.

According to the forty-fourth embodiment, in the present invention there is provided a paint comprising the epoxy composition of the twentieth embodiment.

According to the forty-fifth embodiment, in the present invention there is provided a composite material comprising the epoxy composition of the twentieth embodiment.

According to the forty-sixth embodiment, in the present invention there is provided a cured product of the epoxy composition of the twentieth embodiment.

According to the forty-seventh embodiment, the cured product of the forty-sixth embodiment, in which the cured product having a coefficient of thermal expansion (CTE) of less than or equal to 60 ppm/° C., may be provided.

According to the forty-eighth embodiment, the cured product of the forty-sixth embodiment, in which the cured product having a glass transition temperature of 100° C. or above, or does not exhibiting the glass transition temperature, may be provided.

Advantageous Effects

According to the embodiments of the present invention, due to chemical bonding between an alkoxysilyl group in the epoxy compound and a filler, a composite of the epoxy composition comprising a novel epoxy compound having an alkoxysilyl group may have improved effects. That is, the CTE of an epoxy composite may be decreased, and a glass transition temperature may be increased or the glass transition temperature may not be exhibited (Tg-less). In addition, the cured product comprising the epoxy compound of the present invention may exhibit good flame retardancy.

Further, in the case that the epoxy composition according to the present invention is applied to a metal film of a substrate, good adhesive properties may be exhibited with respect to the metal film due to the chemical bonding between the functional group at the surface of the metal film and the alkoxysilyl group. In addition, due to the increase in chemical bonding efficiency of the composition comprising the epoxy compound having an alkoxysilyl group, a silane coupling agent used in a common epoxy composition may be unnecessary in the composition comprising the epoxy compound having an alkoxysilyl group. The epoxy composition comprising the epoxy compound may have good curing efficiency (including thermal curing and/or photo curing), and a composite formed through the curing thereof may exhibit good thermal expansion properties such as a low CTE and a high glass transition temperature or Tg-less properties.

Best Mode

Exemplary embodiments of the present invention will now be described. The embodiments of the present invention may however be modified in various modes, and the scope of the present invention is not limited to the following embodiments. In addition, the exemplary embodiments are provided to explain the present invention further completely for a person having an average knowledge in this technical field.

The present invention provides a novel epoxy compound having an alkoxysilyl group, the composite thereof exhibits improved heat resistance properties, particularly, a low CTE and high Tg or Tg-less, and/or the cured product thereof exhibits good flame retardancy, a method of preparing the same, an epoxy composition comprising the same, a cured product thereof and a use thereof.

In the present invention, "composite" refers to a cured product formed using a composition comprising an epoxy compound and an inorganic material as a filler (fiber and/or inorganic particles). In the present invention, "cured product" refers to a cured product formed using a composition comprising an epoxy compound, in detail, refers to a cured product formed using a composition comprising any epoxy compound, for example comprising an epoxy compound; a curing agent; and at least one selected from the group consisting of an optional inorganic material (filler), an optional curing catalyst and other additives. In addition, the term "cured product" is also used to denote a "partially-cured product".

When forming a composite through curing the epoxy composition comprising the epoxy compound having an alkoxysilyl group in accordance with the present invention, an epoxy group may react with a curing agent to conduct a curing reaction, and the alkoxysilyl group may form an interface bond with the surface of the filler. Thus, very high chemical bonding efficiency in an epoxy composite system may be obtained, and thus, a low CTE and high glass transition temperature increasing effect may be achieved. Therefore, dimensional stability may be improved. In addition, the cured product comprising the epoxy compound of the present invention exhibits good flame retardancy.

Further, when applying the epoxy composition of the present invention to a chemically processed metal film such as a copper film, a chemical bond may be formed with a —OH group or the like on the surface of the metal produced through the metal surface treatment, thereby exhibiting good adhesiveness with respect to the metal film.

1. Epoxy Compound

According to an embodiment of the present invention, an epoxy compound having an alkoxysilyl group, including an epoxy group and at least one alkoxysilyl group of an S1 substituent independently selected from the group consisting of Formulae S11 to S15 or an S2 substituent independently selected from the group consisting of Formulae S21 to S25 in a core, is provided.

[Formula S1]

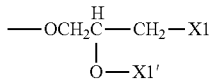 (S11)

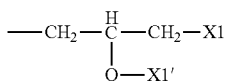 (S12)

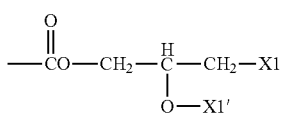 (S13)

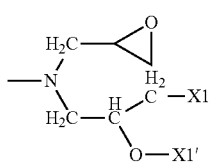 (S14)

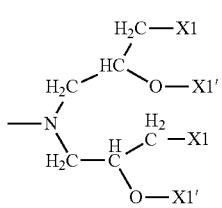 (S15)

in Formulae S11 to S15, X1 is $OR_4$, OH, $NR_4R_5$, $SR_4$ or $OCONH(CH_2)_3SiR_1R_2R_3$, X1' is H or $CONH(CH_2)_3SiR_1R_2R_3$, at least one of $R_1$ to $R_3$ is an alkoxy group having 1 to 5 carbon atoms, and the remainder are alkyl groups having 1 to 10 carbon atoms, and $R_4$ or $R_5$ may be an alkyl group, an alkenyl group, an aryl group or an aralkyl group having 1 to 20 carbon atoms and may include a hetero atom including N, O, P or S.

[Formula S2]

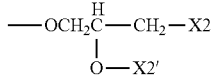 (S21)

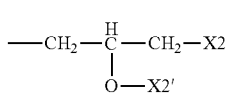 (S22)

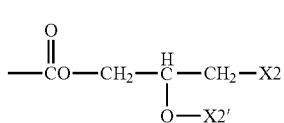 (S23)

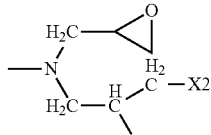 (S24)

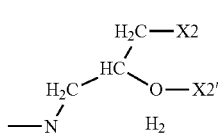 (S25)

in Formulae S21 to S25, X2 is $OR_4$, OH, $NR_4R_5$, $SR_4$ or $O(CH_2)_nCH_2CH_2SiR_1R_2R_3$, X2' is H or $(CH_2)_n CH_2CH_2SiR_1R_2R_3$, at least one of $R_1$ to $R_3$ is an alkoxy group having 1 to 5 carbon atoms, and the remainder are alkyl groups having 1 to 10 carbon atoms, and $R_4$ or $R_5$ may be an alkyl group, an alkenyl group, an aryl group or an aralkyl group having 1 to 20 carbon atoms and may include a hetero atom including N, O, P or S.

In the alkoxysilylated epoxy compound according to an embodiment of the present invention, the epoxy group may have an epoxy group of Formula S4(3) selected from the group consisting of Formulae S41 to S45.

[Formula S4(3)]

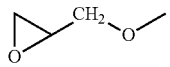 (S41)

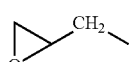 (S42)

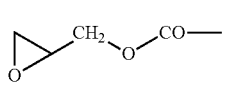 (S43)

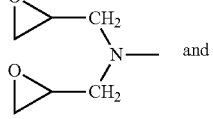 (S44)

and

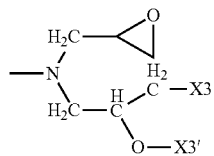

(S45)

in formula S45, where X3 is OR$_4$, OH, NR$_4$R$_5$, SR$_4$, OCONH(CH$_2$)$_3$SiR$_1$R$_2$R$_3$ or O(CH$_2$)$_n$CH$_2$CH$_2$SiR$_1$R$_2$R$_3$, X3' is H, CONH(CH$_2$)$_3$SiR$_1$R$_2$R$_3$ or (CH$_2$)$_n$CH$_2$CH$_2$SiR$_1$R$_2$R$_3$, at least one of R$_1$ to R$_3$ is an alkoxy group having 1 to 5 carbon atoms, and the remainder are alkyl groups having 1 to 10 carbon atoms, and R$_4$ or R$_5$ may be an alkyl group, an alkenyl group, an aryl group or an aralkyl group having 1 to 20 carbon atoms and may include a hetero atom including N, O, P or S.

The alkoxysilylated epoxy compound may be a compound having a bisphenol, a biphenyl, a naphthalene, a benzene, a thiodiphenol, a fluorene, an anthracene, an isocyanurate, a triphenylmethane, a 1,1,2,2-tetraphenylethane, a tetraphenylmethane, a 4,4'-diaminodiphenylmethane, an aminophenol, an aliphatic, an aromatic or a novolac unit as a core structure.

Further, the core in the alkoxysilylated epoxy compound may be one selected from the group consisting of Formulae A' to N'.

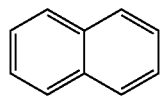
(A')

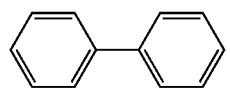
(B')

(C')

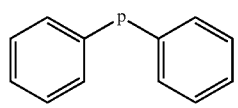
(D')

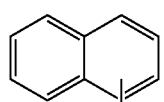
(E')

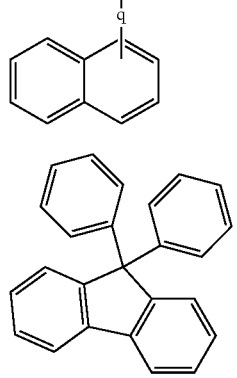
(F')

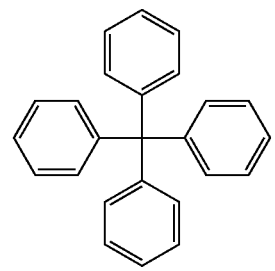
(G')

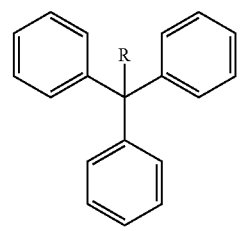
(H')

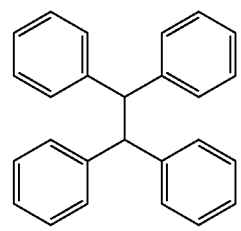
(I')

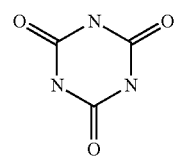
(J')

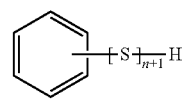
(K')

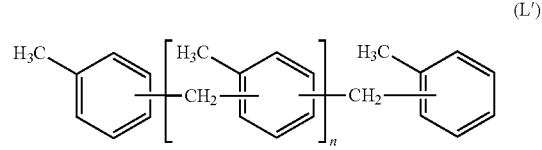
(L')

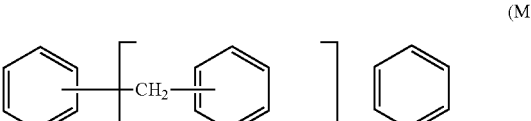
(M')

and

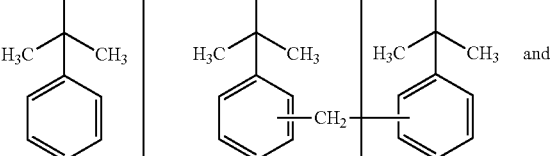

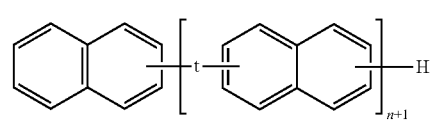
(N')

In Formula D', -p- is —C(CH$_3$)$_2$—, —CH$_2$—, —C(CF$_3$)$_2$—, —S—, —SO$_2$—,

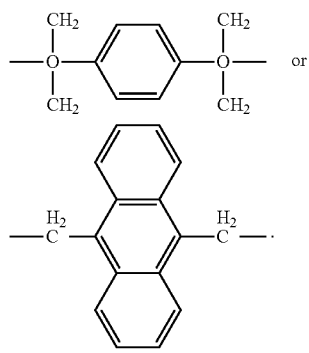

or

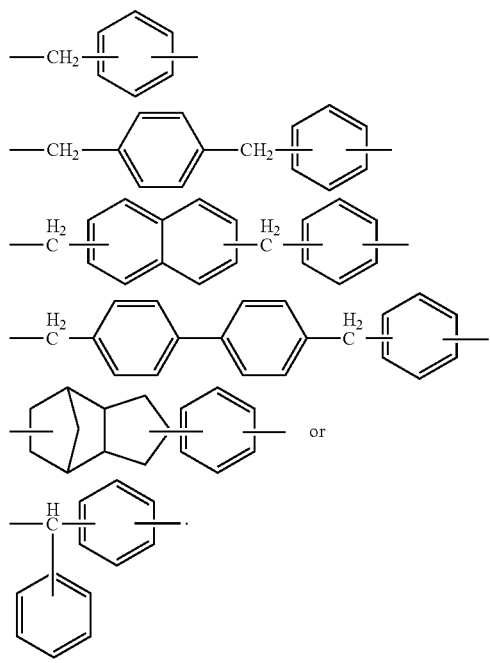

In Formula E', -q- is —CH$_2$— or a direct linkage.

In Formula H', R is hydrogen, a hydroxyl group, a C1-C10 alkyl group or aromatic group.

In Formula K', S is

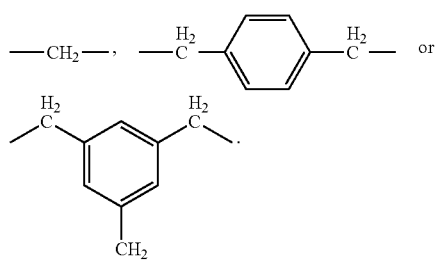

In Formula N', t is

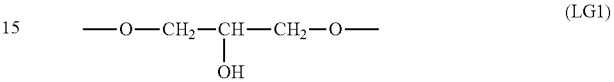

in Formulae K' to N', n is an integer equal to or greater than 1.

Further, in the alkoxysilylated epoxy compound, the cores may be connected via a linking moiety of [Formula 5(2)] selected from the group consisting of Formulae LG1 to LG21. 1 to 1,000 cores may further be connected as occasion demands. Particularly, the cores of Formulae A' to I' may be connected via a linking moiety LG of [Formula 5(2)] selected from the group consisting of LG1 to LG21, and the cores of Formula J' may be connected via Formula LG2, LG9 or LG16.

[Formula 5(2)]

 (LG1)

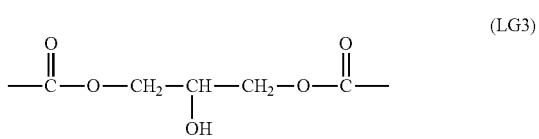 (LG2)

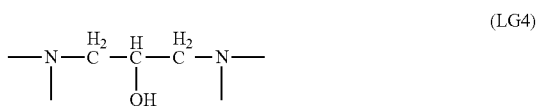 (LG3)

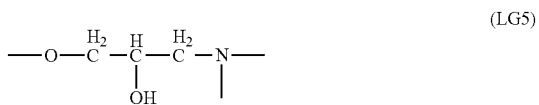 (LG4)

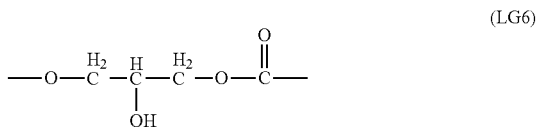 (LG5)

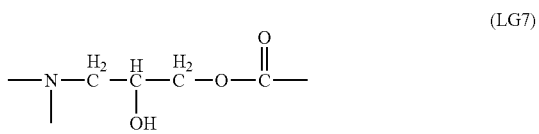 (LG6)

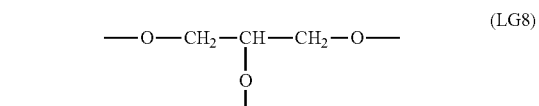 (LG7)

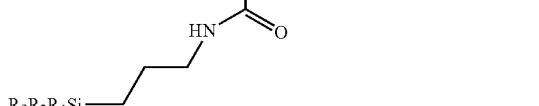 (LG8)

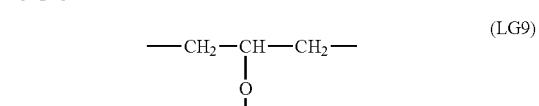 (LG9)

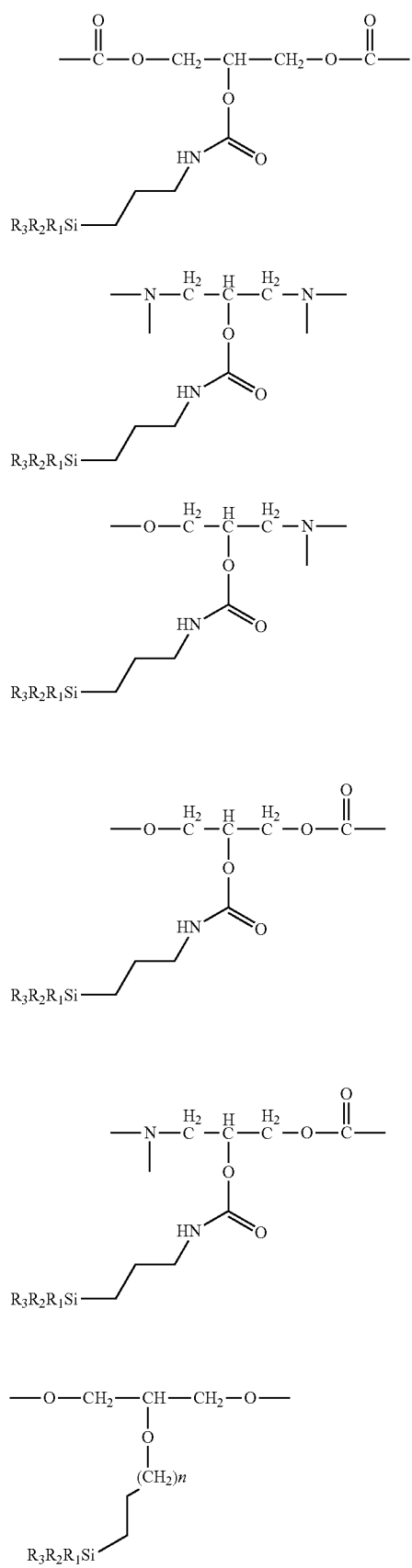
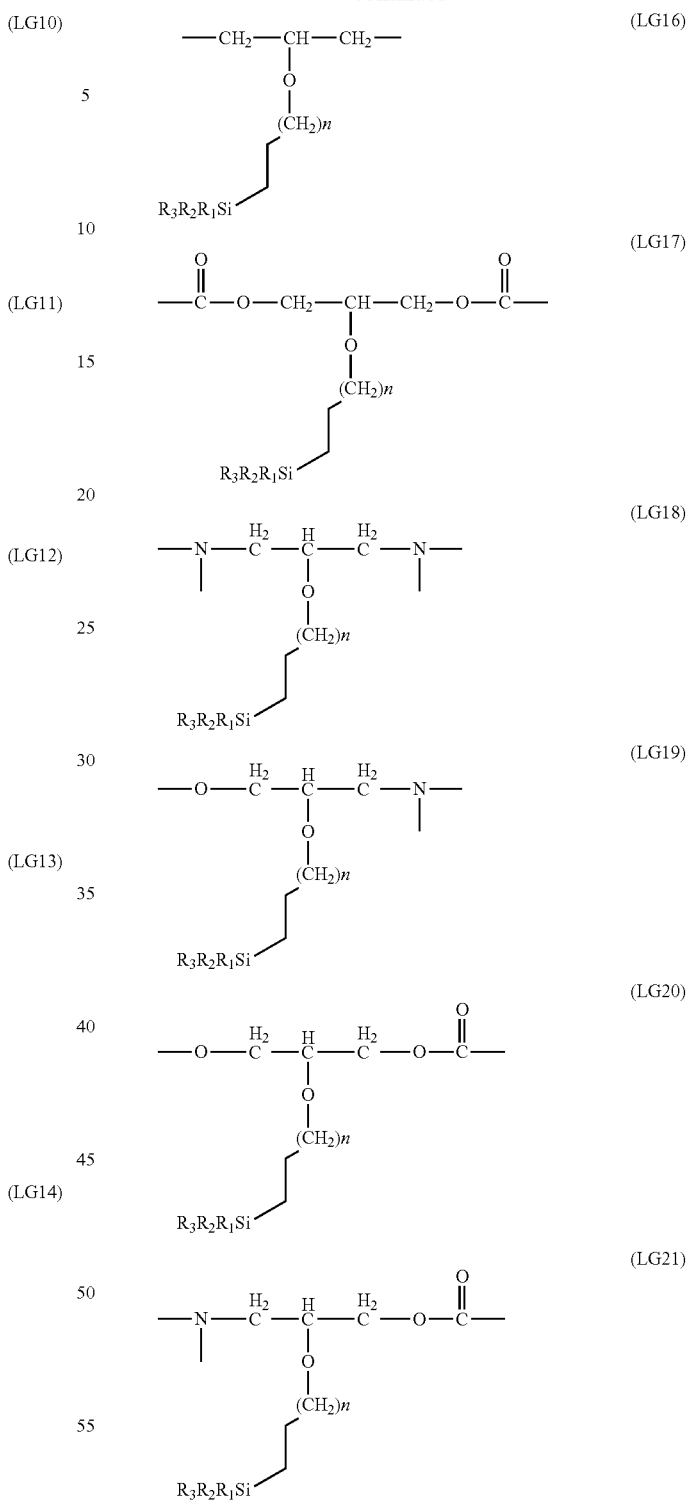
In Formulae LG8 to LG21, at least one of $R_1$ to $R_3$ is an alkoxy group having 1 to 5 carbon atoms, and the remainder are alkyl groups having 1 to 10 carbon atoms.
Further, the epoxy compound having an alkoxysilyl group of the present invention may further include an S3 substituent selected from the group consisting of Formulae S31 to S35.

[Formula S3]

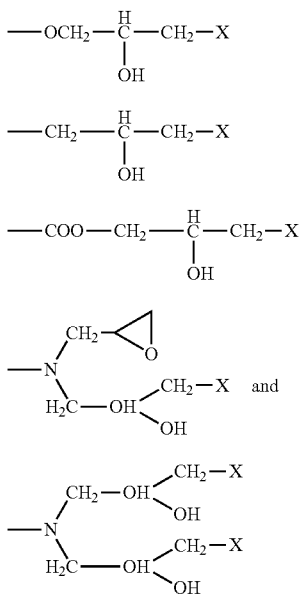

In Formulae S31 to S35, X is $OR_4$, OH, $NR_4R_5$ or $SR_4$, and $R_4$ or $R_5$ may be an alkyl group, an alkenyl group, an aryl group or an aralkyl group having 1 to 20 carbon atoms and may include a hetero atom including N, O, P or S.

Particularly, for example, in the case that the core is the naphthalene core of Formula A', the epoxy compound according to an embodiment of the present invention may be represented by Formula AI, and in the case that the core is the biphenyl core of Formula B', the epoxy compound according to an embodiment of the present invention may be represented by Formula BI. Hereinafter, particular examples of the naphthalene core and the biphenyl core will be described, and a person skilled in this technical field may easily understand the structure of the alkoxysilylated epoxy compound according to the present invention, connected by a linking moiety and having an epoxy group, an alkoxysilyl group, etc. in other cores. In addition, it would be obvious in this technical field that the epoxy compound of the present invention may include a polymer including a dimer, a trimer, etc. other than a monomer of the epoxy compound.

[Formula AI]

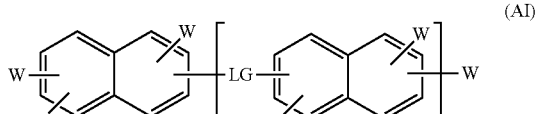

[Formula BI]

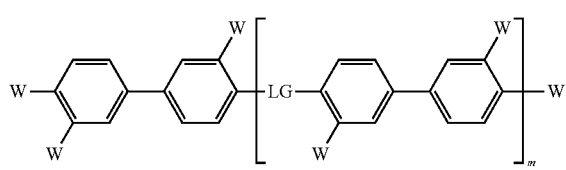

In Formulae AI and BI, at least one of a plurality of W is an alkoxysilyl group of an S1 substituent independently selected from the group consisting of Formulae S11 to S15 or an S2 substituent independently selected from the group consisting of Formulae S21 to S25, and the remainder are an S4(3) substituent independently selected from the group consisting of Formulae S41 to S45 so that the compound may include at least one epoxy group, and the remainder other than S1, S2 and S4(3) may be independently selected from the group consisting of H and an S3 substituent independently selected from the group consisting of Formulae S31 to S35. LG may be selected from the group consisting of Formulae LG1 to LG21, and m is an integer from 0 to 1,000.

2. Method of Preparing Epoxy Compound

The alkoxysilylated epoxy compound according to an embodiment of the present invention may be prepared by an epoxy ring-opening reaction and alkoxysilylation through the reaction of an epoxy functional group with a nucleophile such as an alcohol ($R_4OH$), water, an amine ($R_4R_5NH$) and a thiol ($R_4SH$). Thus, according to an embodiment of the present invention, a method of preparing an alkoxysilylated epoxy compound comprising an epoxy ring-opening reaction ($1^{st}$ step) through the reaction of an epoxy compound having at least three epoxy groups as a starting material with one of an alcohol ($R_4OH$), water, an amine ($R_4R_5NH$) and a thiol ($R_4SH$), and an alkoxysilylation ($2\text{-}1^{st}$ step to $2\text{-}3^{rd}$ step) is provided.

In the $1^{st}$ step, the Intermediate 1 in which the epoxy group of an epoxy compound is ring-opened is obtained by the reaction of an epoxy compound having at least three epoxy groups as a starting material with one of an alcohol ($R_4OH$), water, an amine ($R_4R_5NH$) and a thiol ($R_4SH$).

In the $1^{st}$ step, the epoxy compound having at least three epoxy groups as a starting material reacts with one of an alcohol ($R_4OH$), water, an amine ($R_4R_5NH$) and a thiol ($R_4SH$) in the presence of a base and an optional solvent, or the epoxy compound reacts with water in the presence of an acid or base, and an optional solvent. In this case, 0.1 to 20 equivalents of the alcohol ($R_4OH$) and water or 0.1 to 10 equivalents of the amine ($R_4R_5NH$) and the thiol ($R_4SH$) may react on the basis of 1 equivalent of the epoxy group of the starting material.

The starting material is the epoxy compound having at least three epoxy groups and may be any epoxy compound commonly known. For example, the epoxy compound may be a glycidyl ether type, a glycidyl type, a glycidyl amine type or a glycidyl ester type epoxy compound having at least three epoxy groups. More particularly, the epoxy compound may be an epoxy compound having at least three epoxy groups and a core including a bisphenol, a biphenyl, a naphthalene, a benzene, a thiodiphenol, a fluorene, an anthracene, an isocyanurate, a triphenylmethane, a 1,1,2,2-tetraphenylethane, a tetraphenylmethane, a 4,4'-diaminodiphenylmethane, an aminophenol, an alicyclic, an aliphatic or a novolac unit.

More particularly, the epoxy compound having at least three epoxy groups as the starting material may include a core selected from the group consisting of Formulae A' to N' and at least three epoxy groups of S4(1) selected from the group consisting of Formulae S41 to S44. Further, the cores of Formulae A' to I' may be additionally connected via a linking moiety of [Formula 5(1)] selected from the group consisting of Formulae LG1 to LG7 and the cores of Formula J' may be additionally connected via LG2. 1 to 1,000 cores may be additionally connected via the linking moiety.

The reaction temperature and the reaction time of the 1st step reaction may change according to the kind of reactants; however, the Intermediate 1 in which the epoxy group of the epoxy compound as the starting material is ring-opened by conducting a reaction, for example, at a temperature within a range of room temperature (for example, from 15° C. to 25° C.) to 200° C. for 10 minutes to 120 hours. Here, the reaction may be assisted by adding an ammonium halide within a range of a catalytic amount to 5 equivalents per an epoxy reacting group. The ammonium halide may be for example, Et$_4$NI, Et$_4$NBr, Et$_4$NCl, Bu$_4$NI, Bu$_4$Br or Bu$_4$NCl, without limitation.

The base used may include, for example, KOH, NaOH, K$_2$CO$_3$, Na$_2$CO$_3$, KHCO$_3$, NaHCO$_3$ and NaH, without limitation. These bases may be used alone or as a combination of two or more thereof. $1 \times 10^{-2}$ to 5 equivalents of the base may be used per 1 equivalent of the epoxy group of the starting material in consideration of reaction efficiency. In addition, the acid used for the reaction of the epoxy compound having at least three epoxy groups as the starting material with water may include, for example, HCl, HBr, HI, HClO$_4$ and CH$_3$COOH, without limitation.

The acid may be used alone or as a combination of two or more thereof. $1 \times 10^{-2}$ to 5 equivalents of the acid may be used per 1 equivalent of the epoxy group of the starting material in consideration of reaction efficiency.

The solvent may be used optionally during the reaction in the 1st step, as occasion demands. For example, the solvent may not be used if the viscosity of the reactants at the reaction temperature is appropriate for carrying out the reaction without using an additional solvent in the 1st step reaction. That is, an additional solvent is unnecessary in the case in which the viscosity of the reactants is sufficiently low, and the mixing and stirring of the reactants may be easily performed without solvents. This may be easily determined by a person skilled in the art. In the case in which a solvent is used, any organic solvent may be used, if they are able to dissolve the reactants properly, not having any adverse influence on the reaction, and being easily removed after the reaction. For example, acetonitrile, tetrahydrofuran (THF), methyl ethyl ketone (MEK), dimethylformamide (DMF), dimethyl sulfoxide (DMSO), methylene chloride (MC), or the like, may be used, without specific limitation. These solvents may be used alone or as a mixture of two or more thereof. The amount of the solvent may not be limited to being within a specific range, and an appropriate amount of the solvent may be used within a range sufficient for sufficiently dissolving the reactants and not adversely affecting the reaction. A person skilled in the art may select an appropriate amount of the solvent in consideration of the above-mentioned points.

The Intermediate 1 may be a glycidyl ether type, a glycidyl type, a glycidyl amine type or a glycidyl ester type epoxy compound having at least one epoxy group of S4(2) selected from the group consisting of Formulae S41 to S45 and at least one S3 substituent selected from the group consisting of Formulae S31 to S35. More particularly, the Intermediate 1 may be an epoxy compound having at least one epoxy group of S4(2) selected from the group consisting of Formulae S41 to S45 and at least one S3 substituent selected from the group consisting of Formulae S31 to S35, and having a bisphenol, a biphenyl, a naphthalene, a benzene, a thiodiphenol, a fluorene, an anthracene, an isocyanurate, a triphenylmethane, a 1,1,2,2-tetraphenylethane, a tetraphenylmethane, a 4,4'-diaminodiphenylmethane, an aminophenol, an alicyclic, an aliphatic, or a novolac unit as a core.

The epoxy compound having at least three epoxy groups may react with one of an alcohol (R$_4$OH), an amine (R$_4$R$_5$NH) and a thiol (R$_4$SH) in the presence of a base and an optional solvent, or the epoxy compound may react with water in the presence of an acid or base, and an optional solvent. In this case, 0.1 to 20 equivalents of the alcohol (R$_4$OH) and the water and 0.1 to 10 equivalents of the amine (R$_4$R$_5$NH) and the thiol (R$_4$SH) may react on the bases of 1 equivalent of the epoxy group of the starting material.

[Formula S3]

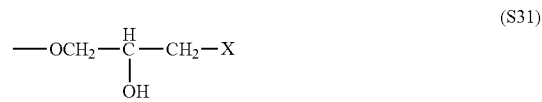
(S31)

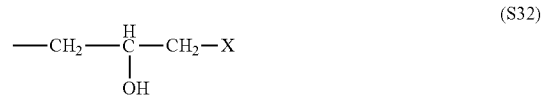
(S32)

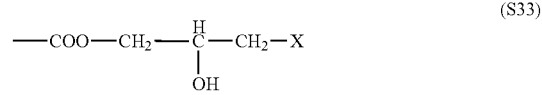
(S33)

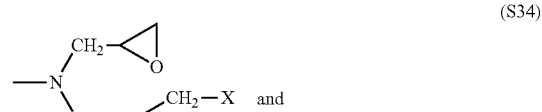
(S34)

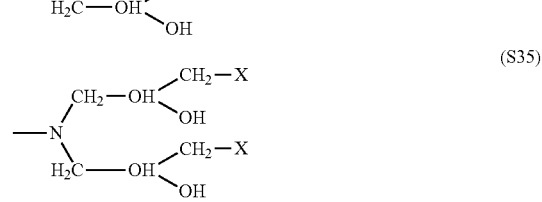
(S35)

In Formulae S31 to S35, X is OR$_4$, OH, NR$_4$R$_5$ or SR$_4$, and R$_4$ or R$_5$ may be an alkyl group, an alkenyl group, an aryl group or an aralkyl group having 1 to 20 carbon atoms and may include a hetero atom including N, O, P or S.

[Formula S4(1)]

(S41)

(S42)

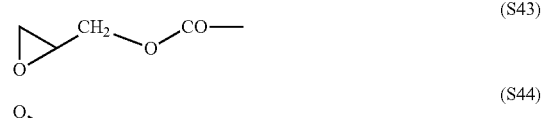
(S43)

(S44)

[Formula S4(2)]

(S41)

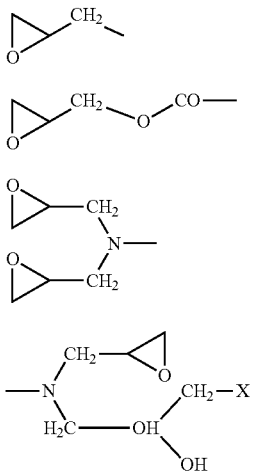

(S42)

(S43)

(S44)

(S45)

In Formula S45, X is $OR_4$, OH, $NR_4R_5$ or $SR_4$, and $R_4$ or $R_5$ may be an alkyl group, an alkenyl group, an aryl group or an aralkyl group having 1 to 20 carbon atoms and may include a hetero atom including N, O, P or S.

More particularly, the Intermediate 1 includes a core selected from the group consisting of Formulae A' to N', at least one epoxy group of S4(2) selected from the group consisting of S41 to S45, and at least one S3 substituent selected from the group consisting of Formulae S31 to S35, and the cores of Formulae A' to I' may be additionally connected via a linking moiety of [Formula 5(1)] selected from the group consisting of LG1 to LG7 and the cores of Formula J' may be additionally connected via a linking moiety of LG2.

In the 2-1$^{st}$ step, the Intermediate 1 obtained in the 1$^{st}$ step is silylated by the reaction with Formula B1 to produce an epoxy compound having in a core an epoxy group and at least one alkoxysilyl group of an S1 substituent independently selected from the group consisting of Formulae S11 to S15. The product obtained in the 2-1$^{st}$ step may also correspond to a target product of an alkoxysilylated epoxy compound according to an embodiment of the present invention.

Particularly, in the reaction of the Intermediate 1 with an isocyanate alkoxysilane of Formula B1, the secondary alcohol (hydroxyl group) of the Intermediate 1 obtained in the 1$^{st}$ step may be silylated to produce an alkoxysilyl group independently selected from the group consisting of Formulae S11 to S15.

Particularly, the Intermediate 1 in which an epoxy group is ring-opened and obtained by reacting an epoxy compound having at least three epoxy groups with one of an alcohol ($R_4OH$), an amine ($R_4R_5NH$) and a thiol ($R_4SH$) in the presence of a base and an optional solvent in the 1$^{st}$ step, may include an alcohol group via the ring opening of one epoxy group. The Intermediate 1 in which an epoxy group is ring-opened and obtained by reacting an epoxy compound with water in the presence of an acid or a base, and an optional solvent, may include two alcohol groups via the ring opening of one epoxy group. Thus, the Intermediate 1 produced by the reaction of the epoxy compound with water may be additionally silylated and may have two alkoxysilyl groups via the ring opening of one epoxy group.

In the 2-1$^{st}$ step reaction, the Intermediate 1 and the alkoxysilane of Formula B1 may react according to the stoichiometric equivalent ratio. In addition, as described above, the alkoxysilane of Formula B1 may react with the secondary alcohol (hydroxyl group) of the Intermediate 1.

Thus, 0.1 to 12 equivalents of the alkoxysilane of Formula B1 may react per 1 equivalent of the hydroxyl group of the Intermediate 1 in consideration of the above-described points.

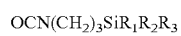  [Formula B1]

At least one of $R_1$ to $R_3$ is an alkoxy group having 1 to 5 carbon atoms, and the remainder are alkyl groups having 1 to 10 carbon atoms.

The reaction temperature and the reaction time of the 2-1$^{st}$ step reaction may change according to the kind of reactants; however, the reaction may be performed, for example, at a temperature within a range of room temperature (for example, from 15° C. to 25° C.) to 150° C. for 10 minutes to 120 hours.

The 2-1$^{st}$ step reaction may be performed in the presence of a base catalyst. The base catalyst may include, for example, $K_2C3$, $Na_2CO_3$, $KHCO_3$, $NaHCO_3$, triethylamine and diisopropylethylamine, without limitation. These bases may be used alone or as a combination of two or more thereof. $1 \times 10^{-2}$ to 5 equivalents of the base may be used per 1 equivalent of the hydroxyl group of the intermediate in consideration of reaction efficiency.

The solvent may be used optionally during the reaction of the 2-1$^{st}$ step, as occasion demands. For example, the solvent may not be used if the viscosity of the reactants at the reaction temperature is appropriate for carrying out the reaction without using an additional solvent in the 2-1$^{st}$ step. That is, an additional solvent is unnecessary in the case in which the viscosity of the reactants is sufficiently low, and the mixing and stirring of the reactants may be easily performed without solvents. This may be easily determined by a person skilled in the art. In the case in which a solvent is used, any aprotic solvent may be used, if able to dissolve the reactants properly, not having any adverse influence on the reaction, and being easily removed after the reaction. For example, toluene, acetonitrile, tetrahydrofuran (THF), methyl ethyl ketone (MEK), dimethylformamide (DMF), dimethyl sulfoxide (DMSO), methylene chloride (MC), or the like, may be used, without limitation. These solvents may be used alone or as a mixture of two or more thereof. The amount of the solvent may not be limited to being within a specific range, and an appropriate amount of the solvent may be used within a range sufficient for dissolving the reactants and not adversely affecting the reaction. A person skilled in the art may select an appropriate amount of the solvent in consideration of the above-mentioned points.

As described above, the epoxy compound obtained in the 2-1$^{st}$ step also includes an epoxy group and an alkoxysilyl group, and corresponds to an epoxy compound having an alkoxysilyl group which is a target product of the present invention. Particularly, a method of preparing an epoxy compound having an alkoxysilyl group and obtained in the 2-1$^{st}$ step, which comprises a core selected from the group consisting of Formulae A' to N', at least one alkoxysilyl group as an S1 substituent independently selected from the group consisting of Formulae S11 to S15, at least one epoxy group S4(3) selected from the group consisting of Formulae S41 to S46, and an optional substituent of Formula S3 selected from the group consisting of Formulae S31 to S35, wherein the cores of Formulae A' to I' may be additionally connected via a linking moiety selected from the group consisting of Formulae LG1 to LG14, and the cores of Formula J' may be additionally connected via a linking moiety of LG2 or LG9, may be provided.

In the 2-$2^{nd}$ step, the Intermediate 1 obtained in the 1 step may react with an alkenyl compound of Formula B3 to form an alkenylated the Intermediate 2, and in the 2-$3^{rd}$ step, the Intermediate 2 react may with Formula B2 to produce an epoxy compound having an epoxy group and at least one alkoxysilyl group of an S2 substituent independently selected from the group consisting of Formulae S21 to S25 in a core. The product obtained in the 2-$3^{rd}$ step may correspond to an alkoxysilylated epoxy compound which is a target product according to an embodiment of the present invention.

Particularly, in the 2-$2^{nd}$ step, the hydroxyl group of the intermediate may be alkenylated by the reaction of Intermediate 1 with an alkenyl compound of Formula B3, and in the 2-$3^{rd}$ step, the alkenyl group of the Intermediate 2 may be silylated by the reaction of the Intermediate 2 with an alkoxysilane of Formula B2 to form an alkoxysilyl group independently selected from the group consisting of Formulae S21 to S25.

In the 2-$2^{nd}$ step reaction, the Intermediate 1 and the alkenyl group of the alkenyl compound of Formula B3 may react according to the stoichiometric equivalent ratio. In addition, as described above, the alkenyl group of Formula B3 may react with the secondary alcohol (hydroxyl group) of the Intermediate 1.

In the 2-$3^{rd}$ step reaction, the Intermediate 2 and the alkoxysilane of Formula B2 may react according to the stoichiometric equivalent ratio. In addition, as described above, the alkoxysilane of Formula B2 may react with the alkenyl group of the Intermediate 2.

Thus, the reaction of the alkenyl group of Formula B3 with the Intermediate 1 in the 2-$2^{nd}$ step is performed so that 0.1 to 10 equivalents of the alkenyl group of the alkenyl compound of Formula B3 may be used on the basis of 1 equivalent of the hydroxyl group of the Intermediate 1. In addition, the reaction of the alkoxysilane of Formula B2 with the Intermediate 2 in the 2-$3^{rd}$ step is performed so that 0.1 to 12 equivalents of the alkoxysilane of Formula B2 may be used on the basis of 1 equivalent of the alkenyl group of the Intermediate 2.

$HSiR_1R_2R_3$ [Formula B2]

At least one of $R_1$ to $R_3$ is an alkoxy group having 1 to 5 carbon atoms, and the remainder are alkyl groups having 1 to 10 carbon atoms.

$CH_2=CH-(CH_2)_n-M$ [Formula B3]

In Formula B3, M is Cl, Br, I, $-O-SO_2-CH_3$, $-O-SO_2-CF_3$, $-O-SO_2-C_6H_4-CH_3$ or $-O-SO_2-C_6H_4-NO_2$, and n is 1 to 10.

The reaction temperature and the reaction time of the 2-$2^{nd}$ step reaction may change according to the kind of reactants; however, the reaction may be performed, for example, at a temperature within a range of room temperature (for example, from 15° C. to 25° C.) to 100° C. for 10 minutes to 120 hours. In addition, the reaction temperature and the reaction time of the 2-$3^{rd}$ step reaction may change according to the kind of reactants; however, the reaction may be performed, for example, at a temperature within a range of room temperature (for example, from 15° C. to 25° C.) to 120° C. for 10 minutes to 120 hours.

The 2-$2^{nd}$ step reaction may be performed in the presence of a base. The base used in the 2-$2^{nd}$ step reaction may include, for example, KOH, NaOH, $K_2CO_3$, $Na_2CO_3$, $KHCO_3$, $NaHCO_3$ and NaH, without limitation. These bases may be used alone or as a combination of two or more thereof. $1\times10^{-2}$ to 5 equivalents of the base may be used per 1 equivalent of the hydroxyl group of the Intermediate 1 in consideration of reaction efficiency.

The reaction of the 2-$3^{rd}$ step reaction is conducted in the presence of a metal catalyst. As the metal catalyst, for example, a platinum catalyst of $PtO_2$ or chloroplatinic acid ($H_2PtCl_6$) may be used, without limitation. $10^{-4}$ to 0.05 equivalents of the platinum catalyst per 1 equivalent of the allyl group of the Intermediate 2 may preferably be used in consideration of reaction efficiency.

The solvent may be used optionally during the reaction of the 2-$2^{nd}$ step, as occasion demands. For example, the solvent may not be used if the viscosity of the reactants at the reaction temperature is appropriate for carrying out the reaction without using an additional solvent in the 2-$2^{nd}$ step. That is, an additional solvent is unnecessary in the case in which the viscosity of the reactants is sufficiently low, and the mixing and stirring of the reactants may be easily performed without solvents. This may be easily determined by a person skilled in the art. In the case in which a solvent is used, any organic solvent may be used, if able to dissolve the reactants properly, not having any adverse influence on the reaction, and being easily removed after the reaction. For example, acetonitrile, tetrahydrofuran (THF), methyl ethyl ketone (MEK), dimethylformamide (DMF), dimethyl sulfoxide (DMSO), methylene chloride (MC), or the like, may be used, without limitation. These solvents may be used alone or as a mixture of two or more thereof. The amount of the solvent may not be limited to being within a specific range, and an appropriate amount of the solvent may be used within a range sufficient for sufficiently dissolving the reactants and not adversely affecting the reaction. A person skilled in the art may select an appropriate amount of the solvent in consideration of the above-mentioned points.

The solvent may be used optionally during the reaction of the 2-$3^{rd}$ step reaction, as occasion demands. For example, the solvent may not be used if the viscosity of the reactants at the reaction temperature is appropriate for carrying out the reaction without using an additional solvent in the 2-$3^{rd}$ step. That is, an additional solvent is unnecessary in the case in which the viscosity of the reactants is sufficiently low, and the mixing and stirring of the reactants may be easily performed without solvents. This may be easily determined by a person skilled in the art. In the case in which a solvent is used, any aprotic solvent may be used, if able to dissolve the reactants properly, not having any adverse influence on the reaction, and being easily removed after the reaction. For example, toluene, acetonitrile, tetrahydrofuran (THF), methyl ethyl ketone (MEK), dimethylformamide (DMF), dimethyl sulfoxide (DMSO), methylene chloride (MC), or the like, may be used, without limitation. These solvents may be used alone or as a mixture of two or more thereof. The amount of the solvent may not be limited to being within a specific range, and an appropriate amount of the solvent may be used within a range sufficient for sufficiently dissolving the reactants and not adversely affecting the reaction. A person skilled in the art may select an appropriate amount of the solvent in consideration of the above-mentioned points.

As described above, the epoxy compound obtained in the 2-$3^{rd}$ step also includes an epoxy group and an alkoxysilyl group and corresponds to a target product of an epoxy compound having an alkoxysily group. Particularly, a method of preparing an epoxy compound having an alkoxysilyl group and obtained in the 2-$3^{rd}$ step which comprises a core selected from the group consisting of Formulae A' to N', at least one alkoxysilyl group as an S2 substituent independently selected from the group consisting of S21 to S25, at least one epoxy group of S4(3) selected from the group consisting of Formulae S41 to S45 and an optional substituent of Formula S3 selected from the group consisting of Formulae S31 to S35, wherein the cores of Formulae A' to I' may be additionally connected via a linking moiety selected from the group consisting of LG1 to LG7 and Lg15 to LG21, and the cores of Formula J' may be additionally connected via LG2 or LG16, may be provided.

A method of preparing an epoxy compound having an alkoxysilyl group comprising an epoxy compound including tetraphenylethane-based aromatic core according to an embodiment of the present invention is as follows. Preparation Method 1 corresponds to a case of having an S1 substituent, and Preparation Method 2 corresponds to a case of having an S2 substituent.

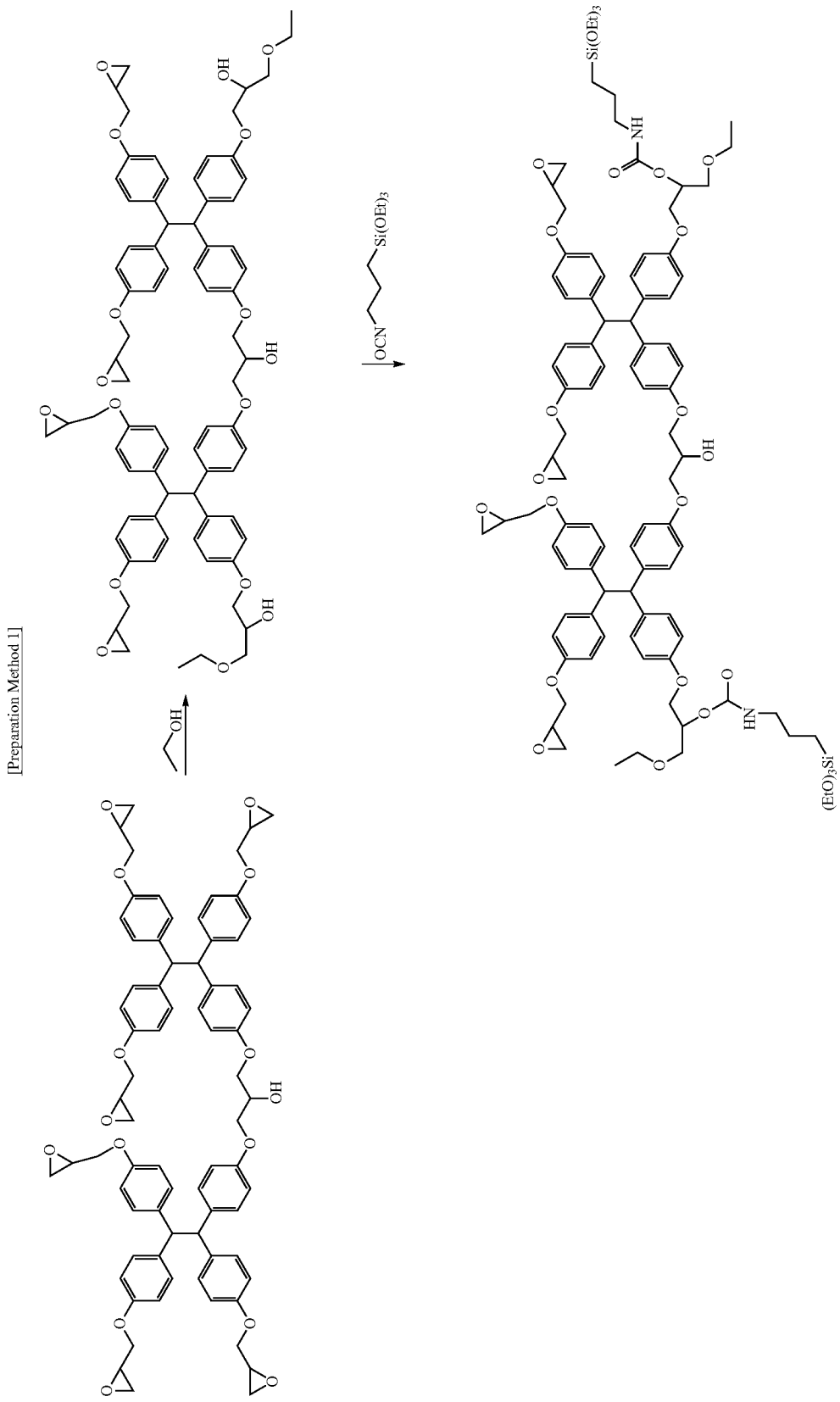

-continued
[Preparation Method 2]
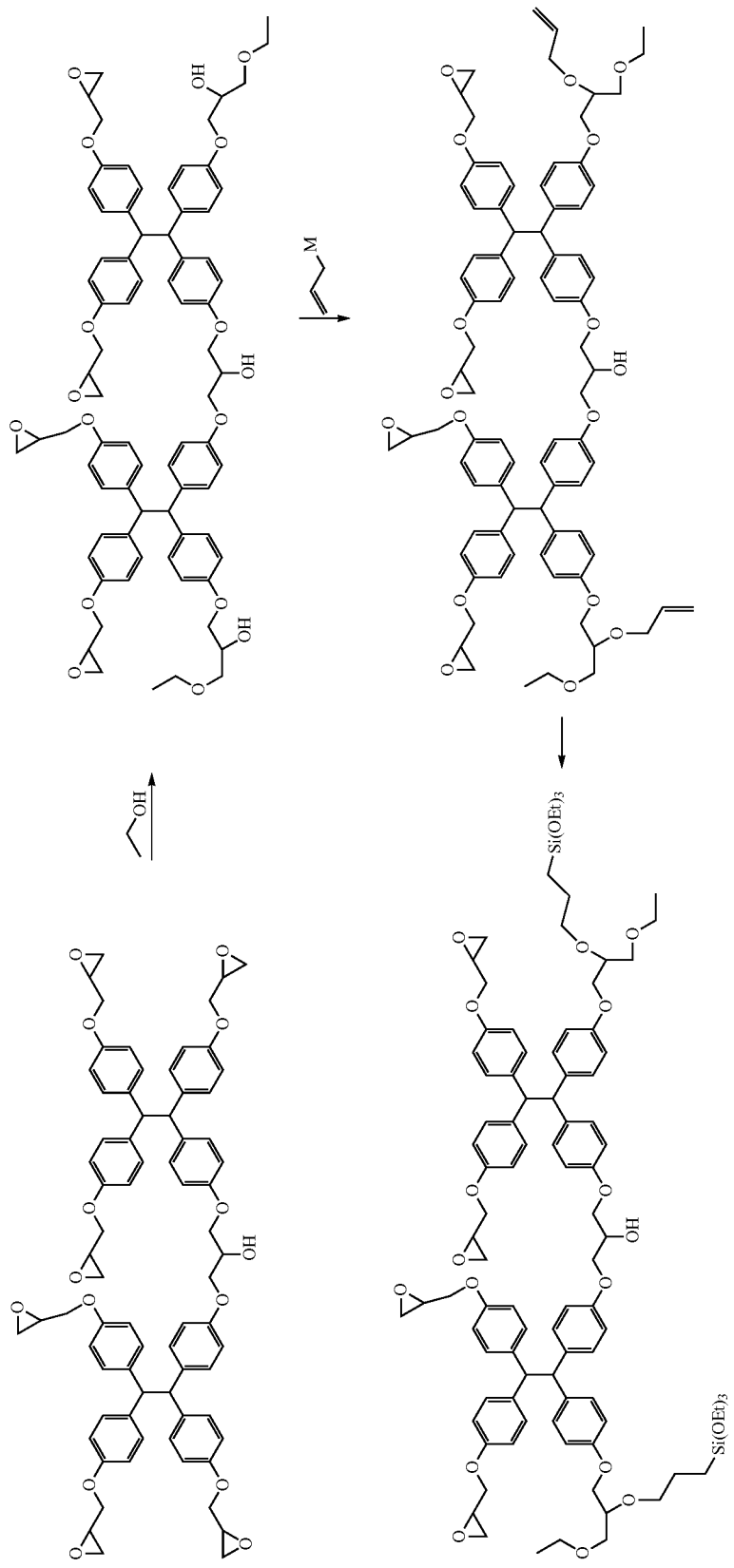

3. Epoxy Composition

According to another embodiment of the present invention, an epoxy composition comprising an epoxy compound having an epoxy group and at least one alkoxysilyl group of an S1 substituent independently selected from the group consisting of Formulae S11 to S15 or an S2 substituent independently selected from the group consisting of Formulae S21 to S25 provided by an embodiment of the present invention is provided. Particularly, an epoxy composition comprising any alkoxysilylated epoxy compound (hereinafter, 'alkoxysilylated epoxy compound') provided in any embodiment of the present invention described in the above category concerning the epoxy compound, is provided.

Any composition provided in the present invention may be used in various uses such as an electronic material, for example, an electronic parts such as, a semiconductor substrate for example an IC substrate, a build-up film, an encapsulating material (packaging material), a printed circuit board, an adhesive, a paint, a composite material, or the like, without limitation. In addition, any composition provided in the present invention may be a curable composition and/or a curable composition comprising an inorganic material.

Any epoxy composition according to any embodiment of the present invention may include any kind and/or any mixing ratio as known in the art only if comprising an alkoxysilylated epoxy compound provided in any embodiment of the present invention. In this case, the kind and the mixing ratio of the curing agent, the curing accelerator (catalyst), the inorganic material (filler) (for example, inorganic particles and/or a fiber), and other additives are not limited.

Thus, an epoxy composition of any kind and/or ratio as known in this technical field may be understood to be included in the scope of the epoxy composition according to the present invention only if comprising any alkoxysilylated epoxy compound (hereinafter an 'epoxy compound of the present invention') provided in an embodiment of the present invention described in the category concerning the epoxy compound, and the kind and mixing ratio of the curing agent, the curing accelerator (catalyst), filler and other additives constituting the epoxy composition is not limited.

Further, in the epoxy composition according to an embodiment of the present invention, the epoxy compound may include any kind of epoxy compound commonly known in this art (hereinafter a 'common epoxy compound') as well as the epoxy compound of the present invention.

The epoxy composition according to an embodiment of the present invention may include without limitation, 1 to 100 wt %, preferably 5 to 100 wt % of the epoxy compound of the present invention and 0 to 99 wt %, preferably 0 to 95 wt % of the common epoxy compound on the basis of the total weight of the epoxy compound.

The common epoxy compounds may be any epoxy compound commonly known in this art without limitation, and may be, for example, at least one epoxy compound selected from the group consisting of a glycidyl ether-based, a glycidyl-based, a glycidyl amine-based and a glycidyl ester-based epoxy compound. Particularly, at least one selected from the group consisting of a bisphenol-based, a biphenyl-based, a naphthalene-based, a benzene-based, a thiodiphenol-based, a fluorene-based, an anthracene-based, an isocyanurate-based, a triphenylmethane-based, a 1,1,2,2-tetraphenylethane-based, a tetraphenylmethane-based, a 4,4'-diaminodiphenylmethane-based, an aminophenol-based, an alicyclic, an aliphatic, and a novolac-based epoxy compound may be used.

According to another embodiment of the present invention, an epoxy composition comprising at least one novel epoxy compound selected from the group consisting of Formulae A' to N' and a curing agent (hereinafter a 'curing agent-containing composition') may be provided. The curing agent-containing composition is understood to include any kind and/or ratio of epoxy composition known in this technical field only if including at least one novel epoxy compound selected from the group consisting of Formulae A' to N' and a curing agent, and the kind and the mixing ratio of a curing accelerator (catalyst), an inorganic material (filler) (for example, inorganic particles and/or a fiber), any common epoxy compound and other additive constituting the epoxy composition are not limited.

In the composition comprising an alkoxysilylated epoxy compound and a curing agent according to an embodiment of the present invention, the curing agent may be any curing agent commonly known as a curing agent of an epoxy resin and may include for example, an amine, a polyphenol, an acid anhydride, etc., without limitation.

More particularly, an aliphatic amine, an alicyclic amine, an aromatic amine, other amines and a modified polyamine may be used as the amine curing agent, without limitation. In addition, an amine compound including two or more primary amine groups may be used. Particular examples of the amine curing agent may include at least one aromatic amine selected from the group consisting of 4,4'-dimethylaniline (diamino diphenyl methane, DAM or DDM), and diamino diphenyl sulfone (DDS) and m-phenylene diamine, at least one aliphatic amine selected from the group consisting of diethylene triamine (DETA), diethylene tetramine, triethylene tetramine (TETA), m-xylene diamine (MXTA), methane diamine (MDA), N,N'-diethylenediamine (N,N'-DEDA), tetraethylenepentaamine (TEPA), and hexamethylenediamine, at least one alicyclic amine selected from the group consisting of isophorone diamine (IPDI), N-aminoethyl piperazine (AEP), and bis(4-amino 3-methylcyclohexyl)methane (Larominc 260), and other amines such as dicyandiamide (DICY), and a modified amine such as a polyamide-based compound, an epoxide-based compound, or the like.

Examples of the polyphenol curing agent may include, without limitation, a phenol novolac resin, a cresol novolac resin, a bisphenol A novolac resin, a xylene novolac resin, a triphenyl novolac resin, a biphenyl novolac resin, a dicyclopentadiene novolac resin, a naphthalene novolac resin, or the like.

Examples of the acid anhydride curing agent may include, without limitation, an aliphatic acid anhydrous such as dodecenyl succinic anhydride (DDSA), poly azelaic poly anhydride, or the like, an alicyclic acid anhydride such as hexahydrophthalic anhydride (HHPA), methyl tetrahydrophthalic anhydride (MeTHPA), methylnadic anhydride (MNA), or the like, an aromatic acid anhydride such as trimellitic anhydride (TMA), pyromellitic acid dianhydride (PMDA), benzophenonetetracarboxylic dianhydride (BTDA), or the like, and a halogen-based acid anhydride such as tetrabromophthalic anhydride (TBPA), chlorendic anhydride, or the like.

In general, the degree of curing of an epoxy composite may be controlled by the reaction degree of the curing agent and the epoxy group. According to the range of the target degree of curing, the amount of the curing agent may be controlled based on the concentration of the epoxy group of an epoxy compound. For example, in the case that an amine curing agent is used, the ratio of the epoxy equivalent/amine equivalent may preferably be controlled to 0.5 to 2.0, for example, 0.8 to 1.5 in an equivalent reaction of the amine curing agent and the epoxy group.

Though the mixing ratio of the curing agent has been explained with respect to the amine curing agent, a polyphenol curing agent, an acid anhydride curing agent and any curing agent for curing epoxy compounds not separately illustrated in this disclosure but used for curing may be used by appropriately mixing a stoichiometric amount according to the chemical reaction of the epoxy functional group and the reactive functional group of the curing agent based on the concentration of the total epoxy group in the epoxy composition according to the desired range of the degree of curing. The above-described elements are commonly known in this field.

In addition, an imidazole described below may be widely used as the curing accelerator or may be used as a single curing agent. In the case that the imidazole is used as the curing agent, 0.1 to 10 phr on the basis of the epoxy may be used.

An optional curing accelerator (catalyst) may be additionally included as occasion demands to promote the curing reaction of the alkoxysilylated epoxy compound and the curing agent in any epoxy composition provided in the present invention. Any curing accelerator (catalysts) commonly used for curing an epoxy composition in this technical field may be used without limitation, for example, an imidazole, a tertiary amine, a quaternary ammonium, an organic acid salt, a phosphorus compound curing accelerator may be used.

More particularly, for example, the imidazole curing accelerator such as dimethylbenzylamine, 2-methylimidazole (2MZ), 2-undecylimidazole, 2-ethyl-4-methylimidazole (2E4M), 2-phenylimidazole, 1-(2-cyanoethyl)-2-alkyl imidazole and 2-heptadecylimidazole (2HDI); the tertiary amine curing accelerator such as benzyldimethylamine (BDMA), tris dimethylaminomethyl phenol (DMP-30) and triethylenediamine; the quaternary ammonium curing accelerator such as tetrabutylammonium bromide, or the like; diazabicycloundecene (DBU), or an organic acid salt of DBU; the phosphorus compound-based curing accelerator such as triphenyl phosphine, phosphoric acid ester, or the like, and a Lewis acid such as $BF_3$-monoethylamine ($BF_3$-MEA), or the like, may be illustrated without limitation. Latent curing accelerators such as coated microcapsules or chelates may also be used. These compounds may be used alone or as a mixture of two or more thereof according to curing conditions.

The mixing amount of the curing accelerator may be a commonly applied mixing amount in this art without limitation. For example, 0.1 to 10 parts by weight of the curing accelerator on the basis of 100 parts by weight of the epoxy compound, for example, 0.5 to 5 parts by weight of the curing accelerator may be used. In the case that the mixing amount of the curing accelerator is less than 0.1 parts by weight, the accomplishment of curing reaction accelerating effect may be difficult, and in the case that the mixing amount is greater than 10 parts by weight, curing reaction may be too rapid. Through using the curing accelerator within the above-described range, the curing may be rapidly achieved, and the improvement of working throughput may be expected.

In the case that the alkoxysilyl group reaction catalyst is included in the curing accelerator-containing composition and a composition according to any embodiment of the present invention, the alkoxysilyl group reaction catalyst may be at least one selected from the group consisting of at least one inorganic acid selected from the group consisting of, for example, nitric acid, sulfuric acid, hydrochloric acid, acetic acid and phosphoric acid, ammonia, KOH, $NH_4OH$, amine, a transition metal alkoxide, a metal oxide, an organic acid salt and a metal halide (for example, a tin compound such as dibutyltin dilaurate, tin octylate, tin(II) 2-ethylhexanoate, or the like). These compounds may be used alone or as a mixture of two or more thereof. The mixing ratio of the alkoxysilyl group reaction catalyst is not specifically limited; however, 0.01 phr to 10 phr of the alkoxysilyl group reaction catalyst may be used with respect to the epoxy compound of the present invention in consideration of reactivity.

In the epoxy composition, water may be additionally included to increase the efficiency of the alkoxysilyl reaction catalyst. The mixing ratio of water is not specifically limited; however, 0.01 to 20 equivalents of water may be included per 1 equivalent of the alkoxysilyl group.

Further, the epoxy composition provided in the present invention may additionally include at least one selected from the group consisting of inorganic particles and a fiber as the filler of inorganic component.

Any inorganic particle known to be used to reinforce the physical properties of a common organic resin may be used. Examples of the inorganic particles may include, without limitation, at least one selected from the group consisting of at least one metal oxide selected from the group consisting of silica (including, for example, fused silica and crystalline silica), zirconia, titania and alumina, silicon nitride, aluminum nitride and silsesquioxane. The inorganic particles may be used alone or as a mixture of two or more thereof.

The inorganic particles having a particle size of 0.5 nm to several tens of μm (for example, from 50 μm to 100 μm) may be used in consideration of the use of a composite, particularly, the dispersibility of the inorganic particles, or the like. Since the inorganic particles are dispersed in the epoxy compound, and the dispersibility is different according to the particle size, using the inorganic particles having different particle size in the above-described range together may preferable. In addition, the distribution range of the inorganic particles to be mixed is preferably increased to increase the fill factor of the inorganic particles.

In the epoxy composition in accordance with an embodiment of the present invention, the fill factor of the inorganic particles with respect to the epoxy compound may be appropriately controlled in consideration of the CTE decrease of an epoxy composite and an appropriate viscosity required while applying. For example, the amount of the inorganic particles may be 5 wt % to 95 wt %, for example, 5 wt % to 90 wt %, for example, 10 wt % to 90 wt %, for example, 30 wt % to 95 wt %, for example, 30 wt % to 90 wt %, for example, 5 wt % to 60 wt %, for example, 10 wt % to 50 wt % based on the total weight of the solid content of the epoxy composition (based on the total weight of the cured epoxy product for the cured epoxy product).

More particularly, in an exemplary embodiment, in the case that the epoxy composition is used as a semiconductor encapsulating agent, or the like, the amount of the inorganic particles may be, for example, 30 wt % to 95 wt %, for example, 30 wt % to 90 wt %, without limitation, based on the total weight of the solid content of the epoxy composition (based on the total weight of the cured epoxy product for the cured epoxy product) in consideration of the CTE value and material processability. In other exemplary embodiments, in the case that the epoxy composition is used in a semiconductor substrate, the amount of the inorganic particles may be 5 wt % to 85 wt %, for example, 10 wt % to 80 wt % based on the total weight of solid content of the epoxy composition (based on the total weight of the cured epoxy product for the cured epoxy product) in consideration of the CTE value and the strength of the substrate.

Meanwhile, in the case that the fiber is used as the inorganic material, a composite may mainly be obtained by an immersing method of the fiber with the epoxy composition. Thus, the size of the fiber may not be specifically limited. Any kind of fiber commonly used in this field may be used and dimensions thereof are not limited.

Any commonly used fiber for improving physical properties of a common organic resin cured product may be used, without limitation. Particularly, a glass fiber, an organic fiber or a mixture thereof may be used. In addition, the term 'glass fiber' used in this application may include a glass fiber fabric, a glass fiber non woven product, or the like, as well as the glass fiber. Examples of the glass fiber may include, without limitation, an E-glass fiber, a T-glass fiber, an S-glass fiber, an NE-glass fiber, a D-glass fiber, a quartz glass fiber, or the like. For example, the glass fiber of E or T may be included. The organic fiber may include at least one selected from the group consisting of a liquid crystal polyester fiber, a polyethyleneterephthalate fiber, a wholly aromatic fiber, a polybenzoxasol fiber, a nylon fiber, a polyethylene naphthalate fiber, a polypropylene fiber, a polyether sulfone fiber, a polyvinylidene fluoride fiber, a polyethylene sulfide fiber and a polyether ether ketone fiber. These fibers may be used alone or as a combination of two or more thereof.

The amount of the fiber in any epoxy composition according to the present invention, for example, in a glass fiber composite of the epoxy composition, may be 10 wt % to 90 wt %, for example, 30 wt % to 70 wt %, in addition, for example, 35 wt % to 70 wt % based on the total weight of the epoxy composition. Thus, the amount of the resin may be 10 wt % to 90 wt %, for example, 30 wt % to 70 wt %, in addition, for example, 35 wt % to 70 wt %. The amount of the fiber within the above-described range may be preferred in consideration of the increase in heat resistance and the processability aspect. Meanwhile, in the epoxy composition, the cured product, or the like, comprising the fiber, solid parts excluding the fiber from the total solid content is referred to as a resin content (R/C).

Further, in the epoxy composition comprising the fiber may additionally include inorganic particles as occasion demands. In this case, the inorganic particles may be comprised in a ratio of 1 wt % to 80 wt % in the resin component based on the total weight of resin in consideration of the improvement of the physical properties and processability. In this case, the kind of the inorganic particles is not specifically limited, and any inorganic particle known in this art may be used. For example, the above-described inorganic particles may be used.

In the epoxy composition, other additives such as an organic solvent, a releasing agent, a surface treating agent, a flame retardant, a plasticizer, bactericides, a leveling agent, a defoaming agent, a colorant, a stabilizer, a coupling agent, a viscosity controlling agent, a diluent, or the like may be mixed to control the physical properties of the epoxy composition within the range of undamaging the physical properties of the epoxy composition as occasion demands.

For imparting solubility to any composition of the present invention, a rubber and/or a thermoplastic resin may be added to the epoxy composition of the present invention. As the thermoplastic resin and a rubber-modified epoxy resin, commonly known resins in this field may be used. As the rubber, any rubber known in this field may be used only if the rubber is not dissolved in a solvent used in the composition and maintains a dispersed state in the composition. The kind of the rubber may include, for example, an acrylonitrile butadiene rubber, a butadiene rubber, an acryl rubber, core-shell type rubber particles, cross-linked acrylonitrile butadiene rubber particles, cross-linked styrene butadiene rubber particles, acryl rubber particles, or the like, without limitation. These materials may be used alone, or at least two thereof may be used at the same time. In the case that a rubber having a particle shape is used, the mean particle diameter may preferably be from 0.005 to 1 µm, and more preferably may be from 0.2 to 0.6 µm in consideration of the improvement of physical properties. The rubber particles may be mixed in an amount ratio, for example, of 0.5 to 10 wt % based on the weight of the solid content of the epoxy composition in consideration of physical properties. As the thermoplastic resin, a phenoxy resin, a polyvinyl acetal resin, a polyimide resin, a polyamideimide resin, a polyether sulfone resin, a polysulfone resin, or the like may be used, without limitation. These materials may be used alone or at least two thereof may be used at the same time. The thermoplastic resin may be mixed in a ratio of, for example, from 0.5 to 60 wt %, and preferably from 3 to 50 wt % based on the weight of the solid content of the epoxy composition in consideration of physical properties.

The epoxy composition provided in accordance with an exemplary embodiment of the present invention may be used as an electronic material. Particularly, the electronic material may include a prepreg, a laminate obtained by forming a metal layer on a prepreg, a substrate, a film, a printed circuit board, a packaging material, etc. According to another embodiment of the present invention, a semiconductor apparatus obtained by installing a semiconductor device on a printed circuit board manufactured using the composition comprising the alkoxysilylated epoxy compound of the present invention and/or a semiconductor apparatus including a semiconductor packaging material manufactured using a composition comprising an alkoxysilylated epoxy compound of the present invention, are provided.

According to another embodiment of the present invention, a cured product of the epoxy composition provided in the exemplary embodiments of the present invention will be provided. The cured product may be used to include a partially-cured product. In the case that the epoxy composition provided in exemplary embodiments of the present invention is practically applied, for example, as the electronic material, etc., the cured product may be used, and a cured product of the composition comprising an epoxy compound and a filler as an inorganic component in this technical field may be commonly referred to as a composite.

The alkoxysilylated epoxy compound provided in an embodiment of the present invention may show good heat resistance and/or good flame retardant properties in the cured product of a composition comprising the filler as the inorganic component.

Particularly, the composite may exhibit a low CTE, for example, 60 ppm/° C. or less, for example, 15 ppm/° C. or less, for example, 12 ppm/° C. or less, for example, 10 ppm/° C. or less, for example, 8 ppm/° C. or less, for example, 6 ppm/° C. or less, for example, 4 ppm/° C. or less. The physical properties of the composite are good in the case that the CTE value is small, and the lower value of the CTE is not particularly delimited.

For example, a composite including any epoxy compound in accordance with exemplary embodiments of the present invention as the epoxy compound, and a glass fiber, for example, an E-glass fiber and/or a T-glass fiber as the inorganic material, and having the resin content (the resin content may or may not include inorganic particles) of 30 wt % to 60 wt % may have a CTE of 10 ppm/° C. or less, for example, 8 ppm/° C. or less, for example, 6 ppm/° C. or less, for example, 4 ppm/° C. or less.

In addition, for example, a composite comprising any epoxy compound in accordance with exemplary embodiments of the present invention as the epoxy compound, and inorganic particles as the inorganic material, for example, silica particles of 60 wt % to 80 wt %, for example, 70 wt % to 80 wt %, may have a CTE of 20 ppm/° C. or less, for example, 15 ppm/° C. or less, for example, 10 ppm/° C. or less, for example, 8 ppm/° C. or less, for example, 6 ppm/° C. or less, for example, 4 ppm/° C. or less.

In addition, Tg of the composite (a cured product comprising an inorganic material) according to the present invention may be higher than 100° C., for example, 130° C. or over, in addition, for example, 250° C. or over. Otherwise, the composite may be Tg-less. The physical properties of the composite are good in the case that the Tg value is large, and the upper value of the Tg is not particularly delimited.

Mode for Invention

Hereinafter, the present invention will be described in detail referring to examples. The following examples are for illustration, and the present invention is not limited thereto.

SYNTHETIC EXAMPLES

Synthetic Example 1

Synthesis of Naphthalene Epoxy Compound A':
Reaction with $CH_3CH_2$—OH

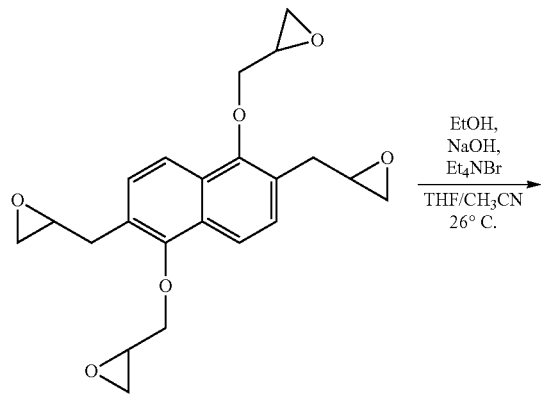

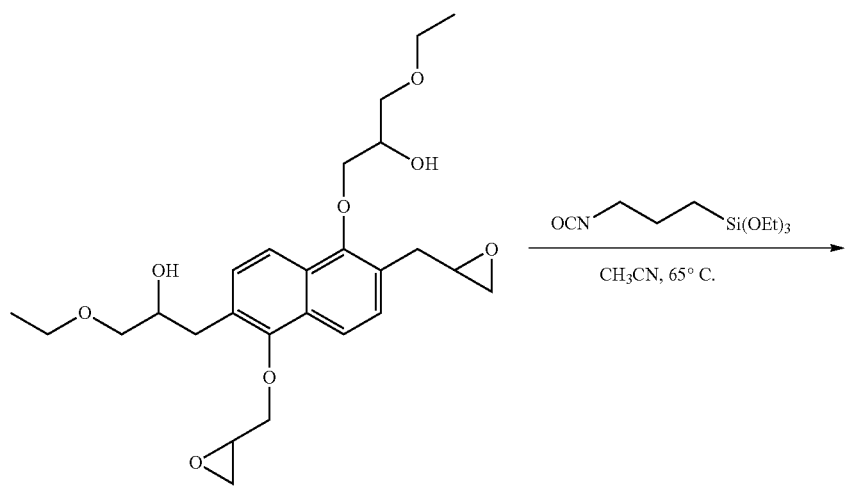

A-1

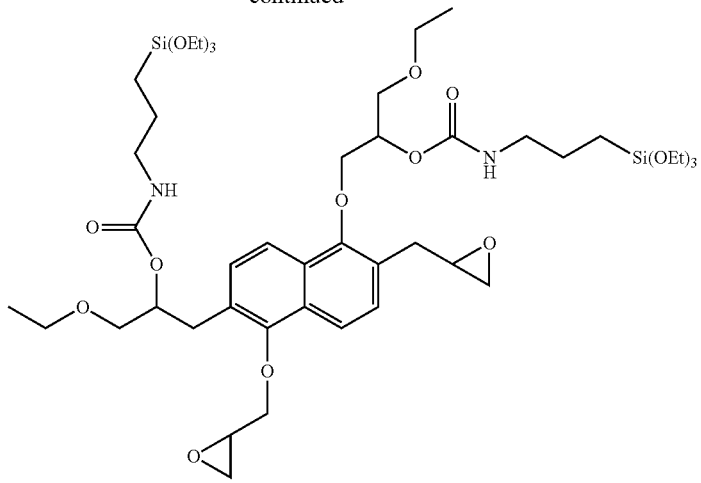

A-2-1

(1) 1ˢᵗ Step 20 g of 2,2'-((1,5-bis(oxiran-2-ylmethoxy)naphthalene-2,6-diyl)bis(methylene))bis(oxirane), 2.92 g of NaOH, 3.54 g of tetraethylammonium bromide (NEt₄Br), 70 ml of tetrahydrofuran (THF), 70 ml of CH₃CN and 82 ml of ethanol (EtOH) were added to a two-necked flask at room temperature, followed by stirring at 26° C. for 5 hours and 30 minutes. Then, 5 ml of a saturated ammonium chloride (NH₄Cl) solution was added thereto, followed by stirring for 3 minutes. Solvent was removed using a rotary evaporator, and an organic layer was separated by working-up with 400 ml of ethyl acetate (EA) and 300 ml of water. MgSO₄ was added to the separated organic layer to remove residual H₂O and filtered, and solvent was evaporated to produce a ring-opened epoxy intermediate.

NMR after 1ˢᵗ Step

¹H NMR (400 MHz, CDCl₃): δ=1.17 (t, 8 Hz, 6H), 2.52-2.57 (m, 1H), 2.61-2.66 (m, 2H) 2.73-2.81 (m, 3H), 2.90-2.93 (m, 2H), 3.16-3.18 (m, 1H), 3.35-3.37 (m, 1H), 3.80-4.13 (m, 13H), 4.22-4.25 (m, 1H), 7.28 (d, J=8.5 Hz, 2H), 7.75 (d, J=8.5 Hz, 2H).

20 g of the intermediate obtained in the 1ˢᵗ step, 22.1 ml of 3-(triethoxysilyl)propyl isocyanate, 15.6 ml of N,N-diisopropylethylamine (DIPEA), and 897 ml of CH₃CN were added to a two-necked flask, followed by stirring at 65° C. for 20 hours. After completing the reaction, 300 ml of ethyl acetate was added, and a mixture thus obtained was worked-up with a saturated ammonium chloride (NH₄Cl) aqueous solution. An organic layer was separated, and residual H₂O in the organic layer was removed by adding MgSO₄. Organic solvent was removed using a rotary evaporator, and hexane was added to the crude product thus obtained and stored at −15° C. to produce a precipitate. After removing the supernatant, a process of forming a precipitate by pouring hexane into a precipitate was repeated twice to produce a target product. The concentration ratio of the reactive functional group of the alkoxysilyl epoxy was [epoxy group]:[silyl group]=1:1.

NMR after 2ⁿᵈ Step

¹H NMR (400 MHz, CDCl₃): δ=0.60 (t, J=8 Hz, 4H), 1.18-1.25 (m, 24H), 1.65 (t, J=8 Hz, 4H), 2.52-2.57 (m, 1H), 2.61-2.66 (m, 2H) 2.73-2.81 (m, 3H), 2.90-2.93 (m, 2H), 3.16-3.20 (m, 5H), 3.35-3.37 (m, 1H), 3.76-4.13 (m, 25H), 4.22-4.25 (m, 1H), 5.12-5.25 (m, 2H), 7.28 (d, J=8.5 Hz, 2H), 7.75 (d, J=8.5 Hz, 2H).

Synthetic Example 2

Synthesis of Biphenyl Epoxy Compound B':
Reaction with CH₃CH₂—OH

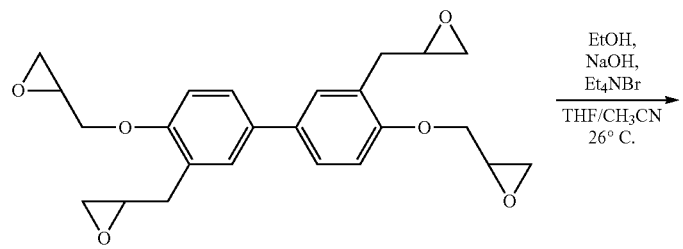

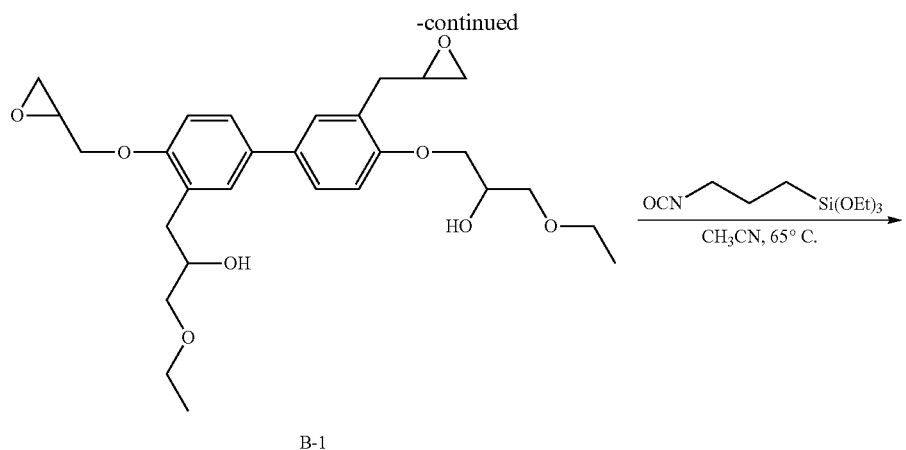

B-1

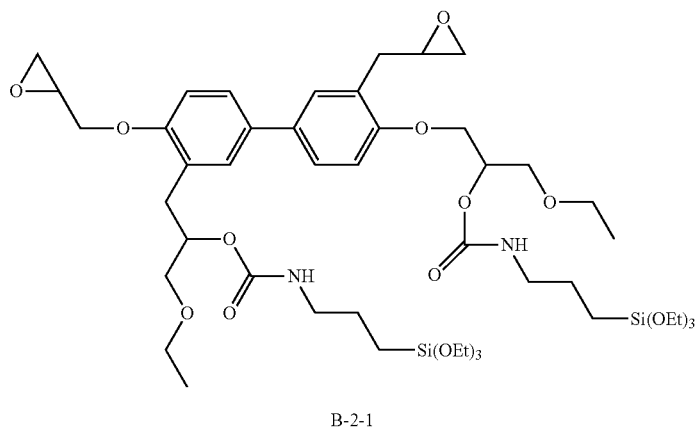

B-2-1

The same procedure as that of Synthetic Example 1 was undertaken. The additive amounts of compounds are shown in Table 1 and Table 2. The concentration ratio of the reactive functional group of the alkoxysilyl epoxy thus obtained was [epoxy group]:[silyl group]=1:1.

NMR after $1^{st}$ Step $^1$H NMR (400 MHz, CDCl$_3$): δ=1.16 (t, 8 Hz, 6H), 2.53-2.57 (m, 1H), 2.61-2.65 (m, 2H), 2.73-2.81 (m, 3H), 2.88-2.92 (m, 2H), 3.16-3.18 (m, 1H), 3.35-3.37 (m, 1H), 3.80-4.04 (m, 13H), 4.22-4.25 (m, 1H), 6.73-6.75 (m, 2H), 7.03-7.05 (m, 4H).

NMR after $2^{nd}$ Step $^1$H NMR (400 MHz, CDCl$_3$): δ=0.62 (t, J=8 Hz, 4H), 1.16-1.24 (m, 24H), 1.62 (t, J=8 Hz, 4H), 2.53-2.57 (m, 1H), 2.61-2.65 (m, 2H), 2.73-2.81 (m, 3H), 2.88-2.92 (m, 2H), 3.15-3.18 (m, 5H), 3.35-3.37 (m, 1H), 3.78-4.04 (m, 25H), 4.22-4.25 (m, 1H), 5.12-5.20 (m, 2H), 6.73-6.75 (m, 2H), 7.03-7.05 (m, 4H).

Synthetic Example 3

Synthesis of Aminophenol Epoxy Compound C': Reaction with CH$_3$CH$_2$—OH

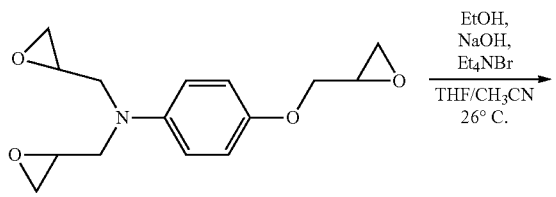

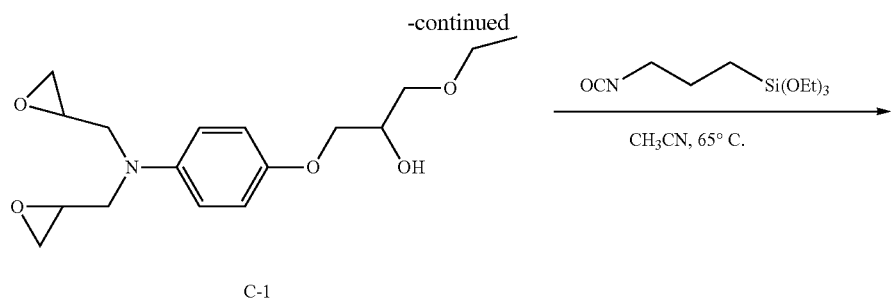

C-1

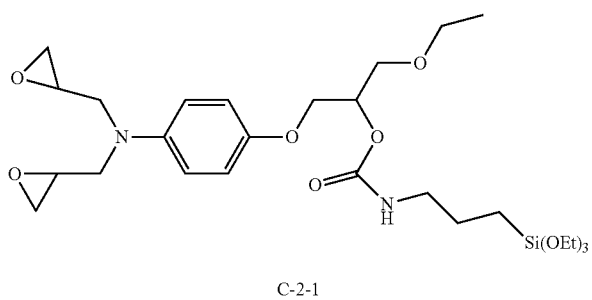

C-2-1

The same procedure as Synthetic Example 1 was undertaken. The additive amounts of compounds are shown in Table 1 and Table 2. The concentration ratio of the reactive functional group of the alkoxysilyl epoxy thus obtained was [epoxy group]:[silyl group]=2:1.

NMR after 1$^{st}$ Step $^1$H NMR (400 MHz, CDCl$_3$): δ=1.18 (t, 3H), 2.58-2.60 (m, 1.3H), 2.73-2.90(m, 2H), 3.16-3.20(m, 0.7H), 3.31-3.35 (m, 1.3H), 3.40-3.49(m, 2H), 3.76-4.14(m, 9H), 4.16-4.20 (m, 0.7H), 6.62-6.69(m, 2H), 6.80-6.83(m, 2H).

NMR after 2$^{nd}$ Step $^1$H NMR (400 MHz, CDCl$_3$): δ=0.61 (t, J=8 Hz, 2H), 1.22 (m, 12H), 1.60 (t, J=8 Hz, 2H), 2.58-2.60(m, 1.3H), 2.73-2.90(m, 2H), 3.15-3.21(m, 2.7H), 3.31-3.35(m, 1.3H), 3.40-4.20(m, 17.7H), 5.13-5.28 (m, 1H), 5.86-5.98 (m, 1H), 6.62-6.69(m, 2H), 6.80-6.83 (m, 2H).

Synthetic Example 4

Synthesis of Aminodiphenylmethane Epoxy Compound D(1)': Reaction with CH$_3$CH$_2$—OH

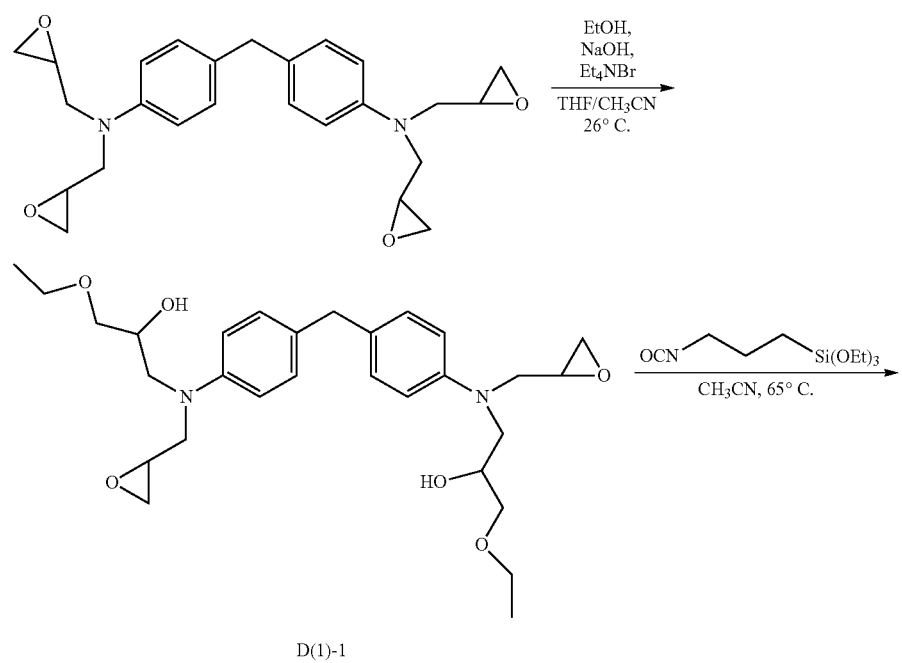

D(1)-1

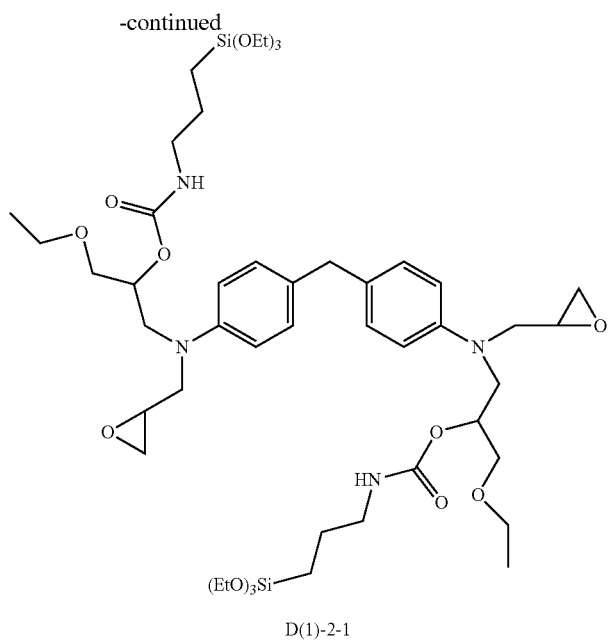

D(1)-2-1

The same procedure as that of Synthetic Example 1 was undertaken. The additive amounts of compounds are shown in Table 1 and Table 2. The concentration ratio of the reactive functional group of the alkoxysilyl epoxy thus obtained was [epoxy group]: [silyl group]=2:1.

NMR after 1st Step $^1$H NMR (400 MHz, CDCl$_3$): 1.21(t, 3.66H), 2.16(s, 1.2H), 2.57-2.55(m, 2.78H), 2.79-2.75(m, 2.78H), 3.16-3.13 (m, 3H), 3.46-3.36(m, 4H), 3.55-3.50(m, 2H), 3.72-3.66(m, 4H), 3.80-3.78(m, 3H), 6.74-6.71(m, 3H), 6.84(t, 1H, J=8.8 Hz), 7.09-7.02(m, 4H).

NMR after 2nd Step $^1$H NMR (400 MHz, CDCl$_3$): 0.63(t, 2.70H, J=4.4 Hz), 1.22(t, 16H), 1.62(m, 2.70H, J=3.6 Hz), 2.57-2.55(m, 2.73H), 2.79-2.75(m, 2.72H), 3.16-3.13(m, 5.7H), 3.47-3.38 (m, 4H), 3.63-3.51(m, 2H), 3.85-3.79(m, 13.6H), 5.07 (br, 1H), 6.74-6.72 (d, 3H, J=8.4 Hz), 6.84(t, 1H, J=8.8 Hz), 7.10-7.05(m, 4H).

Synthetic Example 5

Synthesis of Bisphenol A Epoxy Compound D(2)': Reaction with CH$_3$CH$_2$—OH

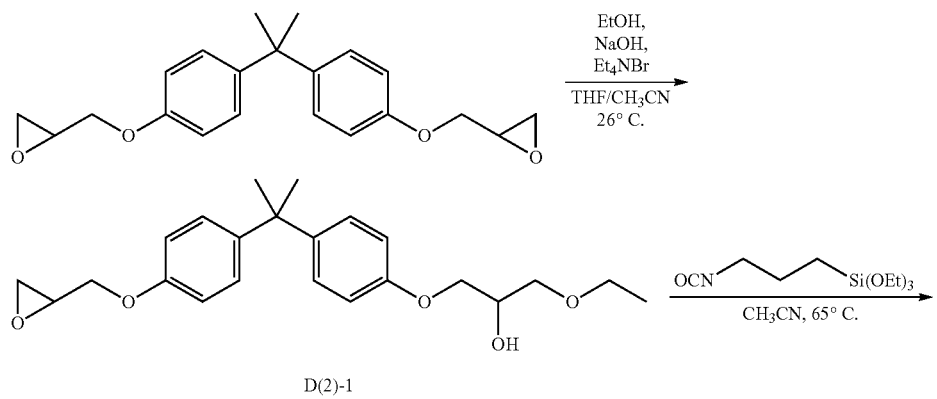

D(2)-1

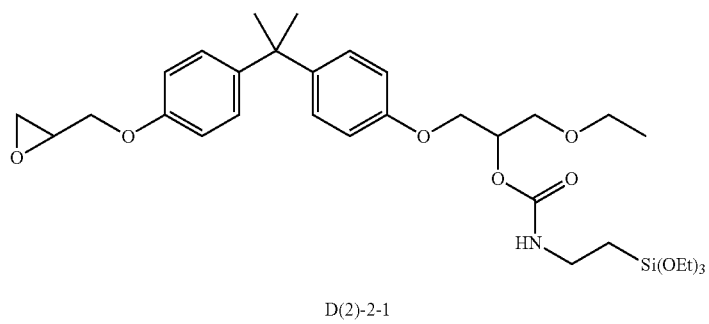

D(2)-2-1

The same procedure as that of Synthetic Example 1 was undertaken. The additive amounts of compounds are shown in Table 1 and Table 2. The concentration ratio of the reactive functional group of the alkoxysilyl epoxy thus obtained was [epoxy group]:[silyl group]=2:1.

NMR after 1$^{st}$ Step $^1$H NMR (400 MHz, CDCl$_3$): 1.12-1.18(m, 1.81H), 1.57 (s, 6H), 2.68-2.70(dd, 8 Hz, 3 Hz, 1.22H), 2.81-2.84(t, 8 Hz, 1.21H), 3.29-3.31(m, 1.19H), 3.42-3.44(m, 0.60H), 3.79(dd, 11 Hz, 6.5 Hz, 1.87H), 3.85-3.95(m, 1.21H), 3.95-4.10(m, 1.81H), 4.10-4.18(m, 0.60H), 4.27(dd,11 Hz, 3 Hz, 1.21H), 6.86(d, , 9 Hz, 4H), 7.12(d, 9 Hz, 4H).

NMR after 2$^{nd}$ Step $^1$H NMR (400 MHz, CDCl$_3$): 1.05-1.19 (m, 7.24 H), 1.43 (m, 1.21H), 1.57(s, 6H), 2.68-2.71(dd, 8 Hz, 3 Hz, 1.22H), 2.82-2.84(t, 8 Hz, 1.22H), 2.97 (m, 1.21H), 3.29-3.32(m, 1.19H), 3.42-3.44(m, 0.60H), 3.79(m, 5.49H), 3.85-3.95(m, 1.21H), 3.95-4.10(m, 1.81H), 4.10-4.19(m, 0.60H), 4.27 (dd,11 Hz, 3 Hz, 1.21H), 5.05 (m, 0.60H), 6.86 (d, , 9 Hz, 4H), 7.12(d, 9 Hz, 4H).

Synthetic Example 6

Synthesis of Binaphthalene Epoxy Compound E': Reaction with CH$_3$CH$_2$—OH

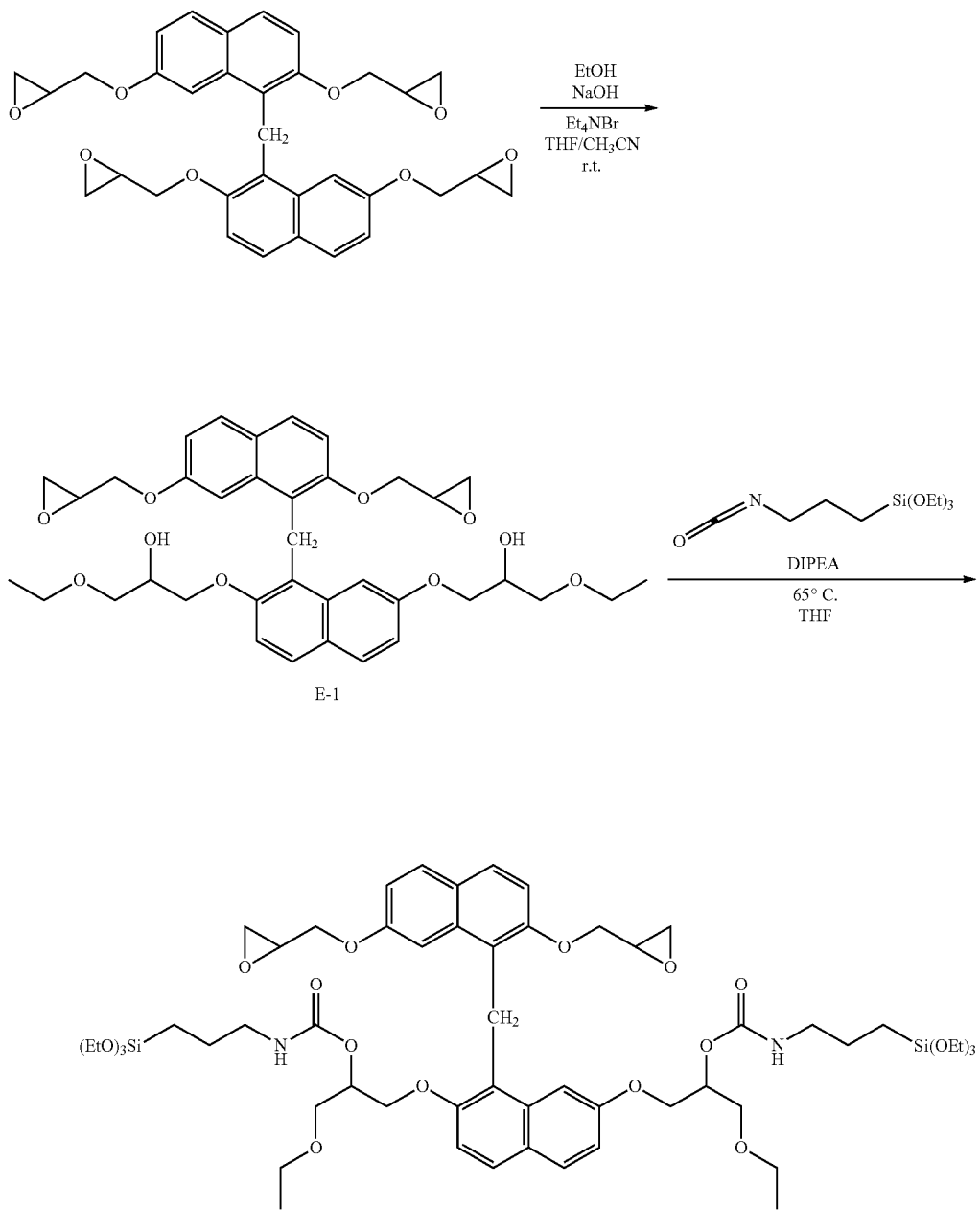

The same procedure as that of Synthetic Example 1 was undertaken. The additive amounts of compounds are shown in Table 1 and Table 2. The concentration ratio of the reactive functional group of the alkoxysilyl epoxy thus obtained was [epoxy group]:[silyl group]=2:1.

$^1$H NMR (400 MHz, CDCl$_3$): δ=1.19 (t, 8 Hz, 4H), 2.70-2.88 (m, 4H), 3.26-3.37 (m, 2H), 3.51-3.62 (m, 4H), 3.68-4.03 (m, 3.67H), 4.11-4.17 (m, 3.33), 4.22 (m, 1.33H), 4.38-4.41 (m, 1H), 4.90-4.92 (s, 2H), 6.88-7.18 (m, 4H), 7.42-7.62 (m, 4H).

$^1$H NMR (400 MHz, CDCl$_3$): δ=0.52 (t, 2.67H), 1.07-1.27 (m, 16H), 1.40-1.72 (m, 2.67H), 2.70-2.89 (m, 4H), 3.00-3.33(m, 5.33H), 3.37-3.51(m, 4H), 3.61-3.89 (m, 12H), 3.90-4.23 (m, 3.33H), 4.25-4.61 (m, 2.33H), 4.90-4.92 (s, 2H), 5.13-5.34 (m, 1.33H), 6.89-7.19 (m, 4H), 7.35-7.62 (m, 4H).

The same procedure as that of Synthetic Example 1 was undertaken. The additive amounts of compounds are shown in Table 1 and Table 2. The concentration ratio of the reactive functional group of the alkoxysilyl epoxy thus obtained was [epoxy group]:[silyl group]=1:1.

NMR after 1st Step $^1$H NMR (400 MHz, CDCl$_3$): δ=1.16 (t, 8 Hz, 6H), 2.53-2.56 (m, 1H), 2.59-2.66 (m, 2H), 2.72-2.81 (m, 3H), 2.89-2.93 (m, 2H), 3.16-3.18 (m, 1H), 3.35-3.37 (m, 1H), 3.79-4.15 (m, 13H), 4.22-4.25 (m, 1H), 6.73-6.75 (m, 2H), 7.03-7.05 (m, 4H), 7.22-7.36 (m, 6H), 7.74 (d, J=7.2 Hz, 2H).

NMR after 2$^{nd}$ Step $^1$H NMR (400 MHz, CDCl$_3$): δ=0.63 (t, J=8 Hz, 4H), 1.18-1.23 (m, 18H), 1.61 (t, J=8 Hz, 4H), 2.52-2.56 (m, 1H), 2.60-2.66 (m, 2H), 2.72-2.81 (m, 3H), 2.89-2.93 (m, 2H), 3.15-3.20 (m, 5H), 3.35-3.37 (m, 1H), 3.78-4.15 (m, 25H), 4.22-4.25 (m, 1H), 5.13-5.18 (m, 2H), 6.73-6.75 (m, 2H), 7.03-7.05 (m, 4H), 7.22-7.36 (m, 6H), 7.74 (d, J=7.2 Hz, 2H).

Synthetic Example 7

Synthesis of Diphenylfluorene Epoxy Compound F': Reaction with CH$_3$CH$_2$—OH

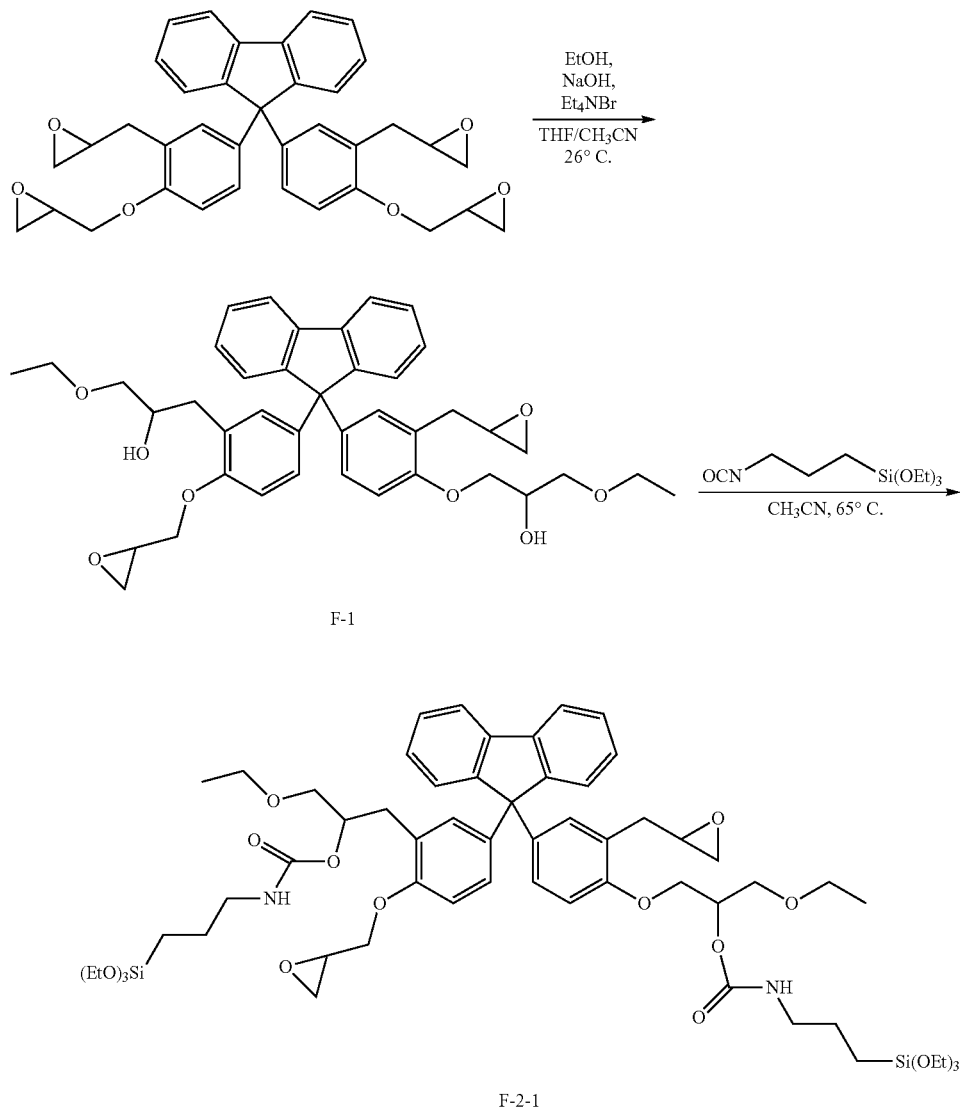

F-1

F-2-1

Synthetic Example 8
Synthesis of Tetraphenylmethane Epoxy Compound G': Reaction with CH₃CH₂—OH
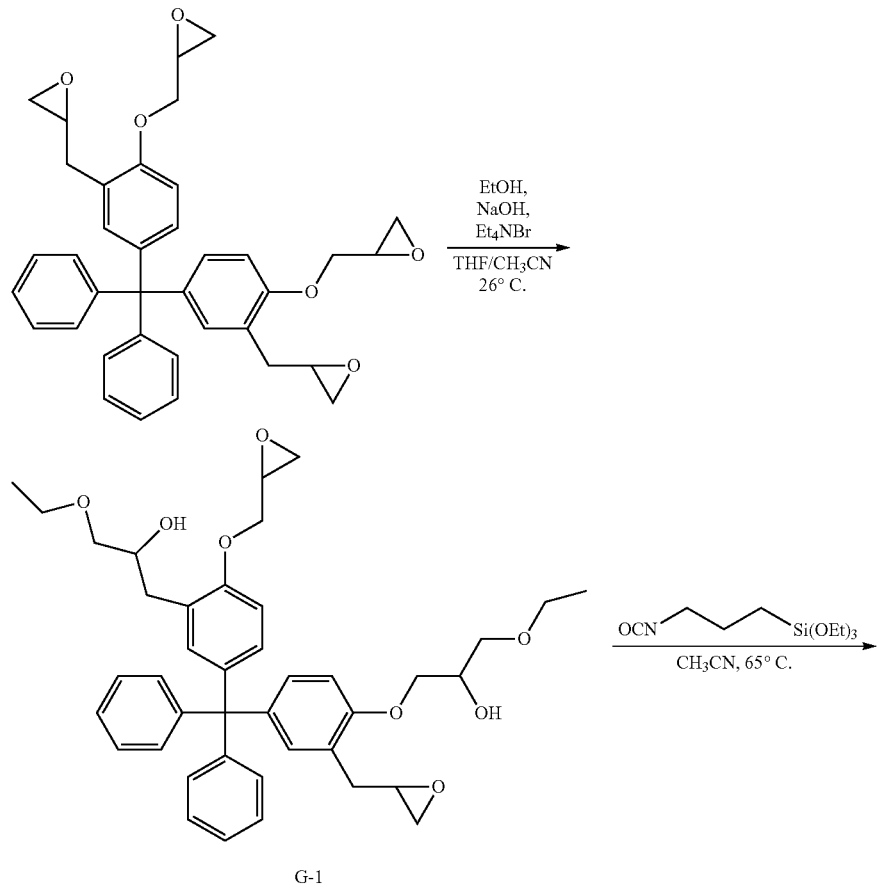
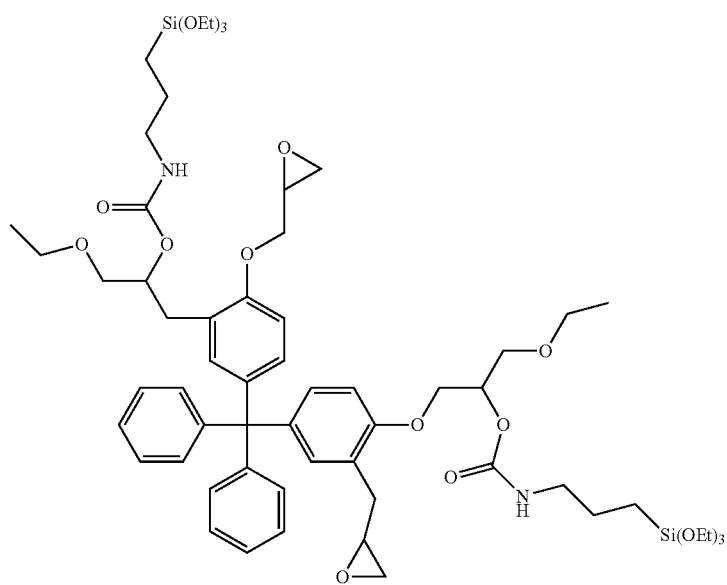
G-2-1

The same procedure as that of Synthetic Example 1 was undertaken. The additive amounts of compounds are shown in Table 1 and Table 2. The concentration ratio of the reactive functional group of the alkoxysilyl epoxy thus obtained was [epoxy group]:[silyl group]=1:1.

NMR after 1st Step $^1$H NMR (400 MHz, CDCl$_3$): δ=1.16 (t, 8 Hz, 6H), 2.53-2.57 (m, 1H), 2.68-2.71 (m, 1H), 2.80-2.84 (m, 2H), 2.90-2.93 (m, 1H), 3.17-3.30 (m, 2H), 3.35-3.38 (m, 1H), 3.80-4.16 (m, 16H), 6.70 (d, 2H), 6.96 (d, 2H), 7.07-7.27 (m, 12H).

NMR after 2$^{nd}$ Step $^1$H NMR (400 MHz, CDCl$_3$): δ=0.61 (t, J=8 Hz, 4H), 1.16-1.24 (m, 24H), 1.59 (t, J=8 Hz, 4H), 2.52-2.57 (m, 1H), 2.66-2.71 (m, 1H), 2.79-2.84 (m, 2H), 2.88-2.92 (m, 1H), 3.13-3.30 (m, 6H), 3.35-3.38 (m, 1H), 3.76-4.19 (m, 28H), 5.13-5.20 (m, 2H), 6.72 (d, 2H), 6.96 (d, 2H), 7.07-7.27 (m, 12H).

Synthetic Example 9

Synthesis of Triphenylmethane Epoxy Compound
H': Reaction with CH$_3$CH$_2$—OH

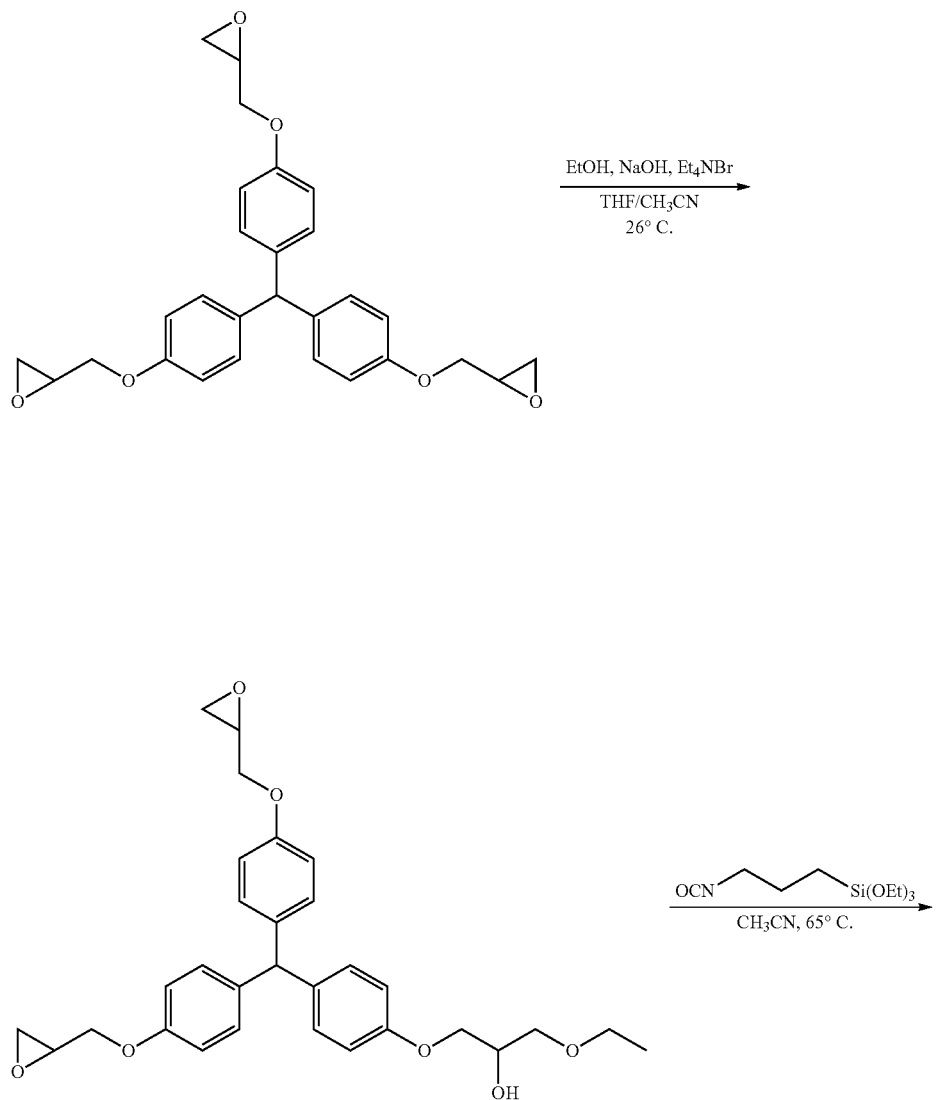

H-1

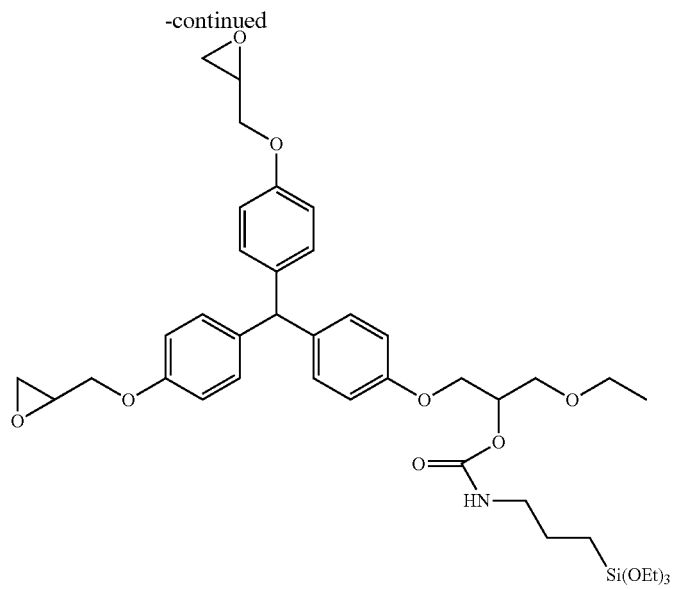

H-2-1

The same procedure as that of Synthetic Example 1 was undertaken. The additive amounts of compounds are shown in Table 1 and Table 2. The concentration ratio of the reactive functional group of the alkoxysilyl epoxy thus obtained was [epoxy group]:[silyl group]=2:1.

NMR after 1st Step $^1$H NMR (400 MHz, CDCl$_3$): δ=1.15 (t, 3H), 2.72-2.75 (m, 2H), 2.88-2.90 (m, 2H), 3.31-3.36 (m, 2H), 3.94 (dd, 2H, J=11.9 Hz, 5.6 Hz), 3.80-4.14 (m, 7H), 4.17 (dd, 2H, J=12.0 Hz, 3.6 Hz), 6.73 (d, 2H, J=8.8 Hz), 6.82 (d, 4H, J=8.8 Hz), 6.95 (d, 2H, J=8.8 Hz), 6.99 (d, 4H, J=8.8 Hz).

NMR after 2nd Step $^1$H NMR (400 MHz, CDCl$_3$): δ=0.61 (t, J=8 Hz, 2H), 1.22 (m, 12H), 1.60 (t, J=8 Hz, 2H), 2.72-2.75 (m, 2H), 2.88-2.90 (m, 2H), 3.15 (t, J=8 Hz, 2H), 3.31-3.36 (m, 2H), 3.78-4.14 (m, 15H), 4.17(dd, 2H, J=12.0 Hz, 3.6 Hz), 5.13-5.28 (m, 1H), 6.73(d, 2H, J=8.8 Hz), 6.82(d, 4H, J=8.8 Hz), 6.95 (d, 2H, J=8.8 Hz), 6.99 (d, 4H, J=8.8 Hz).

Synthetic Example 10

Synthesis of Tetraphenylethane Epoxy Compound I(1)': Reaction with CH$_3$CH$_2$—OH

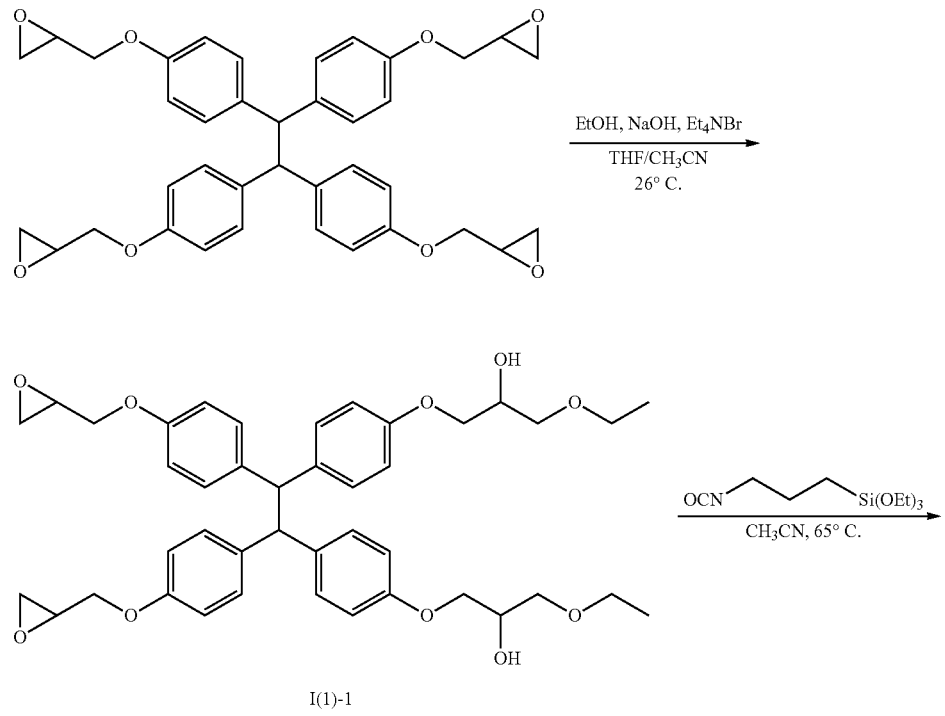

I(1)-1

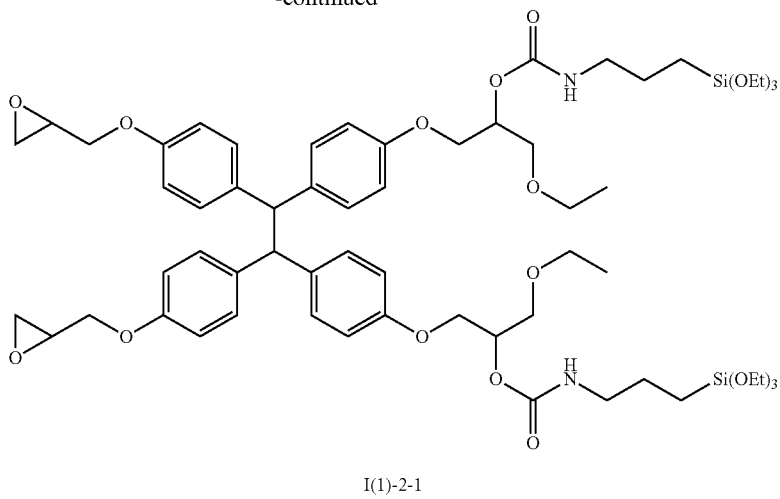

I(1)-2-1

The same procedure as that of Synthetic Example 1 was undertaken. The additive amounts of compounds are shown in Table 1 and Table 2. The concentration ratio of the reactive functional group of the alkoxysilyl epoxy thus obtained was [epoxy group]:[silyl group]=2:1.

NMR after 1$^{st}$ Step $^1$H NMR (400 MHz, CDCl$_3$): δ=1.19 (t, 4H), 2.68 (dd, J=4.8 Hz, 2.8 Hz, 2.67H), 2.84 (t, J=4.8 Hz, 2.67H), 3.22-3.27 (m, 2.67H), 3.51-3.62 (m, 1.33H), 3.80-3.84 (m, 1.33H), 3.87-4.01 (m, 8H), 4.05-4.10 (m, 4H), 4.55 (s, 2H), 6.67 (d, J=8.4 Hz, 8H), 7.00 (d, J=8.0 Hz, 8H).

NMR after 2$^{nd}$ Step $^1$H NMR (400 MHz, CDCl$_3$): δ=0.57 (t, J=8 Hz, 2.67H), 1.19 (t, J=8 Hz, 16H), 1.60 (t, J=8 Hz, 2.67H), 2.70 (dd, J=4.8 Hz, 2.8 Hz, 2.67H), 2.86 (t, J=4.8 Hz, 2.67H), 3.08 (t, J=8 Hz, 2.67H), 3.22-3.28 (m, 2.67H), 3.50-3.62 (m, 1.33H), 3.78-3.84 (m, 1.33H), 3.84-4.01 (m, 16H), 4.05-4.13(m, 4H), 4.45 (s, 2H), 5.03-5.28 (m, 1.33H), 6.67 (d, J=8.4 Hz, 8H), 7.00 (d, J=8.0 Hz, 8H).

Synthetic Example 11

Synthesis of Cyanurate Epoxy Compound J':
Reaction with CH$_3$CH$_2$—OH

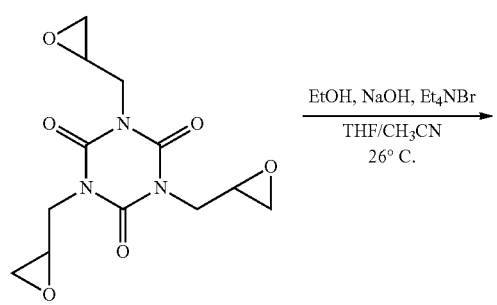

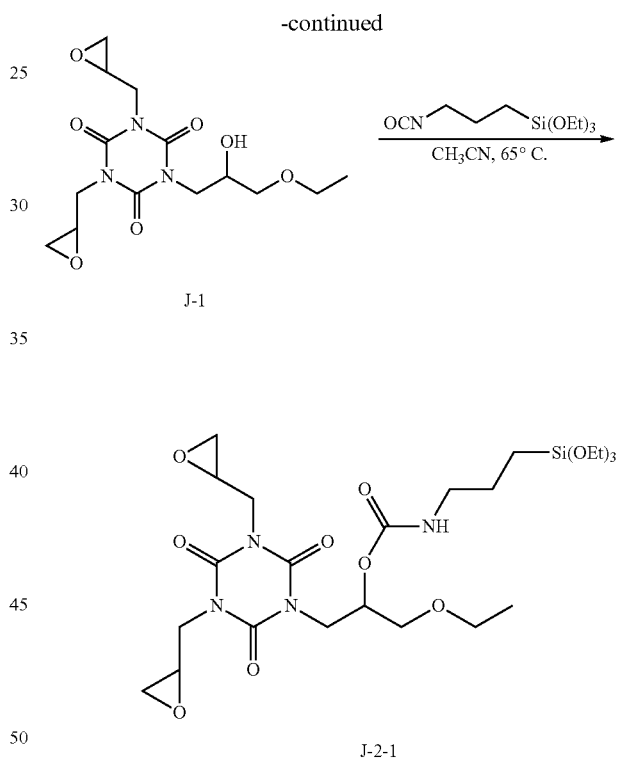

J-1

J-2-1

The same procedure as that of Synthetic Example 1 was undertaken. The additive amounts of compounds are shown in Table 1 and Table 2. The concentration ratio of the reactive functional group of the alkoxysilyl epoxy thus obtained was [epoxy group]:[silyl group]=2:1.

NMR after 1$^{st}$ Step $^1$H NMR (400 MHz, CDCl$_3$): δ=1.16 (t, 3H), 2.61-2.64 (m, 2H), 2.71-2.75 (m, 2H), 3.13-3.20 (m, 2H), 3.75-4.14 (m, 11H).

NMR after 2$^{nd}$ Step $^1$H NMR (400 MHz, CDCl$_3$): δ=1.16 (t, 3H), 0.63 (t, J=8 Hz, 2H), 1.26 (t, J=8 Hz, 9H), 1.63 (t, J=8 Hz, 2H), 2.60-2.64 (m, 2H), 2.71-2.75 (m, 2H), 3.13-3.20 (m, 4H), 3.75-4.14 (m, 17H), 5.13-5.29 (m, 1H).

TABLE 1

| | Epoxy compound (g) | NaOH (g) | Et₄NBr (g) | Nucleophile Type | Amount (ml) | THF (ml) | CH₃CN (ml) | Time (h) | Ratio of epoxy: secondary alcohol |
|---|---|---|---|---|---|---|---|---|---|
| Synthetic Example 2 | 20 | 2.72 | 3.30 | EtOH | 76 | 65 | 2.72 | 5.5 | 1:1 |
| Synthetic Example 3 | 20 | 4.17 | 5.06 | EtOH | 117 | 100 | 4.17 | 2.5 | 2:1 |
| Synthetic Example 4 | 20 | 2.45 | 2.97 | EtOH | 69 | 59 | 2.45 | 2.5 | 2:1 |
| Synthetic Example 5 | 20 | 0.69 | 0.84 | EtOH | 19 | 27 | 0.69 | 2.5 | 2:1 |
| Synthetic Example 6 | 20 | 2.72 | 3.30 | EtOH | 76 | 65 | 2.72 | 2.5 | 2:1 |
| Synthetic Example 7 | 20 | 1.90 | 2.31 | EtOH | 53 | 46 | 1.90 | 5.5 | 1:1 |
| Synthetic Example 8 | 20 | 1.90 | 2.30 | EtOH | 53 | 46 | 1.90 | 5.5 | 1:1 |
| Synthetic Example 9 | 20 | 2.50 | 3.03 | EtOH | 70 | 60 | 2.50 | 2.5 | 2:1 |
| Synthetic Example 10 | 20 | 1.85 | 2.24 | EtOH | 52 | 44 | 1.85 | 2.5 | 2:1 |
| Synthetic Example 11 | 20 | 3.50 | 4.24 | EtOH | 98 | 84 | 3.50 | 2.5 | 2:1 |
| Synthetic Example 16 | 20 | 1.85 | 2.24 | Et₂NH | 92 | 84 | 3.50 | 2.0 | 1:1 |
| Synthetic Example 17 | 20 | 1.85 | 2.24 | H₂O | 16 | 64 | 3.50 | 2.5 | 1:1 |
| Synthetic Example 18 | 20 | 1.85 | 2.24 | EtSH | 66 | 84 | 3.50 | 1.5 | 1:1 |

TABLE 2

| | Weight of Intermediate after 1st step (g) | Isocyanate (ml) | DIPEA (g) | CH₃CN (ml) | Ratio of epoxy:alkoxysilyl |
|---|---|---|---|---|---|
| Synthetic Example 2 | 20 | 28.9 | 14.7 | 949 | 1:1 |
| Synthetic Example 3 | 20 | 16.8 | 11.8 | 591 | 2:1 |
| Synthetic Example 4 | 20 | 12.5 | 8.8 | 961 | 2:1 |
| Synthetic Example 5 | 20 | 4.2 | 3.0 | 392 | 2:1 |
| Synthetic Example 6 | 20 | 8.0 | 5.6 | 826 | 2:1 |
| Synthetic Example 7 | 20 | 15.5 | 10.9 | 1278 | 1:1 |
| Synthetic Example 8 | 20 | 15.5 | 10.9 | 1282 | 1:1 |
| Synthetic Example 9 | 20 | 18.7 | 7.6 | 923 | 2:1 |
| Synthetic Example 10 | 20 | 18.6 | 7.5 | 1248 | 2:1 |
| Synthetic Example 11 | 20 | 14.4 | 10.2 | 687 | 2:1 |
| Synthetic Example 16 | 20 | 15.1 | 10.7 | 1310 | 1:1 |
| Synthetic Example 17 | 20 | 30.2 | 21.3 | 1310 | 1:2 |
| Synthetic Example 18 | 20 | 15.1 | 10.7 | 1310 | 1:1 |

Synthetic Example 12

Synthesis of Epoxy Compound Having Alkoxysilyl Group K': Reaction with CH₃CH₂—OH

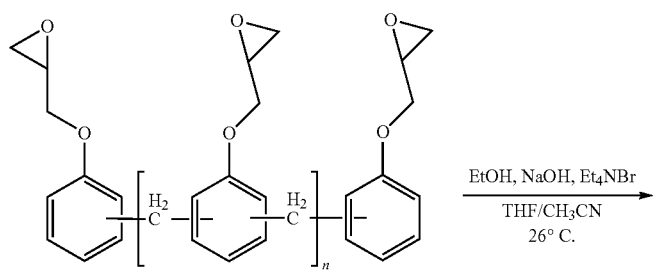

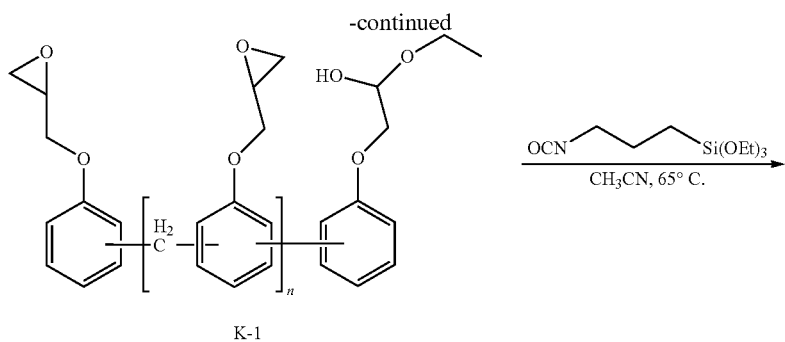

K-1

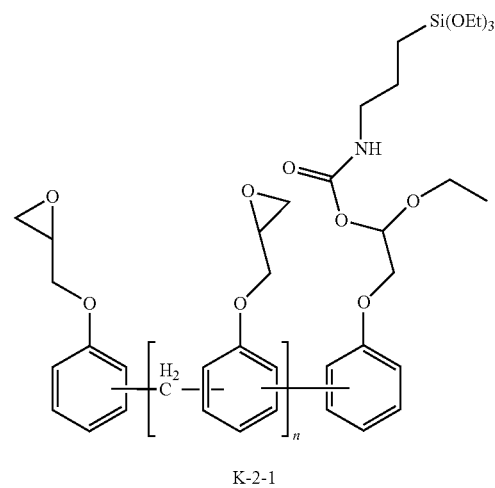

K-2-1

(1) 1st Step 25 g of S.M., 2.43 of NaOH, 2.95 g of tetraethylammonium bromide (NEt₄Br), 93 ml of tetrahydrofuran (THF), 93 ml of CH₃CN and 68 ml of ethanol (EtOH) were added to a two-necked flask at zoom temperature, followed by stirring at 26° C. for 16 hours and 30 minutes. Then, 5 ml of a saturated ammonium chloride (NH₄Cl) solution was added thereto, followed by stirring for 3 minutes. Solvent was removed using a rotary evaporator, and an organic layer was separated by working-up with 400 ml of ethyl acetate (EA) and 300 ml of water. MgSO₄ was added to the separated organic layer to remove residual H₂O and filtered, and solvent was evaporated to produce a ring-opened epoxy intermediate.

NMR after 1st Step $^1$H NMR (400 MHz, CDCl₃): δ=1.18 (m, 10.57 H), 2.60-2.73(m, 6.89H), 3.29-3.32 (m, 3.51H), 3.78-4.17 (m, 35.59H), 4.47-4.49(m, 7.61H), 6.70-7.14(m, 21.68H).

(2) 2nd Step 20 g of the intermediate obtained in the 1st step, 19.0 ml of 3-(triethoxysilyl)propyl isocyanate, 13.4 ml of N,N-diisopropylethylamine (DIPEA), and 130 ml of CH₃CN were added to a two-necked flask, followed by stirring at 65° C. for 20 hours. After completing the reaction, 300 ml of ethyl acetate was added, and a mixture thus obtained was worked-up with a saturated ammonium chloride (NH₄Cl) aqueous solution. An organic layer was separated, and residual H₂O in the organic layer was removed by adding MgSO₄. Organic solvent was removed using a rotary evaporator, and hexane was added to the crude product thus obtained and stored at −15° C. to obtain a precipitate. After removing the supernatant, a process of forming a precipitate by pouring hexane into a precipitate was repeated twice to produce a target product. The concentration ratio of the reactive functional group of the alkoxysilyl epoxy was [epoxy group]:[silyl group]=1:1.

NMR after 2nd Step $^1$H NMR (400 MHz, CDCl₃): δ=0.61 (t, J=8 Hz, 7.33), 1.19-1.22 (m, 43.51H), 1.60 (t, J=8 Hz, 7.71H), 2.60-2.73 (m, 6.89H), 3.15-3.32(m, 10.87H), 3.78-4.18(m, 57.74H), 4.47-4.49 (m, 7.61H), 5.13-5.25(m, 3.67H), 6.70-7.14(m, 21.68H).

Synthetic Example 13

Synthesis of Epoxy Compound Having Alkoxysilyl Group L': Reaction with CH₃CH₂—OH

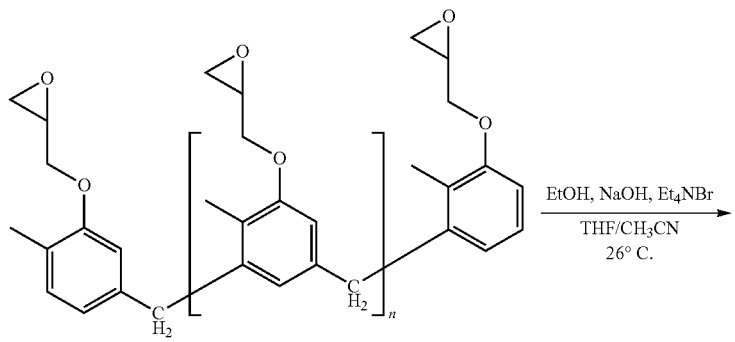

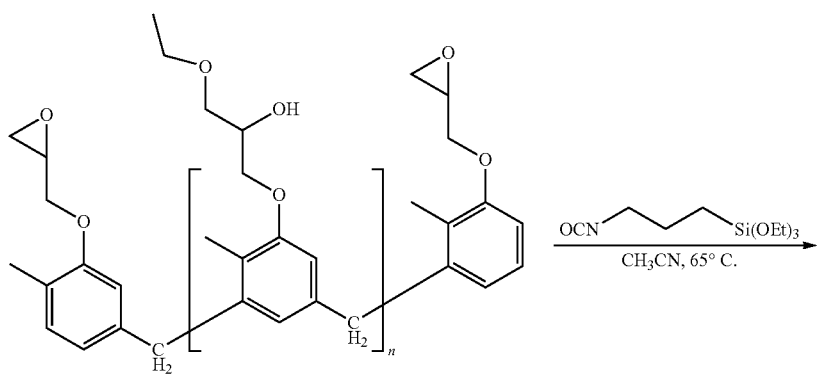

L-1

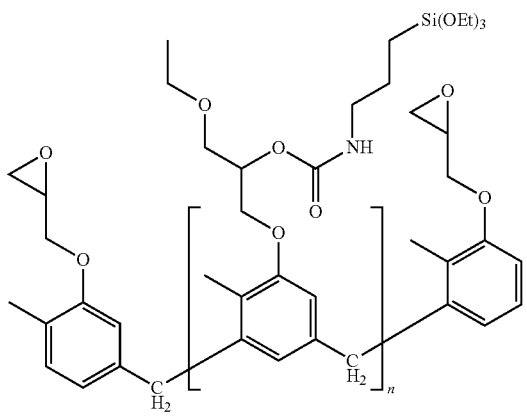

L-2-1

The same procedure as that of Synthetic Example 12 was undertaken. The additive amounts of compounds are shown in Table 3 and Table 4. The concentration ratio of the reactive functional group of the alkoxysilyl epoxy thus obtained was [epoxy group]:[silyl group]=2:1.

NMR after 1$^{st}$ Step $^1$H NMR (400 MHz, CDCl$_3$): δ=1.16(m, 3.42H), 2.12-2.32(m, 3.43H), 2.55-2.91(m, 1.51H), 2.92-3.05(m, 0.68H), 3.42-3.60(m, 1.16H), 3.60-4.12(m, 4.97H), 4.13-4.32(m, 0.37), 6.71-7.04 (m, 3.00H).

NMR after 2$^{nd}$ Step $^1$H NMR (400 MHz, CDCl$_3$): δ=0.51 (m, 0.66H), 1.15(m, 4.02H), 1.57-1.61(m, 0.69H), 2.12-2.32(m, 3.43H), 2.55-2.91(m, 1.51H), 2.92-3.05(m, 0.68H), 3.10-3.36(m, 0.95H), 3.42-3.60(m, 1.16H), 3.60-4.12(m, 5.58H), 4.13-4.32(m, 0.37), 5.11-5.32(m, 0.57H), 6.71-7.04 (m, 3.00H).

Synthetic Example 14
Synthesis of Epoxy Compound Having Alkoxysilyl Group M': Reaction with $CH_3CH_2$—OH
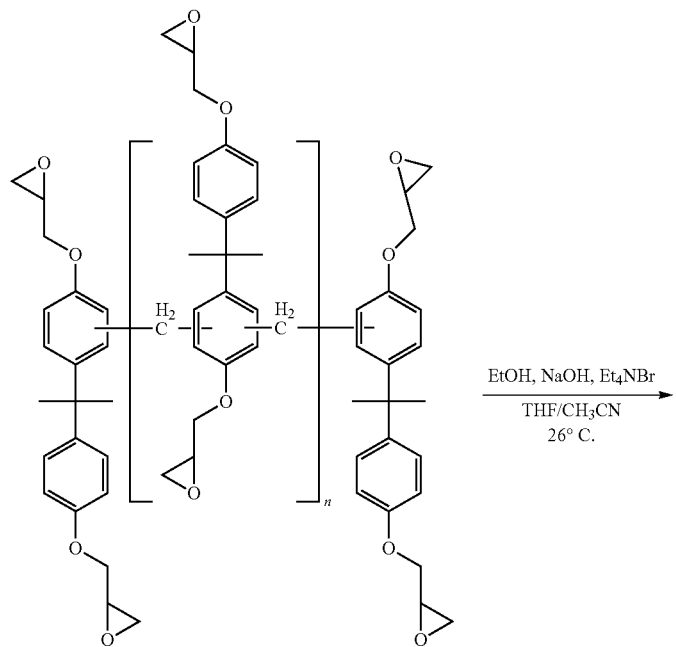
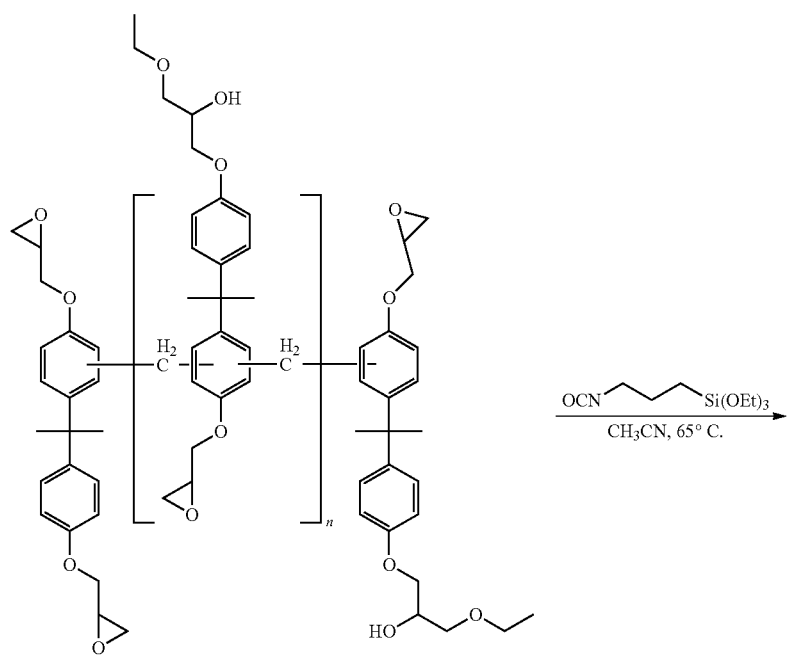
M-1

-continued

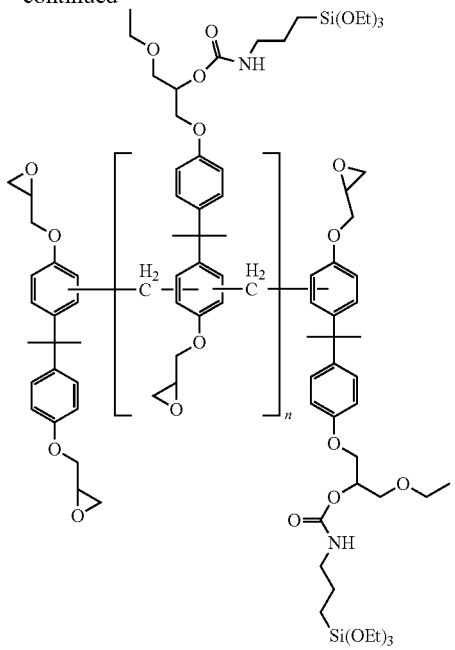

M-2-1

The same procedure as that of Synthetic Example 12 was undertaken. The additive amounts of compounds are shown in Table 3 and Table 4. The concentration ratio of the reactive functional group of the alkoxysilyl epoxy thus obtained was [epoxy group]:[silyl group]=1:1.

NMR after 1st Step $^1$H NMR (400 MHz, CDCl$_3$): δ=1.19 (m, 15.80 H), 1.62(m, 31.92H), 2.58-2.77(m, 10.99H), 3.28-3.34(m, 4.67H), 3.68-4.18(m, 49.42H), 4.46-4.51(m, 11.90H), 6.65-6.72(m, 20.21H), 7.26-7.31(m, 12.68H).

NMR after 2nd Step $^1$H NMR (400 MHz, CDCl$_3$): δ=0.60 (t, J=8 Hz, 10.62H), 1.18-1.22 (m, 62.88H), 1.60-1.63(m, 43.54H), 2.58-2.77(m, 10.99H), 3.15 (t, J=8 Hz, 10.82H), 3.28-3.33(m, 4.67H), 3.67-4.18(m, 80.13H), 4.47-4.51(m, 11.90H), 5.13-5.20(m, 5.32H), 6.65-6.72 (m, 20.21H), 7.26-7.31(m, 12.68H).

Synthetic Example 15

Synthesis of Epoxy Compound Having Alkoxysilyl Group N$^t$: Reaction with CH$_3$CH$_2$—OH

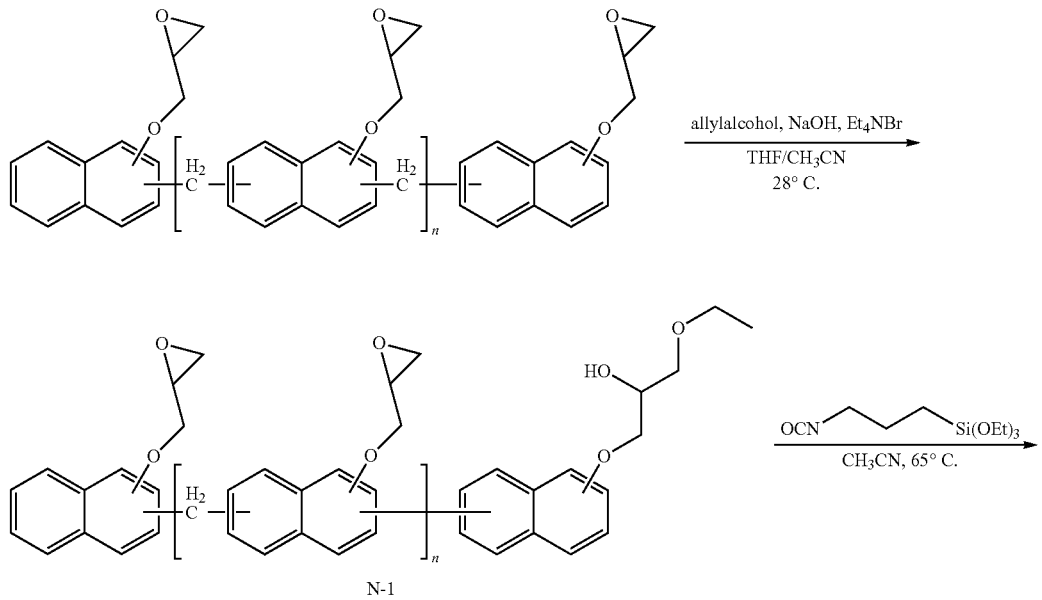

N-1

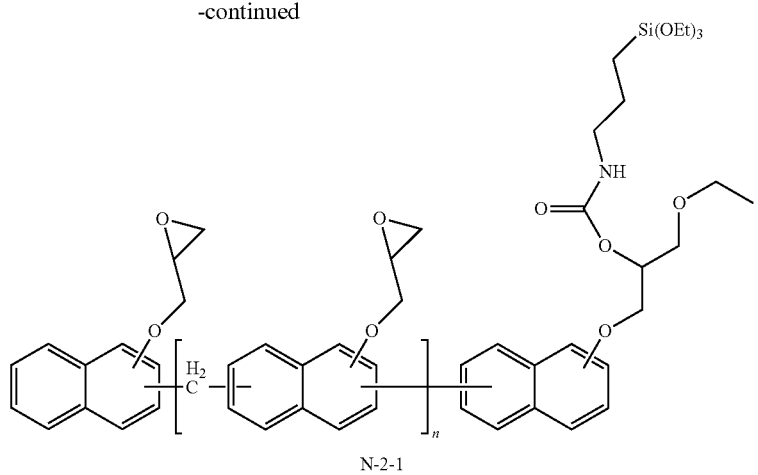

N-2-1

The same procedure as that of Synthetic Example 12 was undertaken. The additive amounts of compounds are shown in Table 3 and Table 4. The concentration ratio of the reactive functional group of the alkoxysilyl epoxy thus obtained was [epoxy group]: [silyl group]=1:1.

NMR after 1st Step $^1$H NMR (400 MHz, CDCl$_3$): δ=1.21 (m, 9.83H), 2.59-2.74(m, 7.41H), 3.28-3.32(m, 3.57H), 3.66-4.42(m, 30.84H), 4.46-4.50(m, 7.44H), 6.55-6.59(m, 4.52H), 7.03-7.39(m, 11.43H), 7.52-7.88 (m, 9.81H), 8.02-8.03 (m, 2.07H).

NMR after 2nd Step $^1$H NMR (400 MHz, CDCl$_3$): δ=0.62 (t, J=8 Hz, 6.99H), 1.21-1.27 (m, 28.62H), 1.63 (t, J=8 Hz, 6.97H), 2.59-2.75 (m, 7.41H), 3.17 (t, J=8 Hz, 7.02H), 3.28-3.32(m, 3.57H), 3.65-4.42(m, 51.72H), 4.46-4.50(m, 7.44H), 5.14-5.40(m, 3.6H), 6.54-6.59(m, 4.52H), 7.02-7.39(m, 11.43H), 7.51-7.88(m, 9.81H), 8.02-8.03(m, 2.07H).

Synthetic Example 16

Synthesis of Tetraphenylethane Epoxy Compound I(2)': Reaction with Et$_3$NH

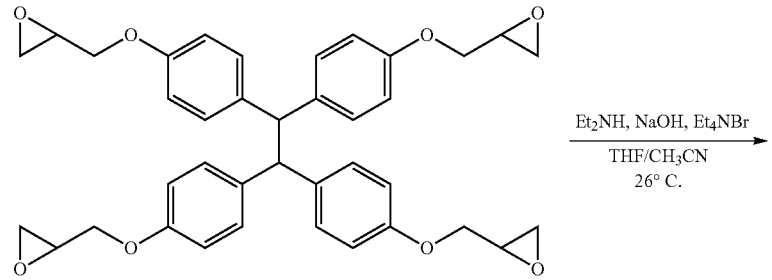

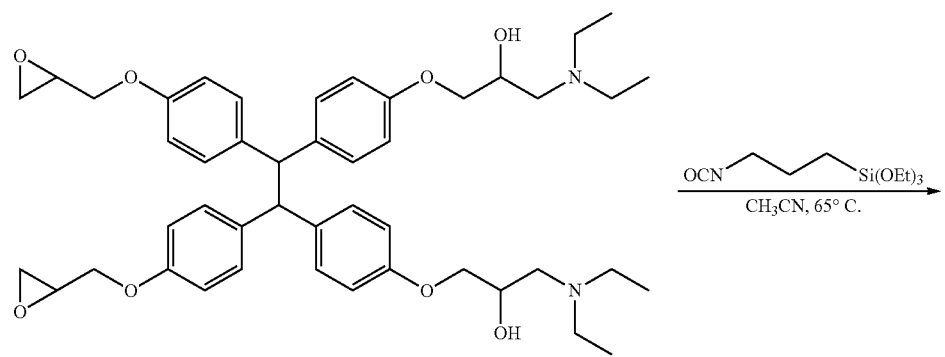

I(2)-1

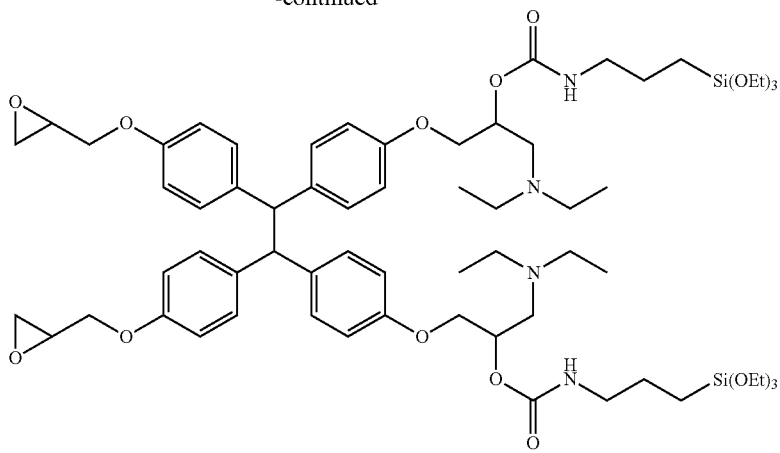

The same procedure as that of Synthetic Example 1 was undertaken except for diethylamine (Et$_2$NH) being used instead of ethanol. The additive amounts of compounds are shown in Table 1 and Table 2. The concentration ratio of the reactive functional group of the alkoxysilyl epoxy thus obtained was [epoxy group]:[silyl group]=1:1.

NMR after 1$^{st}$ Step $^1$H NMR (400 MHz, CDCl$_3$): δ=1.12 (t, 6H), 2.37 (t, 7 Hz, 10H), 2.68 (m, 4H), 2.85 (t, J=4.8 Hz, 2H), 3.20-3.27 (m, 2H), 3.87-4.02 (m, 8H), 4.05-4.13 (m, 2H), 4.55 (s, 2H), 6.67 (d, J=8.4 Hz, 8H), 7.00 (d, J=8.0 Hz, 8H).

NMR after 2$^{nd}$ Step $^1$H NMR (400 MHz, CDCl$_3$): δ=0.57 (m, 4H), 1.12-1.19 (m, 18H), 1.55 (m, 4H), 2.37 (m, 10H), 2.69 (m, 4H), 2.85 (t, J=4.8 Hz, 2H), 3.02-3.06 (m, 4H), 3.20-3.28 (m, 2H), 3.87-4.02 (m, 20H), 4.05-4.13 (m, 2H), 4.55 (s, 2H), 6.67 (d, J=8.4 Hz, 8H), 7.00 (d, J=8.0 Hz, 8H).

Synthetic Example 17

Synthesis of Tetraphenylethane Epoxy Compound I(3)': Reaction with H$_2$O

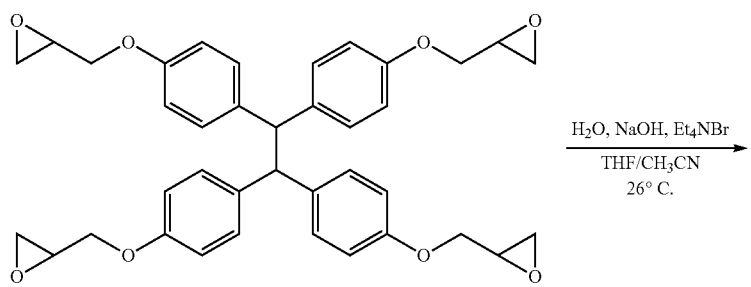

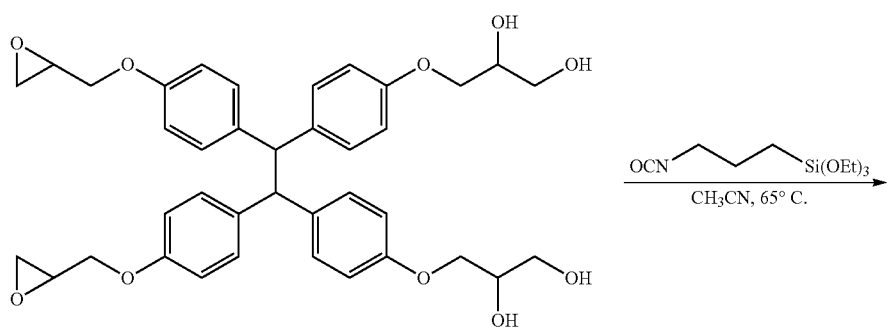

I(3)-1

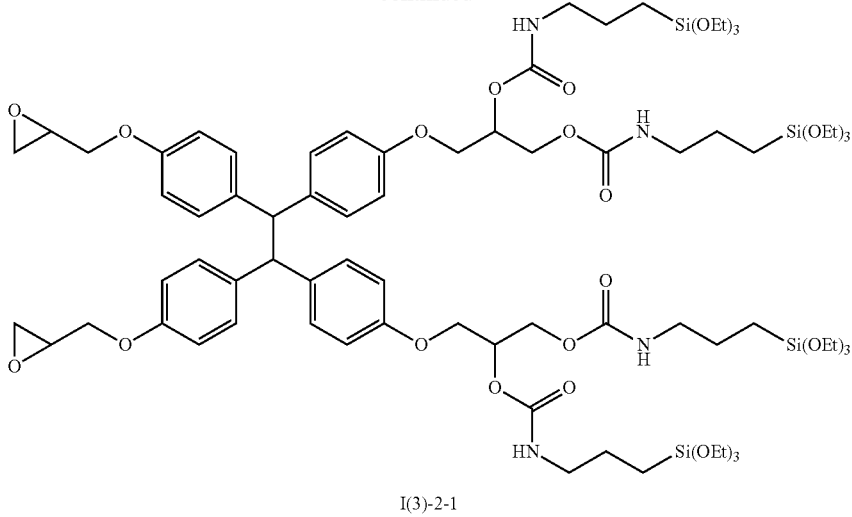

I(3)-2-1

The same procedure as that of Synthetic Example 1 was undertaken except for water (H$_2$O) being used instead of ethanol. The additive amounts of compounds are shown in Table 1 and Table 2. The concentration ratio of the reactive functional group of the alkoxysilyl epoxy thus obtained was [epoxy group]:[silyl group]=1:2.

NMR after 1$^{st}$ Step $^1$H NMR (400 MHz, CDCl$_3$): δ=2.69 (dd, J=4.8 Hz, 2.8 Hz, 2H), 2.85 (t, J=4.8 Hz, 2H), 3.22-3.27 (m, 2H), 3.80-3.84 (m, 2H), 3.88-4.01 (m, 8H), 4.06-4.10 (m, 2H), 4.54 (s, 2H), 6.67 (d, J=8.4 Hz, 8H), 7.00 (d, J=8.0 Hz, 8H).

NMR after 2$^{nd}$ Step $^1$H NMR (400 MHz, CDCl$_3$): δ=0.57 (t, J=8 Hz, 4H), 1.19 (m, 36H), 1.56 (t, J=8 Hz, 8H), 2.67 (dd, J=4.8 Hz, 2.8 Hz, 2H), 2.85 (t, J=4.8 Hz, 2H), 3.07 (t, J=8 Hz, 8H), 3.22-3.27 (m, 2H), 3.50-3.62 (m, 2H), 3.78-3.84 (m, 2H), 3.84-4.01 (m, 32H), 4.04-4.12(m, 2H), 4.45 (s, 2H), 5.05-5.29 (m, 4H), 6.67 (d, J=8.4 Hz, 8H), 7.00 (d, J=8.0 Hz, 8H).

Synthetic Example 18

Synthesis of Tetraphenylethane Epoxy Compound I(4)': Reaction with CH$_3$CH$_2$—SH

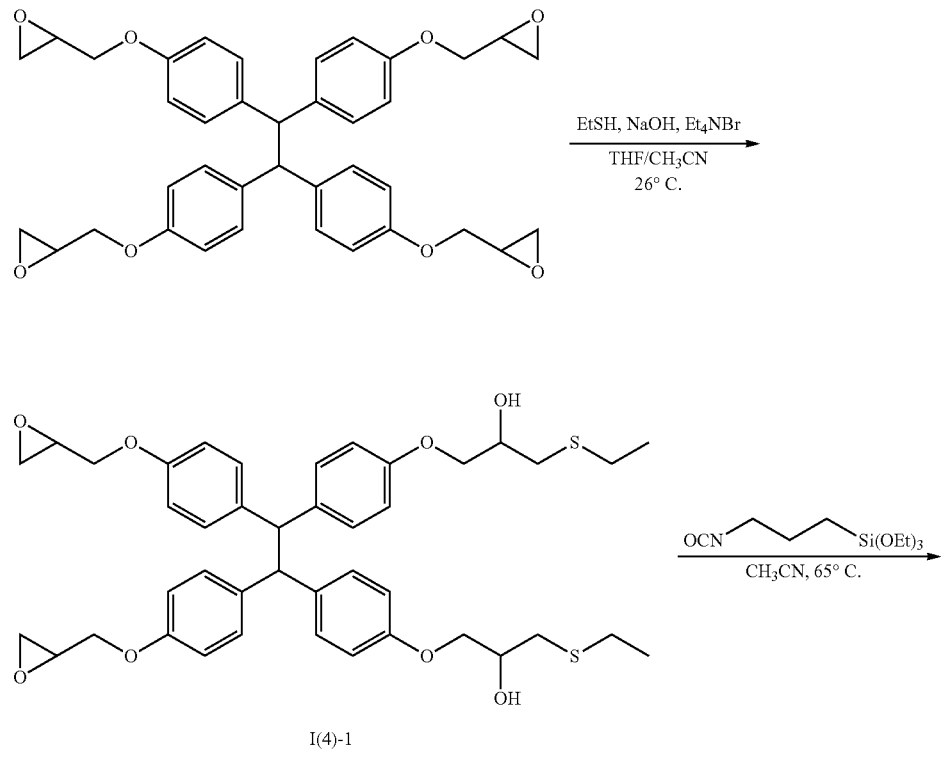

I(4)-1

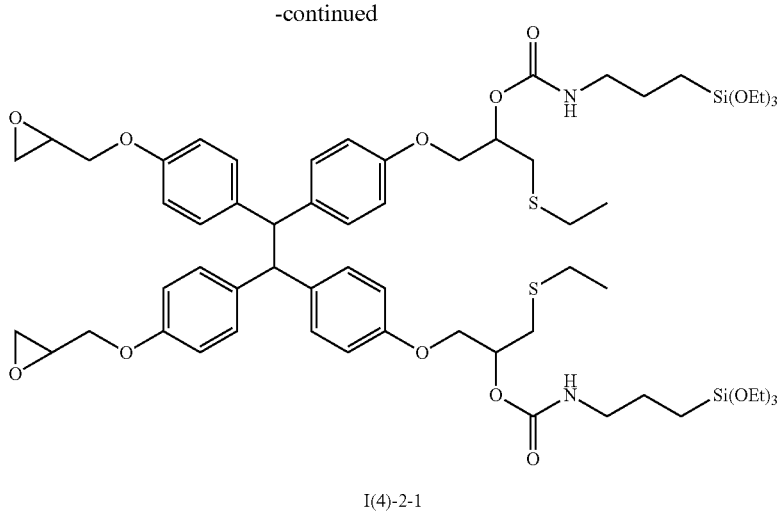

I(4)-2-1

The same procedure as that of Synthetic Example 1 was undertaken except for $CH_3CH_2$—SH being used instead of ethanol. The additive amounts of compounds are shown in Table 1 and Table 2. The concentration ratio of the reactive functional group of the alkoxysilyl epoxy thus obtained was [epoxy group]:[silyl group]=1:1.

NMR after $1^{st}$ Step $^1$H NMR (400 MHz, $CDCl_3$): δ=1.19 (t, 6H), 2.41-2.44 (m, 6H), 2.66-2.69 (m, 4H), 2.84 (t, J=4.8 Hz, 2H), 3.20-3.27 (m, 2H), 3.87-4.01 (m, 8H), 4.05-4.13 (m, 2H), 4.55 (s, 2H), 6.67 (d, J=8.4 Hz, 8H), 7.00 (d, J=8.0 Hz, 8H).

NMR after $2^{nd}$ Step $^1$H NMR (400 MHz, $CDCl_3$): δ=0.57 (m, 4H), 1.12-1.19 (m, 24H), 1.55 (m, 4H), 2.41-2.43 (m, 6H), 2.67-2.70 (m, 4H), 2.84 (t, J=4.8 Hz, 2H), 3.04-3.06 (m, 4H), 3.20-3.28 (m, 2H), 3.87-4.03 (m, 20H), 4.05-4.13 (m, 2H), 4.55 (s, 2H), 5.01-5.15 (m, 2H), 6.67 (d, J=8.4 Hz, 8H), 7.00 (d, J=8.0 Hz, 8H).

TABLE 3

| | Epoxy compound (g) | NaOH (g) | $Et_4NBr$ (g) | THF (ml) | $CH_3CN$ (ml) | Time (h) | Ratio of epoxy: alkoxysilyl |
|---|---|---|---|---|---|---|---|
| Synthetic Example 13 | 20 | 1.33 | 1.61 | 51 | 51 | 8 | 2:1 |
| Synthetic Example 14 | 20 | 1.13 | 1.37 | 43 | 43 | 16.5 | 1:1 |
| Synthetic Example 15 | 20 | 1.40 | 1.70 | 54 | 54 | 16.5 | 1:1 |

TABLE 4

| | Weight of Intermediate after $1^{st}$ step (g) | Isocyanate (ml) | DIPEA (g) | $CH_3CN$ (ml) | Ratio of epoxy:alkoxysilyl |
|---|---|---|---|---|---|
| Synthetic Example 13 | 20 | 7.8 | 5.5 | 211 | 2:1 |
| Synthetic Example 14 | 20 | 9.8 | 6.9 | 253 | 1:1 |
| Synthetic Example 15 | 20 | 11.9 | 8.4 | 208 | 1:1 |

Synthetic Example 19

Synthesis of Naphthalene Epoxy Compound A-2: Reaction with $CH_3CH_2$—OH, $HSi(OEt)_3$

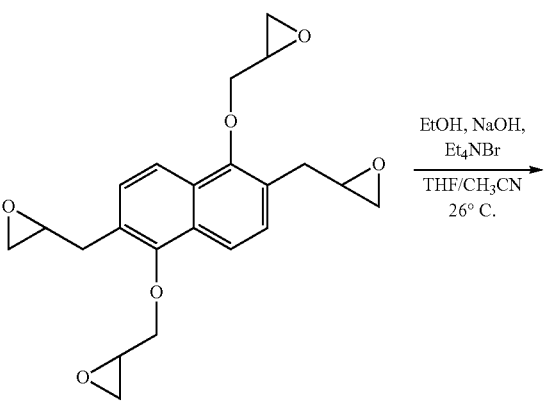

-continued

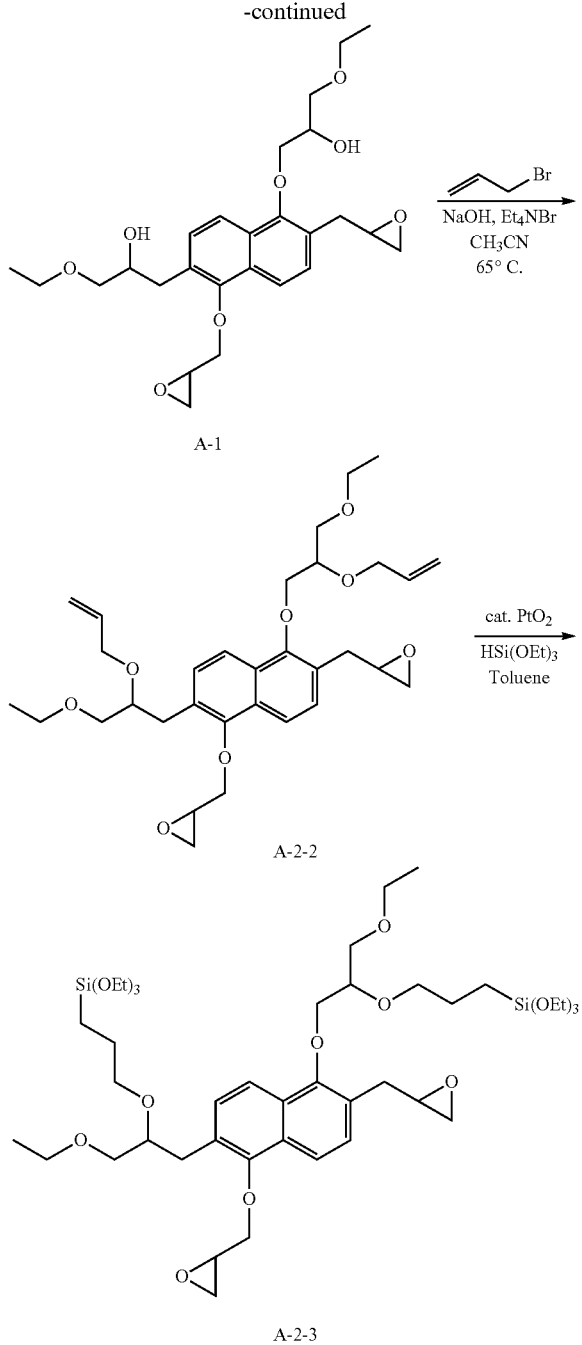

(1) 1st Step

Compound of formula A-1 was synthesized by conducting the same procedure described in the 1st step reaction of Synthetic Example 2 (A').

(2) 2nd Step 20 g of the intermediate obtained in the 1st step, 6.2 ml of allyl bromide, 2.87 g of NaOH, 2.3 g of tetraethylammonium bromide (NEt$_4$Br) and 72 ml of CH$_3$CN were added to a two-necked flask, followed by stirring at 65° C. for 20 hours. After completing the reaction, 300 ml of ethyl acetate was added, and the mixture thus obtained was worked-up with water. An organic layer was separated, and MgSO$_4$ was added to the organic layer to remove residual H$_2$O. Organic solvent was removed using a rotary evaporator to produce A-2-2.

NMR after 2nd Step $^1$H NMR (400 MHz, CDCl$_3$): δ=1.17 (t, 8 Hz, 6H), 2.52-2.57 (m, 1H), 2.61-2.66 (m, 2H) 2.73-2.81 (m, 3H), 2.90-2.93 (m, 2H), 3.16-3.18 (m, 1H), 3.35-3.37 (m, 1H), 3.80-4.13 (m, 17H), 4.22-4.25 (m, 1H), 5.20-5.27 (m, 4H), 5.87-6.00 (m, 2H), 7.28 (d, J=8.5 Hz, 2H), 7.75 (d, J=8.5 Hz, 2H).

(3) 3rd Step 10 g of Intermediate A-2 obtained in the 1st step, 135 mg of PtO$_2$, 5.37 g of triethoxysilane and 150 ml of toluene were added to a two-necked flask, followed by stirring at room temperature for 5 minutes. The temperature was elevated to 80° C., and heating and stirring was performed for 24 hours. After completing the reaction, the reactant was cooled to room temperature and filtered using a celite filter to remove an inorganic material. Toluene was removed by evaporation and was completely dried using a vacuum pump to produce a target product of Compound A-2-3 having an alkoxysilyl group in which the ratio of epoxy group:alkoxysilyl group was 1:1. The concentration ratio of the reactive functional group of the alkoxysilyl epoxy thus obtained was [epoxy group]:[silyl group]=1:1.

NMR after 3rd Step $^1$H NMR (400 MHz, CDCl$_3$): δ=0.60 (t, J=4 Hz, 4H), 1.21 (m, 24H), 1.57-1.61 (m, 4H), 2.52-2.57 (m, 1H), 2.61-2.66 (m, 2H) 2.73-2.81 (m, 3H), 2.90-2.93 (m, 2H), 3.16-3.18 (m, 1H), 3.24-3.28 (m, 4H), 3.35-3.37 (m, 1H), 3.78-4.13 (m, 25H), 4.22-4.25 (m, 1H), 7.28 (d, J=8.5 Hz, 2H), 7.75 (d, J=8.5 Hz, 2H).

Expected Synthetic Examples

Expected Synthetic Example 1

Synthesis of Naphthalene Epoxy Compound B-2: Reaction with CH$_3$CH$_2$—OH, HSi(OEt)$_3$

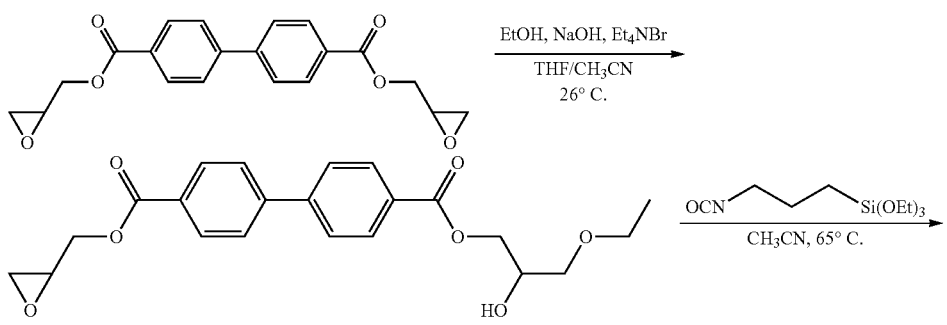

-continued

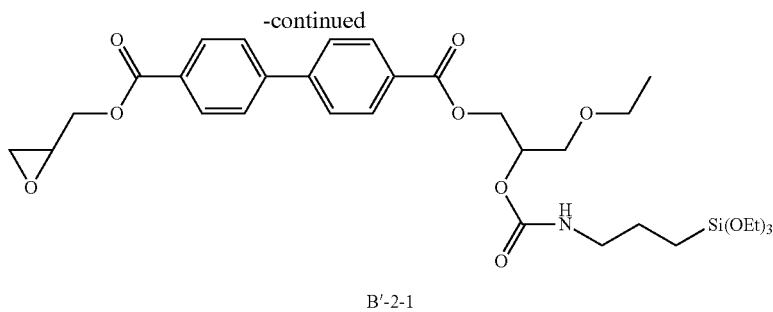

B'-2-1

(1) 1st Step 20 g of SM, 2.93 g of NaOH, 3.56 g of tetraethylammonium bromide (NEt₄Br), 71 ml of THF, 71 ml of CH₃CN and 82 ml of ethanol (EtOH) are added to a two-necked flask, followed by stirring at 26° C. for 2 hours and 30 minutes. Then, 5 ml of a saturated ammonium chloride (NH₄Cl) solution is added thereto, followed by stirring for 3 minutes. Solvent is removed using a rotary evaporator, the residue is worked-up using 400 ml of ethyl acetate (EA) and 300 ml of water to separate an organic layer. After removing H₂O by adding MgSO₄ to the organic layer thus separated, the product is filtered, and solvent is evaporated to obtain a ring-opened epoxy intermediate.

Expected NMR after 1st Step $^1$H NMR (400 MHz, CDCl₃): δ=1.15 (t, 8 Hz, 3H), 2.43-2.45 (m, 1H), 2.61-2.66 (m, 1H) 3.13-3.17 (m, 1H), 3.38-3.45 (m, 1H), 3.63-3.70 (m, 1H), 3.88 (q, 2H), 4.22-4.25 (m, 2H), 4.39-4.50 (m, 3H), 7.75 (d, J=8.5 Hz, 4H), 7.95 (d, J=8.5 Hz, 4H).

(2) 2st Step 20 g of the intermediate obtained in the 1st step, 12.4 ml of 3-(triethoxysilyl)propyl isocyanate, 8.7 ml of N,N-diisopropylethylamine (DIPEA) and 801 ml of CH₃CN are added to a two-necked flask, followed by stirring at 65° C. for 20 hours. After completing the reaction, 300 ml of ethyl acetate is added, and the mixture thus obtained is worked-up using a saturated ammonium chloride (NH₄Cl) aqueous solution. An organic layer is separated, and MgSO₄ is added to the organic layer to remove residual H₂O. Organic solvent is removed using a rotary evaporator, and hexane is added to the crude product thus obtained, followed by storing at −15° C. to obtain a precipitate. The supernatant is removed, and a process of pouring hexane into a precipitate to produce a precipitate is repeated twice to obtain a target product. The concentration ratio of the reactive functional group of an alkoxysilyl epoxy is expected to be [epoxy group]:[silyl group]=1:1.

Expected NMR after 2nd Step $^1$H NMR (400 MHz, CDCl₃): δ=0.60 (t, 8 Hz, 2H), 1.08-1.25 (m, 12H), 1.43-1.70 (m, 2H), 2.43-2.45 (m, 1H), 2.61-2.66 (m, 1H) 3.05-3.17 (m, 3H), 3.38-3.45 (m, 1H), 3.62-3.70 (m, 7H), 3.88 (q, 2H), 4.22-4.25 (m, 2H), 4.39-4.50 (m, 3H), 4.93-5.10 (m, 1H), 7.75 (d, J=8.5 Hz, 4H), 7.95 (d, J=8.5 Hz, 4H).

Evaluation of Physical Properties: Manufacturing of Cured Product and Evaluation of Heat Resistance 1. Manufacturing of Epoxy Composite (1) Manufacturing of Epoxy Glass Fiber Composite (Cured Product)

An epoxy compound, a curing agent and a curing catalyst were dissolved in methyl ethyl ketone according to the component ratios illustrated in Tables 5 to 7 so that a solid content was 40 wt % and mixed to obtain a homogeneous solution. A glass fiber (glass fiber fabric by Nittobo Co, T-glass) was impregnated with the mixture thus obtained to manufacture a glass fiber composite comprising an epoxy compound. Then, the composite was inserted in a vacuum oven heated to 100° C. to remove solvents, and was cured in a hot press hpr heated to 120° C. at 120° C. for 2 hours, at 180° C. for 2 hours and >200° C. for 2 hours to obtain a glass fiber composite film (4 mm×16 mm×0.1 mm). While manufacturing the composite film, the amount of the resin of the composite film was controlled according to the pressure of a press and the viscosity of the resin. The amount of the resin in the composite film is illustrated in the following Tables 5 to 7.

In addition, in the case that a composition for a glass fiber composite comprises silica, an epoxy compound and a silica slurry (70 wt % of solid content, 2-methoxyethanol solvent, 1 μm of silica average size) were dissolved in methyl ethyl ketone according to the component ratios illustrated in the following Tables 5 to 7 so that a solid content was 40 wt %. The mixture thus obtained was mixed in a rate of 1,500 rpm for 1 hour, and a curing agent was added, followed by further mixing for 50 minutes. Finally, a curing catalyst and was added and mixed for 10 minutes further to obtain an epoxy mixture. A glass fiber composite was manufactured by immersing a glass fiber (glass fiber fabric by Nittobo Co., T-glass) with the epoxy mixture. Then, the same curing process was performed under the same conditions as described above to manufacture a composite film.

(2) Manufacturing of Epoxy Filler Composite (Cured Product)

Epoxy compound and a silica slurry (70 wt % of solid content, 2-methoxyethanol solvent, 1 μm of silica average size) were dissolved in methyl ethyl ketone according to the component ratios illustrated in the following Tables 8 to 10 so that a solid content was 40 wt %. The mixture thus obtained was mixed in a rate of 1,500 rpm for 1 hour, and the curing agent was added, followed by further mixing for 50 minutes. Finally, the curing catalyst was added and mixed for 10 minutes further to obtain an epoxy mixture. Then, the mixture was inserted into a vacuum oven heated to 100° C. to remove solvents, and was cured in a hot press preheated to 120° C., at 120° C. for 2 hours, at 180° C. for 2 hours and at >200° C. for 2 hours to obtain an epoxy filler (inorganic particles) composite (5 mm×5 mm×3 mm).

2. Evaluation of Heat Resistant Physical Properties

The dimensional changes with respect to the temperature of the cured products according to the examples and comparative examples illustrated in the following Tables 5 to 10 were evaluated using a Thermo-mechanical analyzer and are illustrated in the following Tables. The samples of the epoxy glass fiber composite films were manufactured to have a size of 4×16×0.1 (mm³), and the samples of the filler composites were manufactured to have a size of 5×5×3 (mm³).

Tables 5 to 7 are illustrated for the epoxy glass fiber composites, and Tables 8 to 10 are illustrated for the epoxy filler composites.

TABLE 5

| | Epoxy compound (Synthetic Example No.) | | Example 1 | Example 2 | Example 3 | Example 4 | Example 5 | Example 6 | Example 7 | Example 8 |
|---|---|---|---|---|---|---|---|---|---|---|
| Epoxy formulation (g) | Epoxy | Synthetic Example 1 | 5.00 | | | | | | | |
| | | Synthetic Example 2 | | 5.00 | | | | | | |
| | | Synthetic Example 3 | | | 5.00 | | | | | |
| | | Synthetic Example 4 | | | | 5.00 | | | | |
| | | Synthetic Example 5 | | | | | 5.00 | | | |
| | | Synthetic Example 6 | | | | | | 5.00 | | |
| | | Synthetic Example 7 | | | | | | | 5.00 | |
| | | Synthetic Example 8 | | | | | | | | 5.00 |
| | | Synthetic Example 9 | | | | | | | | |
| | | Synthetic Example 10 | | | | | | | | |
| | | Synthetic Example 11 | | | | | | | | |
| | | Synthetic Example 12 | | | | | | | | |
| | | Synthetic Example 13 | | | | | | | | |
| | | Synthetic Example 14 | | | | | | | | |
| | | Synthetic Example 15 | | | | | | | | |
| | | Synthetic Example 16 | | | | | | | | |
| | | Synthetic Example 17 | | | | | | | | |
| | | Synthetic Example 18 | | | | | | | | |
| | | Synthetic Example 19 | | | | | | | | |
| | | Synthetic Example 20 | | | | | | | | |
| | | TMTE[1] | | | | | | | | |
| | | DGEBA[2] | | | | | | | | |
| | | EOCN[3] | | | | | | | | |
| | | polydis[4] | | | | | | | | |
| | | HF-1M[5] | | | | | | | | |
| | | TPP[6] | | | | | | | | |
| | | 2E4MZ[7] | 0.25 | 0.25 | 0.25 | 0.25 | 0.25 | 0.25 | 0.25 | 0.25 |
| | | Polyvinyl acetal | 0.56 | 0.56 | 0.56 | 0.56 | 0.56 | 0.56 | 0.56 | 0.56 |
| | | Silica | 10.79 | 10.79 | 10.79 | 10.79 | 10.79 | 10.79 | 10.79 | 10.79 |
| | | Glass fiber type | T | T | T | T | T | T | T | T |
| | | Resin amount (wt %) | 50% | 49% | 52% | 51% | 51% | 49% | 52% | 53% |
| | | Curing temp | 120-180-290 | 120-180-290 | 120-180-290 | 120-180-290 | 120-180-290 | 120-180-290 | 120-180-290 | 120-180-290 |
| Heat resistance | CTE (ppm/° C.) | $\alpha_1$ (T < Tg) | 2.8 | 3.1 | 3.9 | 4.0 | 3.5 | 3.7 | 3.5 | 4.0 |
| | Tg (° C.) | | TgL | TgL | TgL | TgL | TgL | TgL | TgL | TgL |

TABLE 6

| | Epoxy compound (Synthetic Example No.) | | Example 9 | Example 10 | Example 11 | Example 12 | Example 13 | Example 14 | Example 15 | Example 16 |
|---|---|---|---|---|---|---|---|---|---|---|
| Epoxy formulation (g) | Epoxy | Synthetic Example 1 | | | | | | | | |
| | | Synthetic Example 2 | | | | | | | | |
| | | Synthetic Example 3 | | | | | | | | |
| | | Synthetic Example 4 | | | | | | | | |
| | | Synthetic Example 5 | | | | | | | | |

TABLE 6-continued

| Epoxy compound (Synthetic Example No.) | | | Example 9 | Example 10 | Example 11 | Example 12 | Example 13 | Example 14 | Example 15 | Example 16 |
|---|---|---|---|---|---|---|---|---|---|---|
| | | Synthetic Example 6 | | | | | | | | |
| | | Synthetic Example 7 | | | | | | | | |
| | | Synthetic Example 8 | | | | | | | | |
| | | Synthetic Example 9 | 5.00 | | | | | | | |
| | | Synthetic Example 10 | | 5.00 | | | | | | |
| | | Synthetic Example 11 | | | 5.00 | | | | | |
| | | Synthetic Example 12 | | | | 5.00 | | | | |
| | | Synthetic Example 13 | | | | | 5.00 | | | |
| | | Synthetic Example 14 | | | | | | 5.00 | | |
| | | Synthetic Example 15 | | | | | | | 5.00 | |
| | | Synthetic Example 16 | | | | | | | | 5.00 |
| | | Synthetic Example 17 | | | | | | | | |
| | | Synthetic Example 18 | | | | | | | | |
| | | Synthetic Example 19 | | | | | | | | |
| | | Synthetic Example 20 | | | | | | | | |
| | | TMTE[(1)] | | | | | | | | |
| | | DGEBA[(2)] | | | | | | | | |
| | | EOCN[(3)] | | | | | | | | |
| | | polydis[(4)] | | | | | | | | |
| | | HF-1M[(5)] | | | | | | | | |
| | | TPP[(6)] | | | | | | | | |
| | | 2E4MZ[(7)] | 0.25 | 0.25 | 0.25 | 0.25 | 0.25 | 0.25 | 0.25 | 0.25 |
| | | Polyvinyl acetal | 0.56 | 0.56 | 0.56 | 0.56 | 0.56 | 0.56 | 0.56 | 0.56 |
| | | Silica | 10.79 | 10.79 | 10.79 | 10.79 | 10.79 | 10.79 | 10.79 | 10.79 |
| | | Glass fiber type | T | T | T | T | T | T | T | T |
| | | Resin amount (wt %) | 50% | 51% | 50% | 52% | 52% | 50% | 52% | 51% |
| | | Curing temp | 120-180-290 | 120-180-290 | 120-180-290 | 120-180-290 | 120-180-290 | 120-180-290 | 120-180-290 | 120-180-290 |
| Heat resistance | CTE (ppm/° C.) | $\alpha_1$ (T < Tg) | 3.7 | 3.8 | 3.7 | 3.5 | 4.3 | 4.0 | 3.6 | 3.4 |
| | Tg (° C.) | | TgL | TgL | TgL | TgL | TgL | TgL | TgL | TgL |

TABLE 7

| | Epoxy compound (Synthetic Example No.) | | Example 17 | Example 18 | Example 19 | Comparative Example 1 | Comparative Example 2 | Comparative Example 3 |
|---|---|---|---|---|---|---|---|---|
| Epoxy formulation (g) | Epoxy | Synthetic Example 1 | | | | | | |
| | | Synthetic Example 2 | | | | | | |
| | | Synthetic Example 3 | | | | | | |
| | | Synthetic Example 4 | | | | | | |
| | | Synthetic Example 5 | | | | | | |
| | | Synthetic Example 6 | | | | | | |
| | | Synthetic Example 7 | | | | | | |
| | | Synthetic Example 8 | | | | | | |
| | | Synthetic Example 9 | | | | | | |
| | | Synthetic Example 10 | | | | | | |

TABLE 7-continued

| Epoxy compound (Synthetic Example No.) | | Example 17 | Example 18 | Example 19 | Comparative Example 1 | Comparative Example 2 | Comparative Example 3 |
|---|---|---|---|---|---|---|---|
| | Synthetic Example 11 | | | | | | |
| | Synthetic Example 12 | | | | | | |
| | Synthetic Example 13 | | | | | | |
| | Synthetic Example 14 | | | | | | |
| | Synthetic Example 15 | | | | | | |
| | Synthetic Example 16 | | | | | | |
| | Synthetic Example 17 | 5.00 | | | | | |
| | Synthetic Example 18 | | 5.00 | | | | |
| | Synthetic Example 19 | | | 5.00 | | | |
| | Synthetic Example 20 | | | | | | |
| | TMTE[1] | | | | 5.00 | | |
| | DGEBA[2] | | | | | 5.00 | |
| | EOCN[3] | | | | | | 5.00 |
| | polydis[4] | | | | | | |
| | HF-1M[5] | | | | 3.49 | 2.84 | 2.34 |
| | TPP[6] | | | | 0.05 | 0.05 | 0.03 |
| | 2E4MZ[7] | 0.25 | 0.25 | 0.25 | | | |
| | Polyvinyl acetal | 0.56 | 0.56 | 0.56 | | | |
| | Silica | 10.79 | 10.79 | 10.79 | | | |
| | Glass fiber type | T | T | T | E | E | E |
| | Resin amount (wt %) | 48% | 51% | 52% | 43% | 40% | 40% |
| | Curing temp | 120-180-290 | 120-180-290 | 120-180-290 | 120-180-290 | 120-180-290 | 120-180-290 |
| Heat resistance | CTE (ppm/°C.) $\alpha_1$ (T < Tg) | 3.2 | 3.5 | 3.0 | 15 | 15.8 | 15 |
| | Tg (°C.) | TgL | TgL | TgL | 170 | 150 | 150 |

TABLE 8

| No. | Epoxy compound (Synthetic Example No.) | | Example 20 | Example 21 | Example 22 | Example 23 | Example 24 | Example 25 | Example 26 | Example 27 |
|---|---|---|---|---|---|---|---|---|---|---|
| Epoxy formulation (g) | Epoxy | Synthetic Example 1 | 4.00 | | | | | | | |
| | | Synthetic Example 2 | | 4.00 | | | | | | |
| | | Synthetic Example 3 | | | 4.00 | | | | | |
| | | Synthetic Example 4 | | | | 4.00 | | | | |
| | | Synthetic Example 5 | | | | | 4.00 | | | |
| | | Synthetic Example 6 | | | | | | 4.00 | | |
| | | Synthetic Example 7 | | | | | | | 4.00 | |
| | | Synthetic Example 8 | | | | | | | | 4.00 |
| | | Synthetic Example 9 | | | | | | | | |
| | | Synthetic Example 10 | | | | | | | | |
| | | Synthetic Example 11 | | | | | | | | |
| | | Synthetic Example 12 | | | | | | | | |
| | | Synthetic Example 13 | | | | | | | | |
| | | Synthetic Example 14 | | | | | | | | |
| | | Synthetic Example 15 | | | | | | | | |

TABLE 8-continued

| No. | Epoxy compound (Synthetic Example No.) | | Example 20 | Example 21 | Example 22 | Example 23 | Example 24 | Example 25 | Example 26 | Example 27 |
|---|---|---|---|---|---|---|---|---|---|---|
| | Synthetic Example 16 | | | | | | | | | |
| | Synthetic Example 17 | | | | | | | | | |
| | Synthetic Example 18 | | | | | | | | | |
| | Synthetic Example 19 | | | | | | | | | |
| | Synthetic Example 20 | | | | | | | | | |
| | TMTE[1] | | | | | | | | | |
| | DGEBA[2] | | | | | | | | | |
| | EOCN[3] | | | | | | | | | |
| | polydis[4] | | 0.49 | 0.49 | 0.49 | 0.49 | 0.49 | 0.49 | 0.49 | 0.49 |
| | HR5 (PVA) | | 0.99 | 0.99 | 0.99 | 0.99 | 0.99 | 0.99 | 0.99 | 0.99 |
| | HF-1M[5] | | | | | | | | | |
| | TPP[6] | | | | | | | | | |
| | 2E4MZ[7] | | 0.22 | 0.31 | 0.22 | 0.31 | 0.31 | 0.22 | 0.22 | 0.22 |
| | Silica | | 22.80 | 23.16 | 22.80 | 23.16 | 23.16 | 22.80 | 22.80 | 22.80 |
| | Filler amount (w %) | | 80 | 80 | 80 | 80 | 80 | 80 | 80 | 80 |
| | Curing temp | | 120-180-230-290 | 120-180-230-290 | 120-180-230-290 | 120-180-230-290 | 120-180-230-290 | 120-180-230-290 | 120-180-230-290 | 120-180-230-290 |
| Heat resistance | CTE (ppm/° C.) | $\alpha_1$ (T < Tg) | 6.17 | 6.86 | 8.25 | 8.01 | 6.54 | 7.50 | 8.92 | 9.01 |
| | Tg (° C.) | | Tgl | Tgl | Tgl | Tgl | Tgl | Tgl | Tgl | Tgl |

TABLE 9

| No. | Epoxy compound (Synthetic Example No.) | | | Example 28 | Example 29 | Example 30 | Example 31 | Example 32 | Example 33 | Example 34 | Example 35 |
|---|---|---|---|---|---|---|---|---|---|---|---|
| Epoxy formulation (g) | Epoxy | Synthetic Example 1 | | | | | | | | | |
| | | Synthetic Example 2 | | | | | | | | | |
| | | Synthetic Example 3 | | | | | | | | | |
| | | Synthetic Example 4 | | | | | | | | | |
| | | Synthetic Example 5 | | | | | | | | | |
| | | Synthetic Example 6 | | | | | | | | | |
| | | Synthetic Example 7 | | | | | | | | | |
| | | Synthetic Example 8 | | | | | | | | | |
| | | Synthetic Example 9 | | 4.00 | | | | | | | |
| | | Synthetic Example 10 | | | 4.00 | | | | | | |
| | | Synthetic Example 11 | | | | 4.00 | | | | | |
| | | Synthetic Example 12 | | | | | 4.00 | | | | |
| | | Synthetic Example 13 | | | | | | 4.00 | | | |
| | | Synthetic Example 14 | | | | | | | 4.00 | | |
| | | Synthetic Example 15 | | | | | | | | 4.00 | |
| | | Synthetic Example 16 | | | | | | | | | 4.00 |
| | | Synthetic Example 17 | | | | | | | | | |
| | | Synthetic Example 18 | | | | | | | | | |

TABLE 9-continued

| No. | Epoxy compound (Synthetic Example No.) | | Example 28 | Example 29 | Example 30 | Example 31 | Example 32 | Example 33 | Example 34 | Example 35 |
|---|---|---|---|---|---|---|---|---|---|---|
| | Example 19 Synthetic Example 20 TMTE[1] DGEBA[2] EOCN[3] | | | | | | | | | |
| | polydis[4] | | 0.49 | 0.49 | 0.49 | 0.49 | 0.49 | 0.49 | 0.49 | 0.49 |
| | HR5 (PVA) | | 0.99 | 0.99 | 0.99 | 0.99 | 0.99 | 0.99 | 0.99 | 0.99 |
| | HF-1M[5] TPP[6] | | | | | | | | | |
| | 2E4MZ[7] | | 0.22 | 0.22 | 0.22 | 0.22 | 0.22 | 0.22 | 0.22 | 0.22 |
| | Silica | | 22.80 | 22.80 | 22.80 | 22.80 | 22.80 | 22.80 | 22.80 | 22.80 |
| | Filler amount (w %) | | 80 | 80 | 80 | 80 | 80 | 80 | 80 | 80 |
| | Curing temp | | 120-180-230-290 | 120-180-230-290 | 120-180-230-290 | 120-180-230-290 | 120-180-230-290 | 120-180-230-290 | 120-180-230-290 | 120-180-230-290 |
| Heat resistance | CTE (ppm/° C.) | $\alpha_1$ (T < Tg) | 6.72 | 5.99 | 7.80 | 7.23 | 8.03 | 8.00 | 8.27 | 8.67 |
| | Tg (° C.) | | Tgl | Tgl | Tgl | Tgl | Tgl | Tgl | Tgl | Tgl |

TABLE 10

| No. | Epoxy compound (Synthetic Example No.) | | Example 36 | Example 37 | Example 38 | Comparative Example 4 | Comparative Example 5 | Comparative Example 6 |
|---|---|---|---|---|---|---|---|---|
| Epoxy formulation (g) | Epoxy | Synthetic Example 1 | | | | | | |
| | | Synthetic Example 2 | | | | | | |
| | | Synthetic Example 3 | | | | | | |
| | | Synthetic Example 4 | | | | | | |
| | | Synthetic Example 5 | | | | | | |
| | | Synthetic Example 6 | | | | | | |
| | | Synthetic Example 7 | | | | | | |
| | | Synthetic Example 8 | | | | | | |
| | | Synthetic Example 9 | | | | | | |
| | | Synthetic Example 10 | | | | | | |
| | | Synthetic Example 11 | | | | | | |
| | | Synthetic Example 12 | | | | | | |
| | | Synthetic Example 13 | | | | | | |
| | | Synthetic Example 14 | | | | | | |
| | | Synthetic Example 15 | | | | | | |
| | | Synthetic Example 16 | | | | | | |
| | | Synthetic Example 17 | 4.00 | | | | | |
| | | Synthetic Example 18 | | 4.00 | | | | |
| | | Synthetic Example 19 | | | 4.00 | | | |
| | | Synthetic Example 20 | | | | | | |
| | | TMTE[1] | | | | 4.00 | | |
| | | DGEBA[2] | | | | | 5.00 | |
| | | EOCN[3] | | | | | | 5.00 |
| | polydis[4] | | 0.49 | 0.49 | 0.49 | 0.49 | | |
| | HR5 (PVA) | | 0.99 | 0.99 | 0.99 | 0.99 | | |
| | HF-1M[5] | | | | | 1.31 | 2.84 | 2.73 |
| | TPP[6] | | | | | 0.02 | 5.05 | 0.03 |
| | 2E4MZ[7] | | 0.22 | 0.22 | 0.22 | | | |

TABLE 10-continued

| No. | Epoxy compound (Synthetic Example No.) | | Example 36 | Example 37 | Example 38 | Comparative Example 4 | Comparative Example 5 | Comparative Example 6 |
|---|---|---|---|---|---|---|---|---|
| | Silica | | 22.80 | 22.80 | 22.80 | 27.24 | 31.56 | 31.94 |
| | Filler amount (w %) | | 80 | 80 | 80 | 80 | 80 | 80 |
| | Curing temp | | 120-180-230-290 | 120-180-230-290 | 120-180-230-290 | 120-180-230 | 120-180-230 | 120-180-230 |
| Heat resistance | CTE (ppm/° C.) | $\alpha_1$ (T < Tg) | 7.94 | 8.31 | 7.52 | 11.60 | 14.44 | 12.95 |
| | Tg (° C.) | | Tgl | Tgl | Tgl | 175 | 110 | 140 |

Note: The compounds used in Tables 5 and 6 are as follows.

(1) TMTE: Tris(4-hydroxyphenyl)methane triglycidyl ether (Aldrich Co.) as triphenyl epoxy

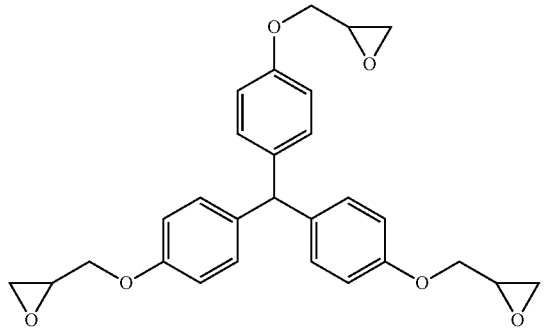 [SMILES: c1cc(C(c2ccc(OCC3CO3)cc2)c2ccc(OCC3CO3)cc2)ccc1OCC1CO1]

(2) DGEBA: Diglycidyl ether of bisphenol A (Aldrich Co.)
(3) EOCN: Epoxy of ortho-cresol novolac (Nippon Kayaku Co.)
(4) polydis: Rubber modified epoxy (Strruktol Co.)
(5) HF-1M: Phenol novolac-based curing agent (Meiwa Plastic Industries)
(6) TPP: Triphenylphosphine (Aldrich Co.)
(7) 2E4MZ: 2-ethyl-4-methyl imidazole (Aldrich Co.)

While the present invention has been shown and described in connection with the exemplary embodiments, it will be apparent to those skilled in the art that modifications and variations can be made without departing from the scope of the present invention as defined by the appended claims.

The invention claimed is:

1. An epoxy compound having an alkoxysilyl group, comprising:
at least two epoxy groups selected from the group consisting of Formulae S41 to S45 and at least one alkoxysilyl group of an S1 substituent independently selected from the group consisting of Formulae S11 to S15 or an S2 substituent independently selected from the group consisting of Formulae S21 to S25 coupled to a core selected from the group consisting of formulae A' to C' and E' to N':

[Formula S1]

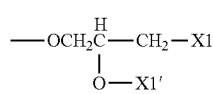
(S11)

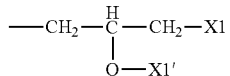
(S12)

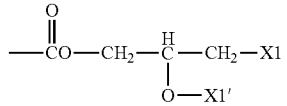
(S13)

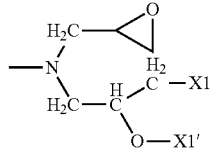
(S14)

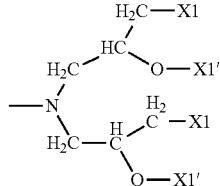
(S15)

in Formulae S11 to S15, X1 is $OR_4$, OH, $NR_4R_5$, $SR_4$ or $OCONH(CH_2)_3SiR_1R_2R_3$, X1' is $CONH(CH_2)_3SiR_1R_2R_3$, at least one of $R_1$ to $R_3$ is an alkoxy group having 1 to 5 carbon atoms, and the remainder are alkyl groups having 1 to 10 carbon atoms, and $R_4$ or $R_5$ may be an alkyl group, an alkenyl group, an aryl group or an aralkyl group having 1 to 20 carbon atoms and may include a hetero atom selected from a group consisting of N, O, P and S,

[Formula S2]

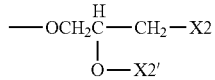
(S21)

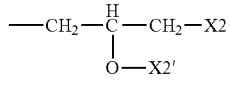
(S22)

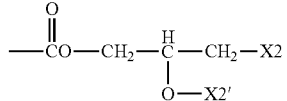
(S23)

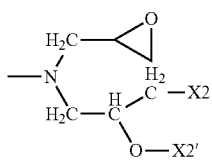 (S24)

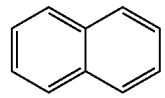 (A')

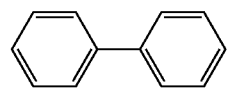 (B')

 (C')

(S25)

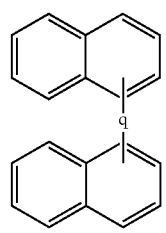 (E')

in Formulae S21 to S25, X2 is $OR_4$, OH, $NR_4R_5$, $SR_4$ or $O(CH_2)_nCH_2CH_2SiR_1R_2R_3$, X2' is $(CH_2)_nCH_2CH_2SiR_1R_2R_3$, at least one of $R_1$ to $R_3$ is an alkoxy group having 1 to 5 carbon atoms, and the remainder are alkyl groups having 1 to 10 carbon atoms, and $R_4$ or $R_5$ may be an alkyl group, an alkenyl group, an aryl group or an aralkyl group having 1 to 20 carbon atoms and may include a hetero atom selected from the group consisting of N, O, P and S,

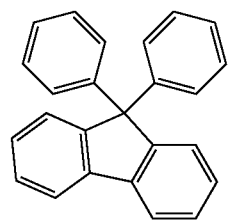 (F')

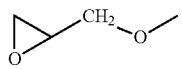 (S41)

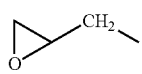 (S42)

(S43)

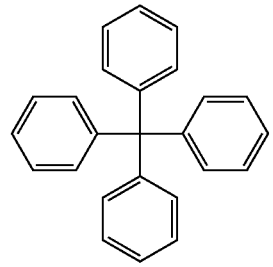 (G')

(S44)

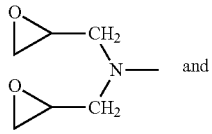 and

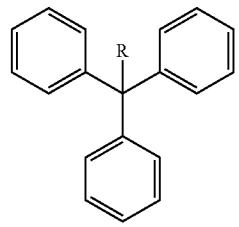 (H')

(S45)

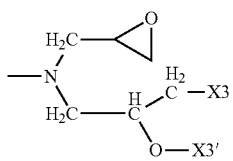

in the formula S45, where X3 is $OR_4$, OH, $NR_4R_5$, $SR_4$, $OCONH(CH_2)_3SiR_1R_2R_3$ or $O(CH_2)_nCH_2CH_2SiR_1R_2R_3$, X3' is H, $CONH(CH_2)_3SiR_1R_2R_3$ or $(CH_2)_nCH_2CH_2SiR_1R_2R_3$, at least one of $R_1$ to $R_3$ is an alkoxy group having 1 to 5 carbon atoms, and the remainder are alkyl groups having 1 to 10 carbon atoms, and $R_4$ or $R_5$ may be an alkyl group, an alkenyl group, an aryl group or an aralkyl group having 1 to 20 carbon atoms and may include a hetero atom selected from the group consisting of N, O, P and S,

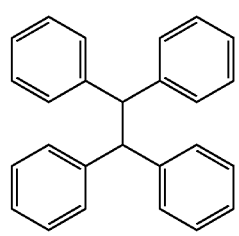 (I')

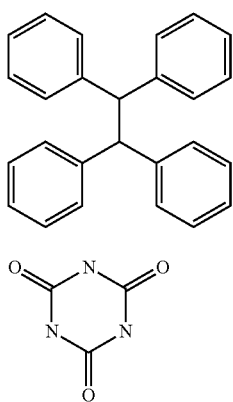
(I')

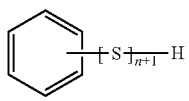
(J')

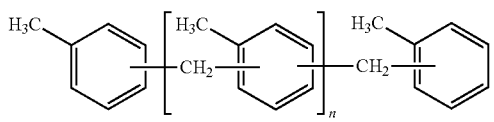
(K')

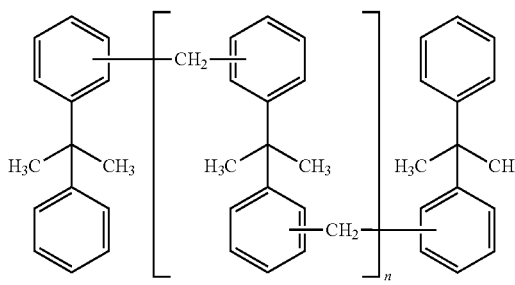
(L')

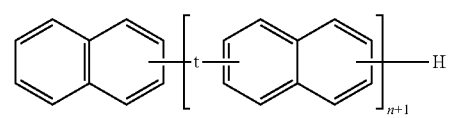
and
(M')

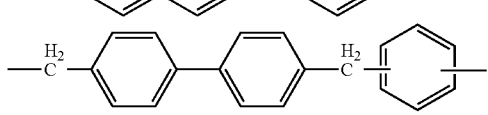
(N')

in Formula E', -q- is —CH$_2$— or a direct linkage,
in Formula H', R is hydrogen, a hydroxyl group, a C1-C10 alkyl group or aromatic group,
in Formula K', S is

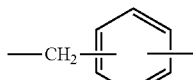

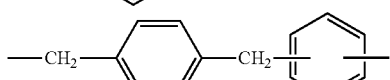

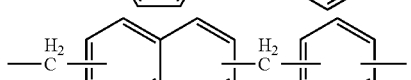

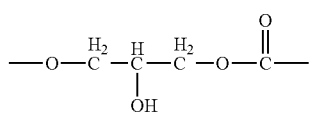

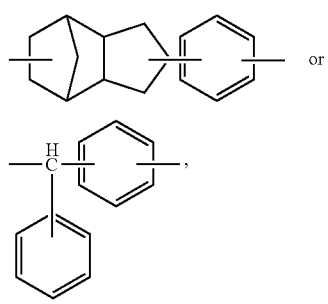
or

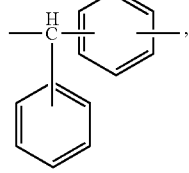
, in Formula N', t is

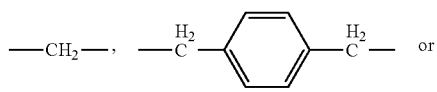
or

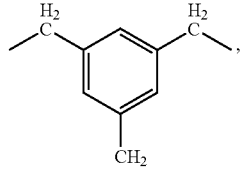
, in Formulae K' to N', n is an integer equal to or greater than 1.

2. The epoxy compound having an alkoxysilyl group of claim 1, wherein the cores selected from the group consisting of Formulae A' to C' and E' to I' are connected via a linking moiety of [Formula 5(2)] selected from the group consisting of Formulae LG1 to LG7, and the cores of Formula J' are connected via Formula LG2,

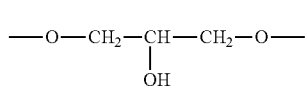
(LG1)

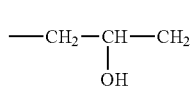
(LG2)

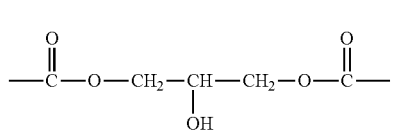
(LG3)

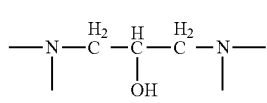
(LG4)

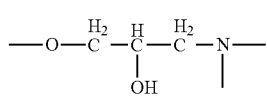
(LG5)

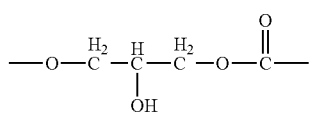
(LG6)

(LG7) 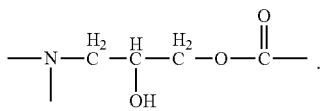

3. The epoxy compound having an alkoxysilyl group of claim 1, wherein the epoxy compound having an alkoxysilyl group further comprises a substituent selected from the group consisting of Formulae S31 to S35:

(S31) 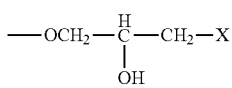

(S32) 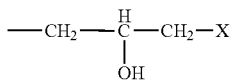

(S33) 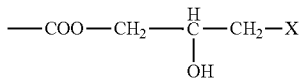

(S34) 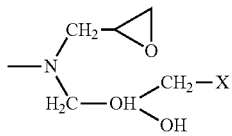

(S35) 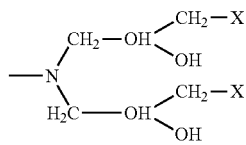

in Formulae S31 to S35, X is $OR_4$, OH, $NR_4R_5$ or $SR_4$, and $R_4$ or $R_5$ may be an alkyl group, an alkenyl group, an aryl group or an aralkyl group having 1 to 20 carbon atoms and may include a hetero atom selected from a group consisting of N, O, P and S.

4. An epoxy composition comprising the epoxy compound having an alkoxysilyl group according to claim 1, a curing agent and at least one filler selected from the group consisting of a fiber and inorganic particles.

5. The epoxy composition of claim 4, further comprising at least one glycidyl-based epoxy compound.

6. A substrate comprising the epoxy composition according to claim 4.

7. A film comprising the epoxy composition according to claim 4.

8. A semiconductor packaging material comprising the epoxy composition of claim 4.

9. A semiconductor device comprising the semiconductor packaging material of claim 8.

10. An adhesive comprising the epoxy composition of claim 4.

11. A paint comprising the epoxy composition of claim 4.

12. A cured product of the epoxy composition of claim 4.

* * * * *